US012595370B2

(12) United States Patent
Nankivil et al.

(10) Patent No.: US 12,595,370 B2
(45) Date of Patent: *Apr. 7, 2026

(54) POLYMERIZABLE ABSORBERS OF UV AND HIGH ENERGY VISIBLE LIGHT

(71) Applicant: Johnson & Johnson Vision Care, Inc., Jacksonville, FL (US)

(72) Inventors: Derek Nankivil, Jacksonville, FL (US); Shivkumar Mahadevan, Jacksonville, FL (US); Dawn D. Wright, St. Augustine, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 755 days.

This patent is subject to a terminal disclaimer.

(21) Appl. No.: 17/810,049

(22) Filed: Jun. 30, 2022

(65) Prior Publication Data

US 2022/0340760 A1 Oct. 27, 2022

Related U.S. Application Data

(63) Continuation-in-part of application No. 17/110,443, filed on Dec. 3, 2020, now Pat. No. 11,820,899, and (Continued)

(51) Int. Cl.

| | |
|---|---|
| ***C09B 62/465*** | (2006.01) |
| ***A61L 27/00*** | (2006.01) |
| ***C08F 230/08*** | (2006.01) |
| ***C08K 5/1545*** | (2006.01) |
| ***C08K 5/45*** | (2006.01) |

(Continued)

(52) U.S. Cl.

CPC ............ *C09B 62/465* (2013.01); *A61L 27/00* (2013.01); *C08F 230/08* (2013.01); *C08L 77/00* (2013.01); *C08L 83/04* (2013.01); *G02B 1/04* (2013.01); *G02B 1/043* (2013.01); *G02C 7/04* (2013.01);

(Continued)

(58) Field of Classification Search

CPC ..................................................... G02B 1/043

See application file for complete search history.

(56) References Cited

U.S. PATENT DOCUMENTS

| | | |
|---|---|---|
| 3,196,150 A | 7/1965 | Martin |
| 3,376,303 A | 4/1968 | Fuchs et al. |

(Continued)

FOREIGN PATENT DOCUMENTS

| | | |
|---|---|---|
| CN | 203965745 U | 11/2014 |
| CN | 106349212 A | 1/2017 |

(Continued)

OTHER PUBLICATIONS

Belikov, V.G., "The Relationship Between Chemical Structure, Properties of Substances and Their Effect on the Organism", Pharmaceutical Chemistry, pp. 27-29, 2007.

(Continued)

*Primary Examiner* — Michael F Pepitone

(74) *Attorney, Agent, or Firm* — Raef M. Shaltout

(57) ABSTRACT

Described are polymerizable high energy light absorbing compounds. The compounds absorb various wavelengths of ultraviolet and/or high energy visible light and are suitable for incorporation in various products, such as biomedical devices and ophthalmic devices.

27 Claims, 17 Drawing Sheets

UV-VIS Transmission Spectrum of Silicone Hydrogel Contact Lenses 9A and 9B

Related U.S. Application Data a continuation-in-part of application No. 16/938,117, filed on Jul. 24, 2020, said application No. 17/110,443 is a continuation of application No. 16/268,897, filed on Feb. 6, 2019, now Pat. No. 10,935,695.

(60) Provisional application No. 62/893,996, filed on Aug. 30, 2019, provisional application No. 62/691,112, filed on Jun. 28, 2018, provisional application No. 62/637,505, filed on Mar. 2, 2018.

(51) Int. Cl.

| | |
|---|---|
| ***C08L 77/00*** | (2006.01) |
| ***C08L 83/04*** | (2006.01) |
| ***G02B 1/04*** | (2006.01) |
| ***G02C 7/04*** | (2006.01) |
| ***G02C 7/10*** | (2006.01) |

(52) U.S. Cl.

CPC .............. *G02C 7/10* (2013.01); *C08K 5/1545* (2013.01); *C08K 5/45* (2013.01)

(56) References Cited

U.S. PATENT DOCUMENTS

| | | | | |
|---|---|---|---|---|
| 3,408,429 | A | 10/1968 | Wichterle | |
| 3,660,545 | A | 5/1972 | Wichterle | |
| 3,769,294 | A | 10/1973 | Catino et al. | |
| 3,808,178 | A | 4/1974 | Gaylord | |
| 4,113,224 | A | 9/1978 | Clark et al. | |
| 4,120,570 | A | 10/1978 | Gaylord | |
| 4,136,250 | A | 1/1979 | Mueller et al. | |
| 4,153,641 | A | 5/1979 | Deichert et al. | |
| 4,197,266 | A | 4/1980 | Clark et al. | |
| 4,436,887 | A | 3/1984 | Chromecek et al. | |
| 4,495,313 | A | 1/1985 | Larsen | |
| 4,659,763 | A | 4/1987 | Gallucci et al. | |
| 4,659,782 | A | 4/1987 | Spinelli | |
| 4,659,783 | A | 4/1987 | Spinelli | |
| 4,716,234 | A * | 12/1987 | Dunks | C08F 20/36 548/259 |
| 4,740,533 | A | 4/1988 | Su et al. | |
| 4,889,664 | A | 12/1989 | Kindt-Larsen et al. | |
| 4,910,277 | A | 3/1990 | Bambury et al. | |
| 4,997,897 | A | 3/1991 | Melpolder | |
| 5,006,622 | A | 4/1991 | Kunzler et al. | |
| 5,034,461 | A | 7/1991 | Lai et al. | |
| 5,039,459 | A | 8/1991 | Kindt-Larsen et al. | |
| 5,070,215 | A | 12/1991 | Bambury et al. | |
| 5,236,969 | A | 8/1993 | Kunzler et al. | |
| 5,244,981 | A | 9/1993 | Seidner et al. | |
| 5,270,418 | A | 12/1993 | Kunzler et al. | |
| 5,298,533 | A | 3/1994 | Nandu et al. | |
| 5,314,960 | A | 5/1994 | Spinelli et al. | |
| 5,331,067 | A | 7/1994 | Seidner et al. | |
| 5,371,147 | A | 12/1994 | Spinelli et al. | |
| 5,470,932 | A | 11/1995 | Jinkerson | |
| 5,480,927 | A | 1/1996 | Janssen et al. | |
| 5,729,322 | A | 3/1998 | Collins et al. | |
| 5,760,100 | A | 6/1998 | Nicolson et al. | |
| 5,776,999 | A | 7/1998 | Nicolson et al. | |
| 5,789,461 | A | 8/1998 | Nicolson et al. | |
| 5,824,719 | A | 10/1998 | Kunzler et al. | |
| 5,849,811 | A | 12/1998 | Nicolson et al. | |
| 5,872,118 | A | 2/1999 | Kelley et al. | |
| 5,916,719 | A | 6/1999 | Kim et al. | |
| 5,944,853 | A | 8/1999 | Molock et al. | |
| 5,945,465 | A | 8/1999 | Ozark et al. | |
| 5,962,548 | A | 10/1999 | Vanderlaan et al. | |
| 5,965,631 | A | 10/1999 | Nicolson et al. | |
| 5,977,219 | A | 11/1999 | Ravichandran et al. | |
| 5,998,498 | A | 12/1999 | Vanderlaan et al. | |
| 6,020,445 | A | 2/2000 | Vanderlaan et al. | |
| 6,022,158 | A | 2/2000 | Nakayama et al. | |
| 6,087,415 | A | 7/2000 | Vanderlaan et al. | |
| 6,158,862 | A | 12/2000 | Patel et al. | |
| 6,166,218 | A | 12/2000 | Ravichandran et al. | |
| 6,207,244 | B1 | 3/2001 | Hesch | |
| 6,244,707 | B1 | 6/2001 | Faubl | |
| 6,367,929 | B1 | 4/2002 | Maiden et al. | |
| 6,373,615 | B1 | 4/2002 | Mann et al. | |
| 6,420,453 | B1 | 7/2002 | Bowers et al. | |
| 6,423,761 | B1 | 7/2002 | Bowers et al. | |
| 6,527,977 | B2 | 3/2003 | Helber et al. | |
| 6,767,979 | B1 | 7/2004 | Muir et al. | |
| 6,807,745 | B2 | 10/2004 | Orton | |
| 6,822,016 | B2 | 11/2004 | McCabe et al. | |
| 6,867,245 | B2 | 3/2005 | Iwata et al. | |
| 6,918,931 | B2 | 7/2005 | Lai et al. | |
| 6,943,203 | B2 | 9/2005 | Vanderlaan et al. | |
| 6,951,894 | B1 | 10/2005 | Nicolson et al. | |
| 7,033,391 | B2 | 4/2006 | Lai et al. | |
| 7,052,131 | B2 | 5/2006 | McCabe et al. | |
| 7,247,692 | B2 | 7/2007 | Laredo | |
| 7,249,848 | B2 | 7/2007 | Laredo et al. | |
| 7,276,544 | B2 | 10/2007 | Lai et al. | |
| 7,396,890 | B2 | 7/2008 | Zanini et al. | |
| 7,461,937 | B2 | 12/2008 | STeffen et al. | |
| 7,468,398 | B2 | 12/2008 | Nicolson et al. | |
| 7,538,146 | B2 | 5/2009 | Nicolson et al. | |
| 7,553,860 | B2 | 6/2009 | Old | |
| 7,553,880 | B2 | 6/2009 | Nicolson et al. | |
| 7,572,841 | B2 | 8/2009 | Chen et al. | |
| 7,666,921 | B2 | 2/2010 | McCabe et al. | |
| 7,691,916 | B2 | 4/2010 | McCabe et al. | |
| 7,691,918 | B2 | 4/2010 | Jinkerson et al. | |
| 7,728,051 | B2 | 6/2010 | Weinschenk, III et al. | |
| 7,781,571 | B2 | 8/2010 | Weinschenk, III et al. | |
| 7,786,185 | B2 | 8/2010 | Rathore et al. | |
| 7,803,359 | B1 | 9/2010 | Jinkerson et al. | |
| 7,825,170 | B2 | 11/2010 | Steffen et al. | |
| 7,915,323 | B2 | 3/2011 | Awasthi et al. | |
| 7,934,830 | B2 | 5/2011 | Blackwell et al. | |
| 7,956,131 | B2 | 6/2011 | Arnold et al. | |
| 7,994,356 | B2 | 8/2011 | Awasthi et al. | |
| 8,022,158 | B2 | 9/2011 | Rathore et al. | |
| 8,026,326 | B2 | 9/2011 | Benz et al. | |
| 8,043,607 | B2 | 10/2011 | Jinkerson | |
| 8,113,655 | B1 | 2/2012 | Tyrin et al. | |
| 8,138,290 | B2 | 3/2012 | Blackwell et al. | |
| 8,153,703 | B2 | 4/2012 | Laredo | |
| 8,163,206 | B2 | 4/2012 | Chang et al. | |
| 8,207,244 | B2 | 6/2012 | Laredo | |
| 8,236,053 | B1 | 8/2012 | Freeman | |
| 8,262,947 | B2 | 9/2012 | Laredo | |
| 8,262,948 | B2 | 9/2012 | Laredo et al. | |
| 8,273,802 | B2 | 9/2012 | Laredo et al. | |
| 8,323,631 | B2 | 12/2012 | Jinkerson | |
| 8,329,775 | B2 | 12/2012 | Laredo | |
| 8,360,574 | B2 | 1/2013 | Ishak et al. | |
| 8,389,597 | B2 | 3/2013 | Blackwell et al. | |
| 8,399,538 | B2 | 3/2013 | Steffen et al. | |
| 8,415,404 | B2 | 4/2013 | Nicolson et al. | |
| 8,420,711 | B2 | 4/2013 | Awasthi et al. | |
| 8,450,387 | B2 | 5/2013 | McCabe et al. | |
| 8,470,906 | B2 | 6/2013 | Rathore et al. | |
| 8,476,390 | B2 | 7/2013 | Benz et al. | |
| 8,487,058 | B2 | 7/2013 | Liu et al. | |
| 8,507,577 | B2 | 8/2013 | Zanini et al. | |
| 8,568,626 | B2 | 10/2013 | Nicolson et al. | |
| 8,585,938 | B1 | 11/2013 | Jinkerson et al. | |
| 8,618,323 | B2 | 12/2013 | Benz et al. | |
| 8,637,621 | B2 | 1/2014 | Iwata et al. | |
| 8,697,770 | B2 | 4/2014 | Duis et al. | |
| 8,703,891 | B2 | 4/2014 | Broad | |
| 8,784,867 | B2 | 7/2014 | Samuel et al. | |
| 8,807,745 | B2 | 8/2014 | Nunez et al. | |
| 8,940,812 | B2 | 1/2015 | Reboul et al. | |
| 8,980,972 | B2 | 3/2015 | Driver | |
| 9,005,700 | B2 | 4/2015 | Bothe et al. | |
| 9,056,878 | B2 | 6/2015 | Fujisawa et al. | |
| 9,057,821 | B2 | 6/2015 | Broad et al. | |
| 9,125,829 | B2 | 9/2015 | Bonda et al. | |

(56) References Cited

U.S. PATENT DOCUMENTS 9,145,383 B2 9/2015 Bonda et al.
9,170,349 B2 10/2015 Mahadevan et al.
9,217,813 B2 12/2015 Liu et al.
9,244,196 B2 1/2016 Scales et al.
9,249,249 B2 2/2016 Awasthi et al.
9,260,544 B2 2/2016 Rathore et al.
9,278,949 B2 3/2016 Loccufier
9,297,928 B2 3/2016 Molock et al.
9,297,929 B2 3/2016 Scales et al.
9,315,669 B2 4/2016 Holland et al.
9,611,246 B2 4/2017 Bonda et al.
9,637,444 B2 5/2017 Qian
9,667,800 B2 5/2017 Rodriguez et al.
9,733,493 B2 8/2017 Wooley
9,765,051 B2 9/2017 Bonda et al.
9,867,800 B2 1/2018 Bonda et al.
9,926,289 B2 3/2018 Bonda et al.
9,927,635 B2 3/2018 Ishak et al.
9,957,258 B2 5/2018 Kunimoto et al.
10,113,075 B2 10/2018 Nesvadba et al.
10,268,053 B2 4/2019 Holland et al.
10,338,408 B2 7/2019 Bothe et al.
10,597,515 B2 3/2020 Nesvadba et al.
10,935,695 B2 * 3/2021 Mahadevan ............. G02B 1/04
11,401,400 B2 8/2022 Shishino et al.
11,543,683 B2 * 1/2023 Mahadevan .......... C09B 69/109
11,820,899 B2 11/2023 Mahadevan et al.
11,993,037 B1 5/2024 Mahadevan et al.
2002/0042653 A1 4/2002 Copeland et al.
2004/0070726 A1 4/2004 Ishak
2005/0018131 A1 1/2005 Ishak
2005/0055090 A1 3/2005 Lai et al.
2005/0055091 A1 3/2005 Lai et al.
2005/0243272 A1 * 11/2005 Mainster ............... A61F 2/1659
351/159.24
2005/0254003 A1 11/2005 Jani et al.
2006/0092374 A1 5/2006 Ishak
2006/0252850 A1 11/2006 Jani et al.
2007/0092830 A1 4/2007 Lai et al.
2007/0092831 A1 4/2007 Lai et al.
2007/0100018 A1 5/2007 Hagting et al.
2007/0216861 A1 9/2007 Ishak et al.
2008/0002147 A1 1/2008 Haywood et al.
2008/0221674 A1 9/2008 Blum et al.
2010/0048847 A1 2/2010 Broad
2010/0113641 A1 5/2010 Laredo
2010/0168359 A1 7/2010 Domschke et al.
2010/0321632 A1 12/2010 Sanger
2011/0245818 A1 10/2011 Weinschenk, III
2011/0249234 A1 10/2011 Duis et al.
2012/0010703 A1 1/2012 Paul et al.
2012/0053313 A1 3/2012 Higgs et al.
2012/0196951 A1 8/2012 Mentak
2012/0262792 A1 10/2012 Goldberg et al.
2013/0009059 A1 1/2013 Caruso
2013/0057824 A1 3/2013 Harding et al.
2013/0095235 A1 4/2013 Bothe et al.
2013/0158150 A1 6/2013 Zhang et al.
2013/0168617 A1 7/2013 Alli et al.
2013/0172440 A1 7/2013 Alli et al.
2013/0217620 A1 8/2013 Alli et al.
2014/0024791 A1 1/2014 Alli et al.
2014/0031447 A1 1/2014 Alli et al.
2014/0044654 A1 2/2014 Bonda et al.
2014/0050681 A1 2/2014 Bonda et al.
2014/0093661 A1 4/2014 Trajkovska et al.
2014/0178595 A1 6/2014 Bothe et al.
2014/0300857 A1 10/2014 Cohen-tannoudji et al.
2015/0092155 A1 4/2015 Chang et al.
2015/0094393 A1 * 4/2015 Holland .................. C08L 83/04
522/66
2015/0094395 A1 4/2015 Alli et al.
2015/0164852 A1 6/2015 Bonda et al.
2015/0175732 A1 6/2015 Awasthi et al.
2015/0316688 A1 11/2015 Cefalo et al.
2016/0002200 A1 1/2016 Bonda et al.
2016/0022555 A1 1/2016 Bonda et al.
2016/0170093 A1 6/2016 Laredo et al.
2017/0038605 A1 2/2017 Legerton
2017/0075137 A1 3/2017 Lin et al.
2017/0131574 A1 5/2017 Lee
2017/0184878 A1 6/2017 Duis et al.
2017/0227790 A1 8/2017 Lin et al.
2017/0261768 A1 9/2017 Ambler et al.
2018/0037690 A1 2/2018 Aitken et al.
2018/0164608 A1 6/2018 Schmeder et al.
2018/0208583 A1 7/2018 Kunimoto et al.
2018/0263951 A1 9/2018 Bonda et al.
2018/0371139 A1 12/2018 Mahadevan et al.
2019/0002415 A1 1/2019 Mahadevan et al.
2019/0002459 A1 1/2019 Mahadevan et al.
2019/0121162 A1 4/2019 Alli et al.
2019/0169438 A1 6/2019 Fromentin et al.
2019/0179170 A1 6/2019 Chang
2019/0271798 A1 9/2019 Mahadevan et al.
2019/0271861 A1 9/2019 Hose
2020/0347166 A1 11/2020 Alli et al.
2020/0347167 A1 11/2020 Alli et al.
2020/0399429 A1 12/2020 Alli et al.
2020/0407324 A1 12/2020 Mahadevan et al.
2020/0407337 A1 12/2020 Mahadevan
2021/0061934 A1 3/2021 Martin et al.
2022/0194944 A1 6/2022 Mahadevan
2022/0340759 A1 10/2022 Riederer et al.
2023/0066936 A1 3/2023 Buch et al.
2023/0085695 A1 3/2023 Buch et al.
2023/0117655 A1 4/2023 Mahadevan et al.
2023/0288728 A1 9/2023 Mahadevan et al.
2023/0296807 A1 9/2023 Aitken et al.

FOREIGN PATENT DOCUMENTS

CN 106366241 A 2/2017
CN 108586289 A 9/2018
EP 0080539 B1 6/1983
EP 0131468 B1 1/1985
EP 0924203 A1 6/1999
EP 1870735 A1 12/2007
EP 2123638 A1 11/2009
EP 3052534 B1 8/2016
EP 3419961 A1 1/2019
EP 3419961 B1 9/2020
GB 217810 6/1924
GB 2319035 A 5/1998
JP H0743918 A 2/1995
JP 2004243596 A 9/2004
JP 2004277581 10/2004
JP 200850463 A 3/2008
JP 4627009 B2 2/2011
JP 2011219512 A 11/2011
JP 5544017 B2 7/2014
JP 2016133593 A 7/2016
RU 2175321 C2 10/2001
RU 2196557 C2 1/2003
RU 2197907 C2 2/2003
RU 2294132 C2 10/2006
RU 2466173 C1 11/2012
RU 2481606 C1 5/2013
RU 2540655 C2 9/2014
RU 2557993 C1 7/2015
RU 2577800 C2 3/2016
RU 2628462 C2 8/2017
WO 1999063366 A1 12/1999
WO 2001030866 A1 5/2001
WO 200212205 A1 2/2002
WO 200242281 A1 5/2002
WO 2003022321 A2 3/2003
WO 2003089519 A1 10/2003
WO 2007050395 A2 5/2007
WO 2008061992 A2 5/2008
WO 2011130139 A1 10/2011
WO 2013055746 A1 4/2013
WO 2013188825 A1 12/2013
WO 2014018208 A1 1/2014

(56) References Cited

FOREIGN PATENT DOCUMENTS

| | | | |
|---|---|---|---|
| WO | 2014025370 | A1 | 2/2014 |
| WO | 2014026151 | A1 | 2/2014 |
| WO | 2015048035 | A1 | 4/2015 |
| WO | 2016100457 | A1 | 6/2016 |
| WO | 2016175619 | A1 | 11/2016 |
| WO | 2017/073467 | A1 | 5/2017 |
| WO | 2017106322 | A1 | 6/2017 |
| WO | 2019166971 | A1 | 9/2019 |
| WO | 2020177534 | A1 | 9/2020 |
| WO | 2020261021 | A1 | 12/2020 |
| WO | 2020261091 | A1 | 12/2020 |
| WO | 2023242688 | A1 | 12/2023 |

OTHER PUBLICATIONS

Dyson et al., "Chemistry of Synthetic Drugs Substances", Moscow: Mir, 18 pages, 1964.
Fadli et al., "Permeation and Pervaporation of Water through Contact Lens Materials", Johnson & Johnson Vision Care, Inc. Jacksonville, FL, USA, 1 page, 2016.
International Search Report and Written Opinion, received for PCT Application No. PCT/IB2018/053669, mailed on Jul. 17, 2018, 14 pages.
International Search Report and Written Opinion, received for PCT Application No. PCT/IB2018/054585, mailed on Nov. 9, 2018, 12 pages.
International Search Report and Written Opinion, received for PCT Application No. PCT/IB2018/054588, mailed on Oct. 4, 2018, 17 pages.
International Search Report and Written Opinion, received for PCT Application No. PCT/IB2023/055938, mailed on Oct. 18, 2023, 12 pages.
ISO 18369-3, "Ophthalmic Optics-Contact lenses", Measurement methods, Part 3, 44 pages, Aug. 15, 2006.
ISO 18369-4, "Ophthalmic Optics-Contact Lenses-Part 4: Physicochemical Properties of Contact Lens Materials", International Organization for Standardization, Aug. 15, 2006, 38 pages.
ISO 9913-1, "Optics and Optical Instruments—Contact Lenses—Part 1: Determination of Oxygen Permeability and Transmissibility by the FATT Method", International Organization for Standardization, Nov. 1, 1996, 16 pages.
PCT International Preliminary Report on Patentability, dated Jun. 13, 2023, for PCT Int'l Appln. No. PCT/IB2021/061175.
Beatty et al., "Macular pigment and age related macular degeneration," Br. J. Ophthalmol. 1999, vol. 83, pp. 867-877.
Belusa, J. et al., 2-(2-Hydroxyphenyl)benzotriazoles. I. Synthesis and their ultraviolet and infrared spectra, Chem.zvesti 1974, vol. 28, No. 5, pp. 673-679.
Bernstein et al., "Lutein, zeaxanthin, and meso-zeaxanthin: The basic and clinical science underlying carotenoid-based nutritional interventions against ocular disease," Progress in Retinal and Eye Research, vol. 50, pp. 34-66, (2016).
Berthon, et al., Synthesis, Electrochemical and Spectroscopic Properties of Pendant Hydroquinone-and Quinone-Substitued Polypyridyl Ruthenium (11) Complex, Inorganica Chimica Acta, 1993, pp. 3-7, vol. 204.
Bondyreva E. Y., "POLIMERIZATION", Methodological Guidelines for Independent Work. Nizhnekamsk Chemical and Technological Institute of the Federal State Budget Educational Institution of Higher Professional Education "Kazan National Research Technological University", Nizhnekamsk, 2014, pp. 4-13.
Boon et al., "Factors Influencing the Chemical Stability of Carotenoids in Foods," Critical Reviews in Food Science and Nutrition, vol. 50, pp. 515-532 (2010).
Burton et al., "B-Carotene autoxidation: oxygen copolymerization, non-vitamin A products, and immunological activity," Can. J. Chem., vol. 92, pp. 305-316 (2014).
Chen et al., Dicyanomethylenated Acridone Based Crystals: Torsional Vibration Confinement Induced Emission with Supramolecular Structure Dependent and Stimuli Responsive Characteristics, The Journal of Physical Chemistry, 2016, 587-597, 120.
Compendium of Polymer Terminology and Nomenclature: IUPAC Recommendations 2008, edited by: Richard G. Jones, Jaroslav Kahovec, Robert Stepto, Edward S. Wilks, Michael Hess, Tatsuki Kitayama, and W. Val Metanomski.
Crivello, et al., Photoinitiators for Free Radical Cationic & Anionic Photopolymerisation, 2nd Edition, vol. III, pp. 275-298, John Wiley and Sons, New York, 1998.
Doutch et al., Ultraviolet Light Transmission through the Human Corneal Stroma Is Reduced in the Periphery, Biophysical Journal, vol. 102, Mar. 2012, pp. 1258-1264.
Hafez et al., Carbonyl and Thiocarbonyl Compounds. V. Synthesis of Newer Unsaturated Nitriles, Carboxylic Acids, and Esters Derived from Xanthene and Thiaxanthene, Journal of Organic Chemistry, vol. 26, pp. 3988-3991, Oct. 1961.
Ham et al., "Retinal sensitivity to damage from short wavelength light." Nature, vol. 260 (1976), pp. 153-155.
Hammond et al., Contralateral comparison of blue-filtering and non-blue-filtering intraocular lenses: glare disability, heterochromatic contrast, and photostress recovery, Clinical Ophthalmology, 2010, pp. 1465-1473, vol. 4, Dovepress, US.
International Conference on Harmonisation (ICH) of Technical Requirements for Registration of Pharmaceuticals for Human Use guideline, Q1B Photostability Testing of New Drug Substances and Products, published on Nov. 1996.
Jockusch et al., Photostabilization of Endogenous Porphyrins: Excited State Quenching by Fused Ring Cyanoacrylates, Photchemical & Photobiological Sciences, 2014, vol. 13, No. 8, pp. 1180-1184.
Johnston et al., "Biologically Active Polymers from Spontaneous Carotenoid Oxidation: A New Frontier in Carotenoid Activity," Plos One, vol. 9, Issue 10, pp. 1-10 (Oct. 2014).
Kolpashchikova et al., "Organic Chemistry" Part II. Arenes. Halogened Hydrocarbons. Ministry of Education of the Russian Federation. Yaroslavl State Technical University, 1999, p. 14.
Larn, et al., Synthesis of Dinucleating Phenanthroline -Based Ligands, Tetrahedron, Jul. 9, 1999, pp. 8377-8384, vol. 55 Issue 28.
Latif et al., Cleavage of Xanthene Ethers A New Route to 9-Substituted Xanthenes, Canadian Journal of Chemistry, vol. 42 (1964), pp. 1736-1740.
Luning, et al., Bimacrocylic 1,10-Phenanthroline Cyclophanes, CHEMISCHE BERI, 1990, pp. 643-645, vol. 123 Issue 3.
Nishino, et al., Manganese (111)-Mediated Carbon-Carbon Bond Formation in The Reaction of Xanthenes With Active Methylene Compounds, The journal of organic chemistry, Jan. 1, 1992, pp. 3551-3557, vol. 57.
PCT International Preliminary Report on Patentability, dated Mar. 1, 2022, for PCT Int'l Appln. No. PCT/IB2020/057732.
PCT International Preliminary Report on Patentability, dated Mar. 1, 2022, for PCT Int'l Appln. No. PCT/IB2020/057733.
PCT International Preliminary Report on Patentability, dated Sep. 8, 2020, for PCT Int'l Appln. No. PCT/IB2019/051582.
PCT International Preliminary Report on Patentability, dated Dec. 28, 2021, for PCT Int'l Appln. No. PCT/IB2020/055485.
PCT International Preliminary Report on Patentability, dated Dec. 28, 2021, for PCT Int'l Appln. No. PCT/IB2020/055868.
PCT International Search Report, dated Mar. 1, 2022, for PCT Int'l Appln. No. PCT/IB2021/061175.
PCT International Search Report, dated Oct. 9, 2020, for PCT Int'l Appln. No. PCT/IB2020/057732.
PCT International Search Report, dated Oct. 9, 2020, for PCT Int'l Appln. No. PCT/IB2020/057733.
PCT International Search Report, dated Jul. 23, 2020, for PCT Int'l Appln. No. PCT/IB2020/055485.
PCT International Search Report, dated Sep. 23, 2020, for PCT Int'l Appln. No. PCT/IB2020/055868.
PCT International Search Report, dated May 24, 2019, for PCT Int'l Appln. No. PCT/IB2019/051582.
Reck, et al., Enantiopure Chiral Chiral Concave 1,10-Phenanthrolines, European Journal of Organic Chemistry, 2016, pp. 1119-1131, vol. 2016 Issue 6.

(56) References Cited

OTHER PUBLICATIONS

Ribeiro et al., "Antioxidant and pro-oxidant activities of carotenoids and their oxidation products," Food and Chemical Toxicology, vol. 120, pp. 681-699 (2018).
Sato, et al., Synthesis and characterization of electron transporting polymers having thioxanthene derivatives, Synthetic Metals, Jan. 1, 1999, pp. 55-60, vol. 105.
Selvam, et al., Tunable anchoring groups@acridone-linked triphenylamine based pendant chromophores and their effects on the photovoltaic performance as sensitizers for dye-sensitized solar cellst, RSC Advances, Jan. 1, 2016, pp. 109054-109060, vol. 6 Issue 110.
Statement on Ocular Ultraviolet Radiation Hazards in Sunlight, American Optometric Association, Nov. 10, 1993.
Stringham et al., "Macular Pigment and Visual Performance in Glare: Benefits for Photostress Recovery, Disability Glare, and Visual Discomfort," IOVS, Sep. 2011, vol. 52, No. 10, pp. 7406-7415.
Sutjagin et al., "Chemistry and Physics of Polymers," Training Manual. TPU Publishing House, Tomsk, 2003, Chapter 1, p. 9, Chapter 2, pp. 19-56.
Takeda et al., Anisotropic Dissociation of π-π Stacking and Flipping-Motion- Induced Crystal Jumping in Alkylacridones and Their Dicyanomethylene Derivatives, Chem. Eur. J., 2016, 7763-7770, 22.
Ty et al., "Oxidation and Thermal Degradation of Carotenoids," Journal of Oil Palm Research, vol. II, No. 1, pp. 62-78 (Jun. 1999).
Chakrabarti et al., "Statistics of Real-World Hyperspectral Images", CVPR 2011, pp. 193-200, Jun. 20-25, 2011.
Das et al., "In vitro and schematic model eye assessment of glare or positive dysphotopsia-type photic phenomena: comparison of a new material IOL to other monofocal IOLs", Journal of Cataract Refractive Surgery, vol. 45, Issue 2, pp. 219-227, Feb. 2019.
Elsherif et al., "Contact Lenses for Color Vision Deficiency", Advanced Materials Technologies, vol. 6, Issue 1, pp. 1-9, Jan. 2021.
Foster et al., "Frequency of Metamerism in Natural Scenes", Journal of the Optical Society of America A, vol. 23, No. 10, pp. 2359-2372, Oct. 2006.
Harris et al., "Effect of Tinted Contact Lenses on Color Vision", Am J Optom Physiol Opt., vol. 53, No. 3, pp. 145-148, Mar. 1976.
Laxer, "Soft Tinted Contact Lenses and Color Discrimination", International Contact Lens Clinic, vol. 17, pp. 88-91, Mar.-Apr. 1990.
Macleod et al., "Chromaticity Diagram Showing Cone Excitation by Stimuli of Equal Luminance", Journal of the Optical Society of America, vol. 69, Issue 8, pp. 1183-1186, Aug. 1979.
Mencucci et al., "Visual Outcome, Optical Quality and Patients' Satisfaction with a New Monofocal Intraocular Lens, Enhanced for Intermediate Vision: Preliminary Results", Journal of Cataract and Refractive Surgery, vol. 46, Issue 3, pp. 378-387, Mar. 2020.
Miao et al., "Objective Optical Quality and Intraocular Scattering in Myopic Adults", Investigative Ophthalmology & Visual Science, vol. 55, No. 9, pp. 5582-5587, Sep. 2014.
Mostafa et al., "The Effect of Age and Gender on Tear Film Breakup Time", In Egyptian Journal of Medical Research, vol. 2, Issue 2, 11 pages, 2021.
Nascimento et al., "Statistics of Spatial Cone-excitation Ratios in Natural Scenes", Journal of the Optical Society of America A, vol. 19, Issue 8, pp. 1484-1490, Aug. 2002.
Parraga et al., "Color and Luminance Information in Natural Scenes", Journal of the Optical Society of America A, vol. 15, No. 3, pp. 563-569, Mar. 1998.
Patel et al., "Effect of Visual Display Unit Use on Blink Rate and Tear Stability", In Optom Visual Sci, vol. 68, Issue 11, pp. 888-892, Nov. 1991.
Pokorny et al., "Aging of the Human Lens", Applied Optics, vol. 26, No. 8, pp. 1437-1440, Apr. 1987.
Stockman et al., "The Spectral Sensitivities of the Middle- and Long-wavelength-sensitive Cones Derived from Measurements in Observers of Known Genotype", Vision Research, vol. 40, pp. 1711-1737, 2000.
Tan et al., "Dynamic Change of Optical Quality in Patients with Dry Eye Disease", In Invest Ophthalmol Vis Sci. Volume 56, Issue 5, pp. 2848-2854, May 2015.
Tester et al., "Dysphotopsia in phakic and pseudophakic patients: incidence and relation to intraocular lens type", In Journal of Cataract Refractive Surgery Voume 26, Issue 6, pp. 810-816, Jun. 2000.
Tsubota et al., "Dry Eyes and Video Display Terminals", In New England Journal of Medicine, vol. 328, Issue 8, p. 584, Feb. 25, 1993.
Van den Berg, T. J. T. P, "Importance of Pathological Intraocular Light Scatter for Visual Disability." In Documenta Ophthalmologica, vol. 61, pp. 327-333, 1986.
Xi et al., "Assessment of Tear Film Optical Quality in a Young Short Tear Break-up Time Dry Eye: Case-control study", Medicine, vol. 98, Issue 40, pp. 1-6, 2019.
Liu, Zhuo., "Tutorial on Modern Rock and Mineral Analytic Experiments", Geological Press, p. 42, Oct. 31, 2015.
Krick et al. "Temperature—DependentDynamics of Push—Pull Rotor SystemsBased on Acridinylidene CyanoaceticEsters", European Journal of Organic Chemistry, pp. 5141-5146, Jul. 26, 2017.
Ma et al., "Studies on K2CO3—Catalyzed 1,4—Addition of 1,2—Allenic Ketones with Diethyl Malonate:Controlled Selective Synthesis of β, γ—Unsaturated Enones and α—Pyrones", Journal of Organic Chemistry, vol. 68, pp. 8996-9002, Oct. 24, 2003.
Maas et al., "Dication Ethers-10. Stable Dipoles from A Bis-Acridinium Ether Salt and Cyclic Beta-Diketonates", Tetrahedron, vol. 41, No. 20, pp. 4529-4536, 1985.

* cited by examiner

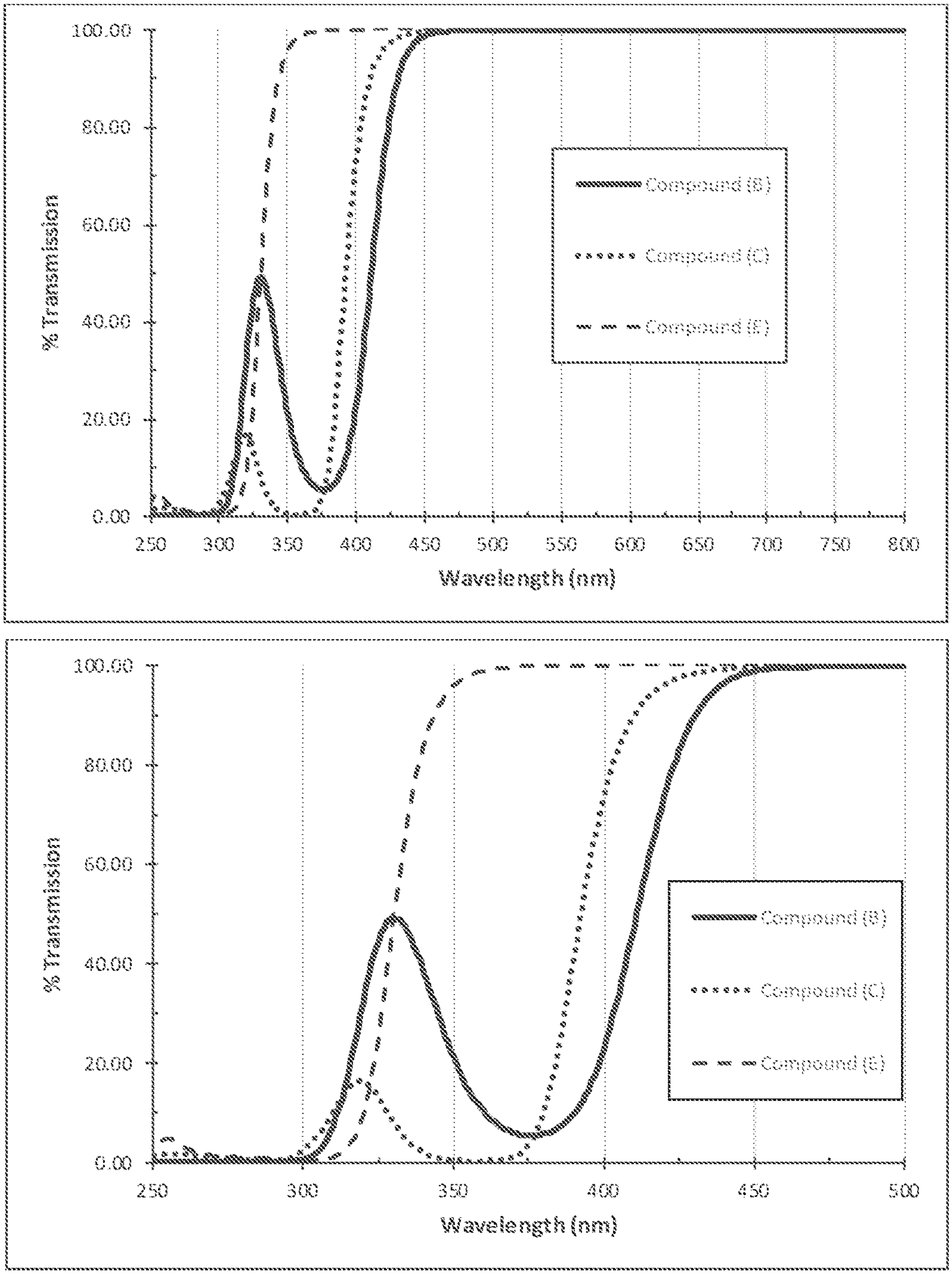
FIG. 1 – UV-VIS Transmission Spectra of 0.2 mM solutions of Compounds (B), (C), and (E) in methanol

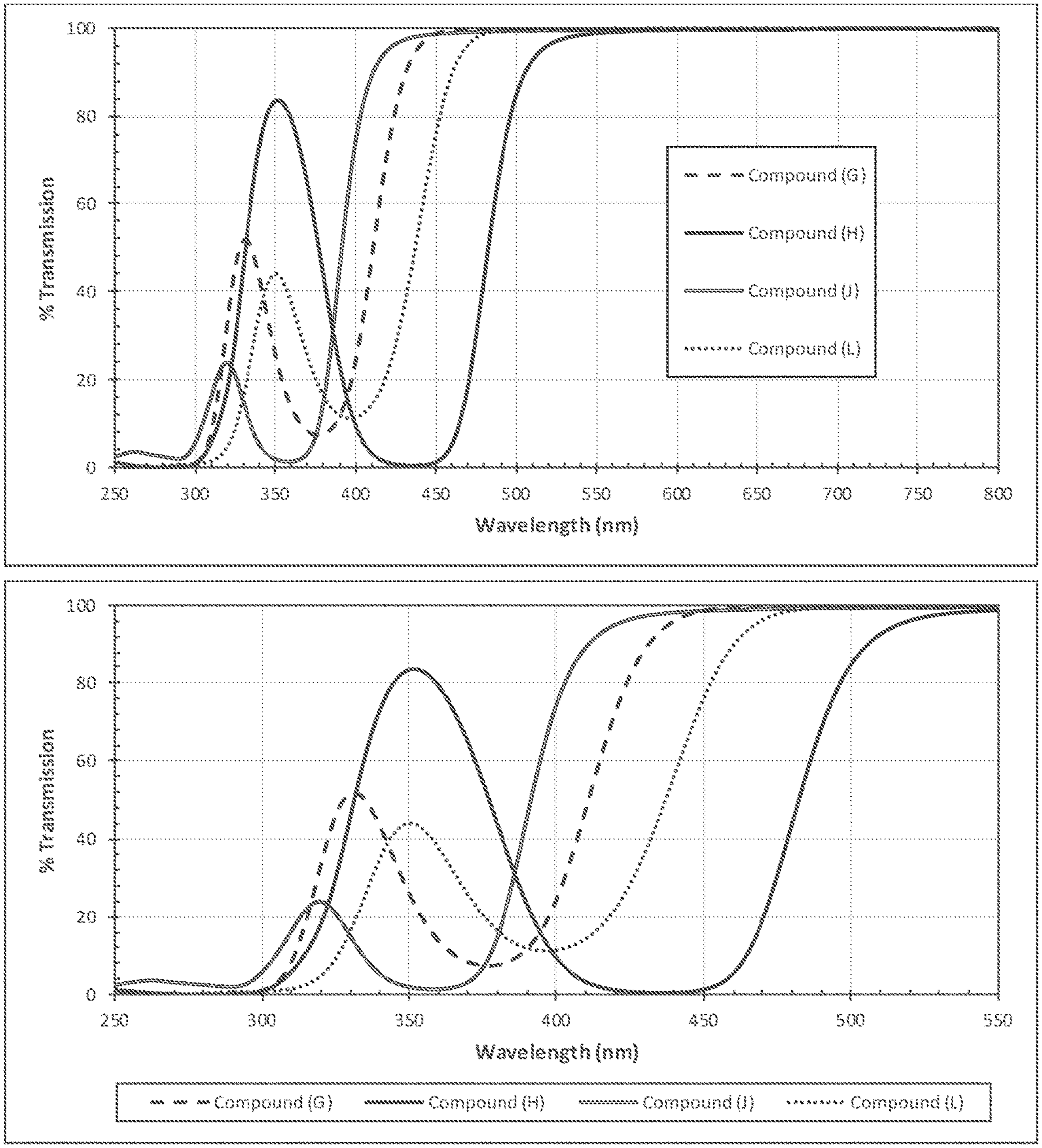
FIG. 2 - UV-VIS Transmission Spectra of 0.2 mM solutions of Compounds (G), (H), and (J) in methanol and of Compound (L) in dichloromethane

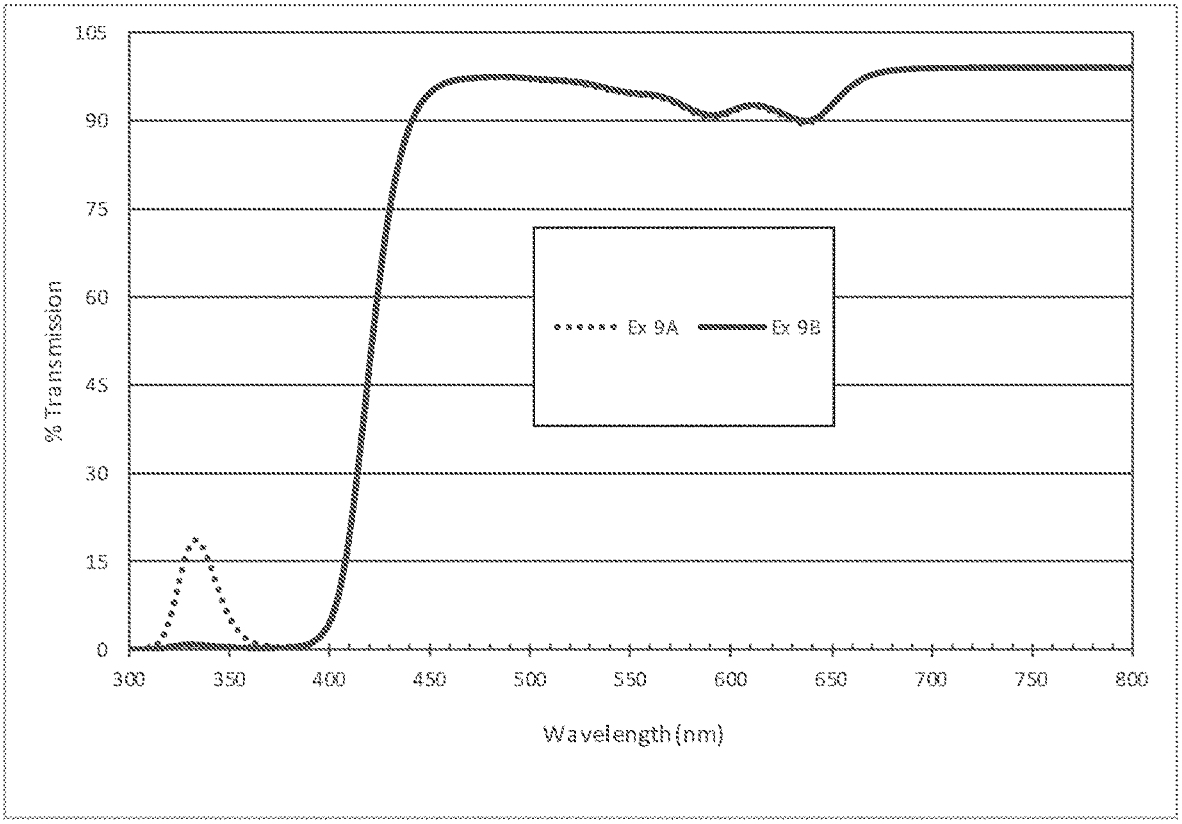
FIG. 3 – UV-VIS Transmission Spectrum of Silicone Hydrogel Contact Lenses 9A and 9B

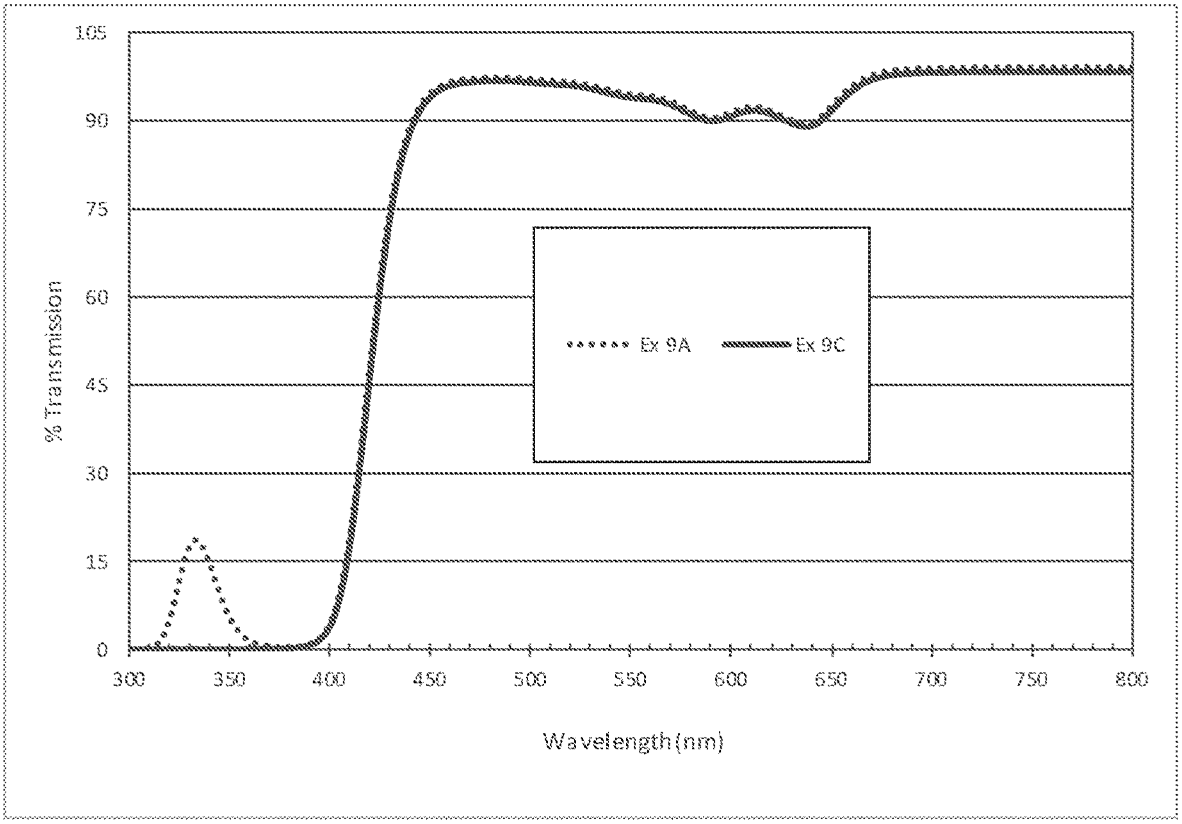
FIG. 4 – UV-VIS Transmission Spectrum of Silicone Hydrogel Contact Lenses 9A and 9C

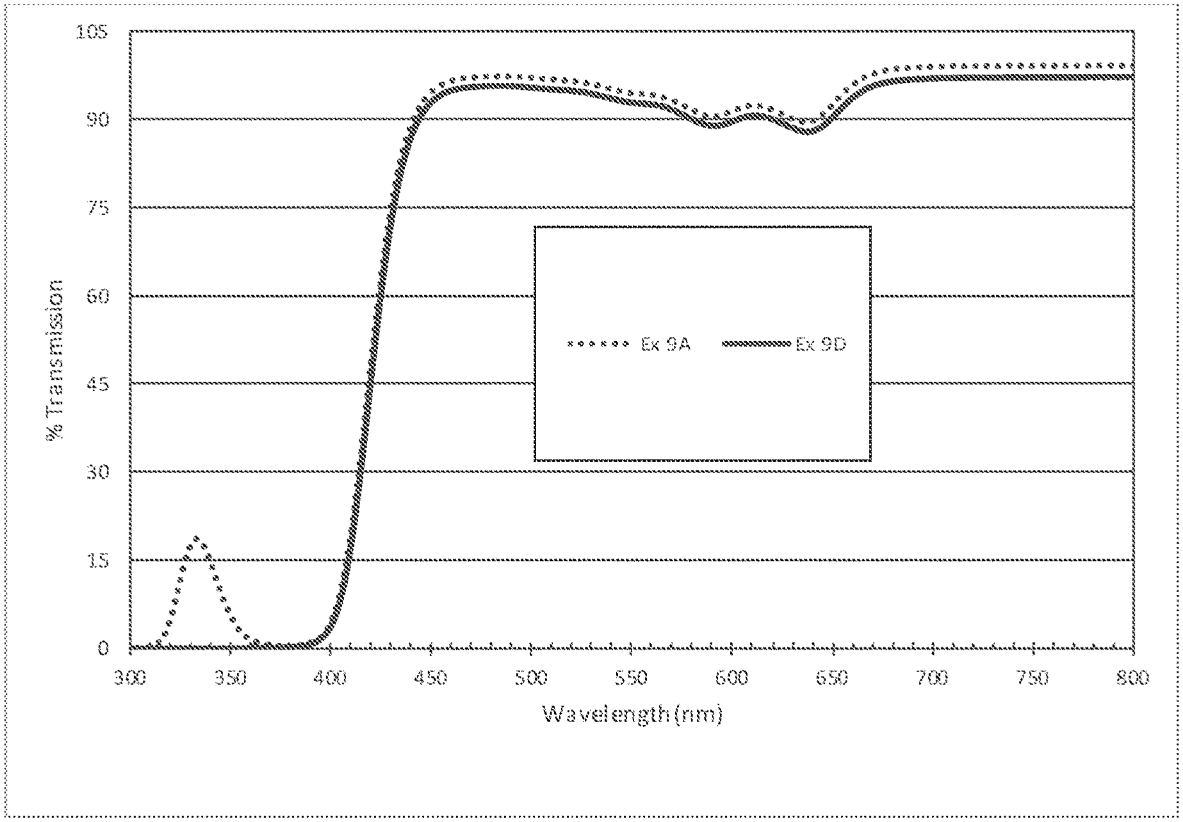
FIG. 5 – UV-VIS Transmission Spectrum of Silicone Hydrogel Contact Lenses 9A and 9D

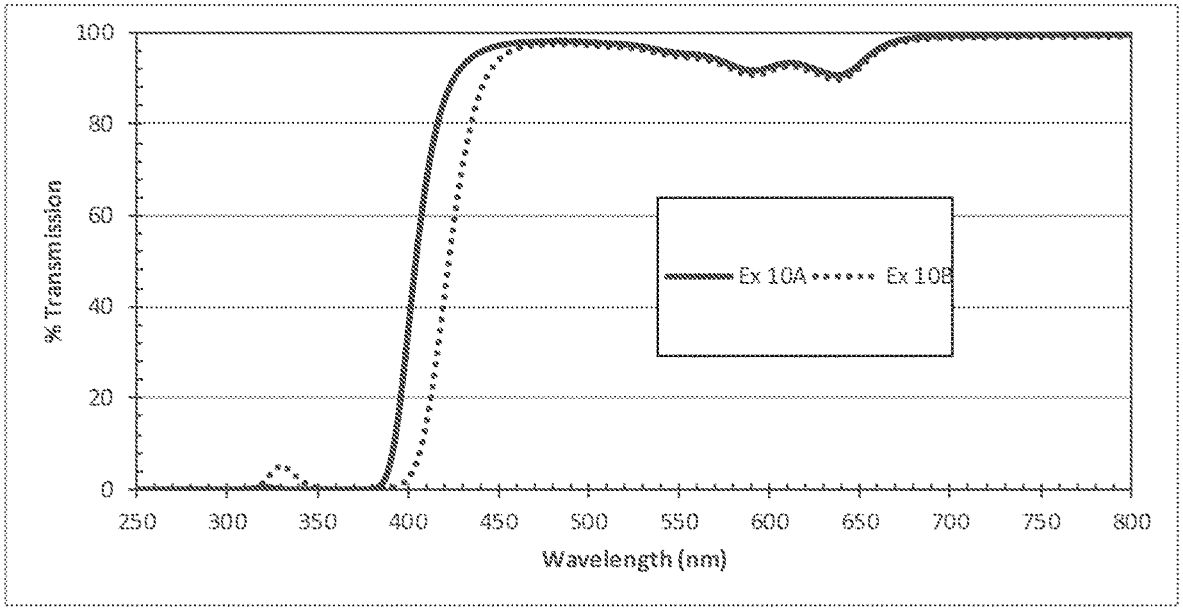
FIG. 6 – UV-VIS Transmission Spectrum of Silicone Hydrogel Contact Lenses 10A and 10B

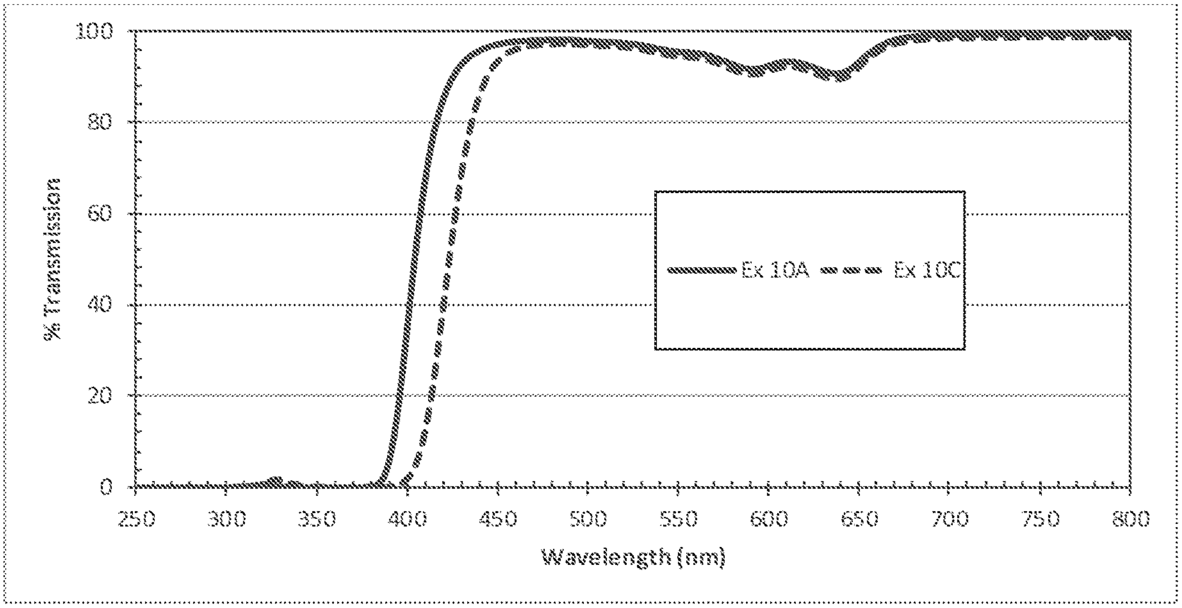
FIG. 7 – UV-VIS Transmission Spectrum of Silicone Hydrogel Contact Lenses 10A and 10C

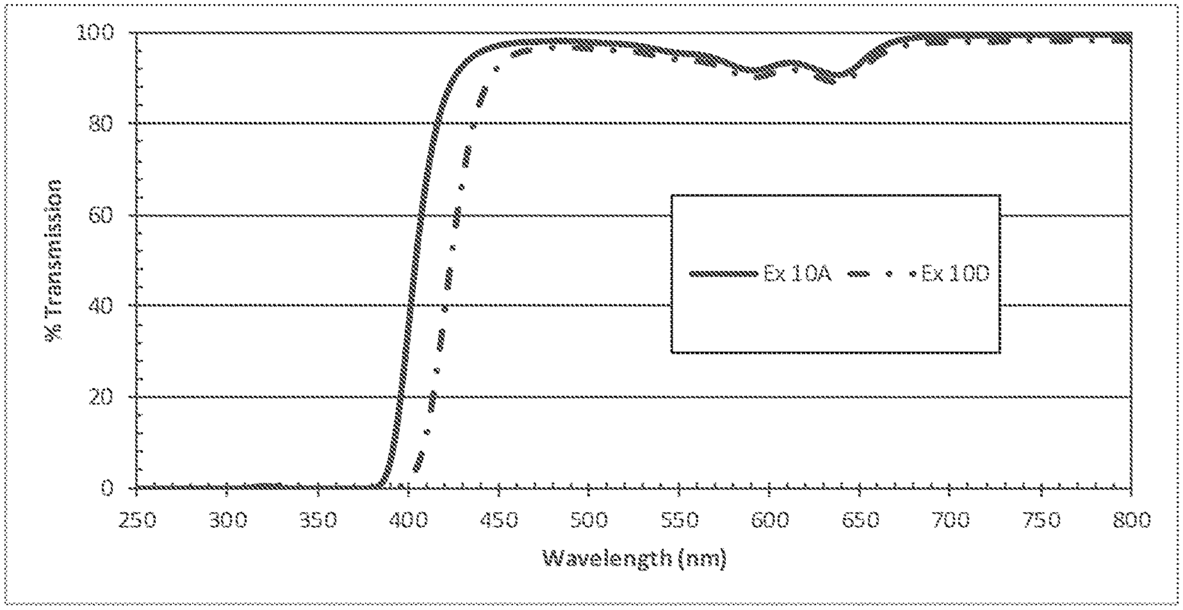
FIG. 8 – UV-VIS Transmission Spectrum of Silicone Hydrogel Contact Lenses 10A and 10D

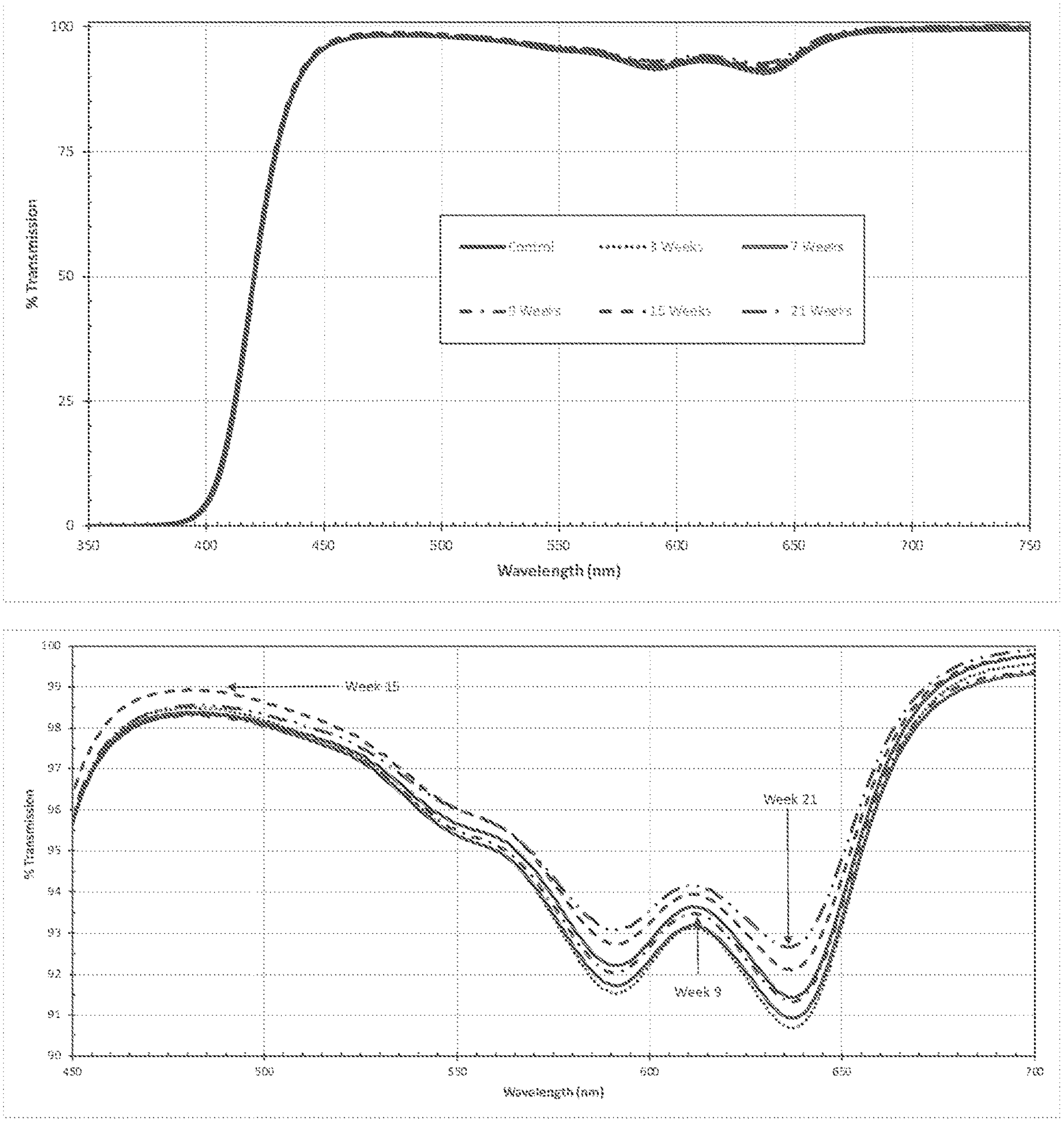
FIG. 9 – UV-VIS Transmission Spectra of Silicone Hydrogel Contact Lenses (11A) comprising Compound (B) after exposure to direct sunlight

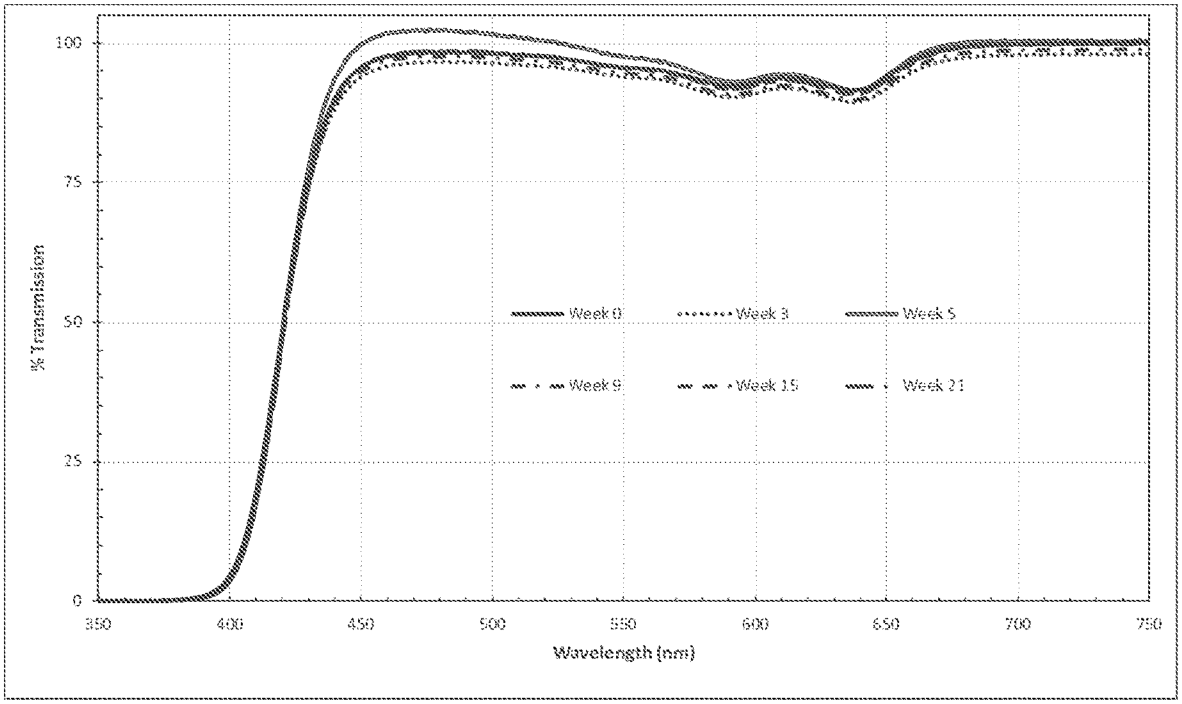
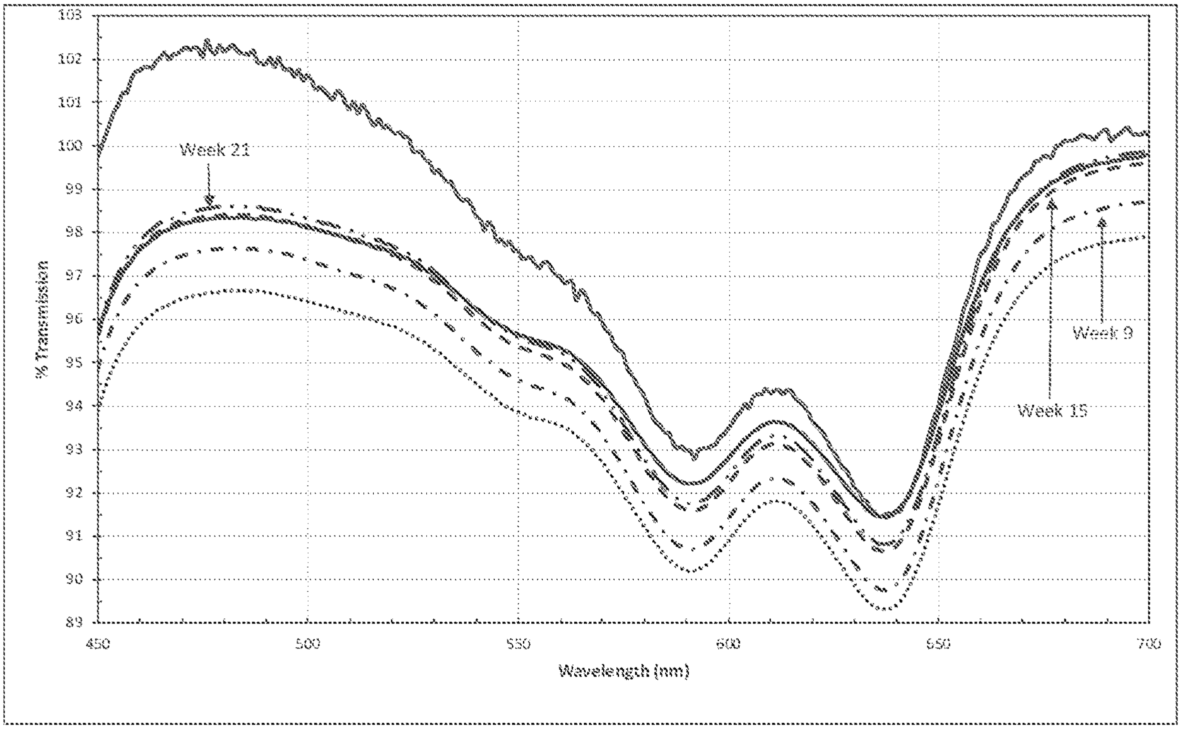
FIG. 10 – UV-VIS Transmission Spectra of Silicone Hydrogel Contact Lenses (11B) comprising Compound (B) after exposure to indoor lighting

POLYMERIZABLE ABSORBERS OF UV AND HIGH ENERGY VISIBLE LIGHT

RELATED APPLICATIONS

This application is a continuation-in-part of U.S. patent application Ser. No. 16/938,117, filed Jul. 24, 2020, which claims priority to U.S. Provisional Patent Application Ser. No. 62/893,996, filed Aug. 30, 2019, and is a continuation-in-part of U.S. patent application Ser. No. 17/110,443, filed Dec. 3, 2020, which is a continuation of U.S. patent application Ser. No. 16/268,897, filed on Feb. 6, 2019, now U.S. Pat. No. 10,935,695, which claims priority to U.S. Provisional Patent Application Ser. No. 62/691,112, filed Jun. 28, 2018, and U.S. Provisional Patent Application Ser. No. 62/637,505, filed Mar. 2, 2018, each of which is incorporated herein by reference in its entirety.

FIELD OF THE INVENTION

The invention relates to ultraviolet (UV) and high energy visible (HEV) light absorbers. More particularly, the invention relates to compounds with polymerizable functionality that absorb various wavelengths of UV and/or high energy visible light, and yet are visibly transparent when incorporated in an article. Thus, the compounds may be used in polymeric articles, including biomedical devices, such as ophthalmic devices.

BACKGROUND OF THE INVENTION

High energy light from the sun, such as UV light and HEV light, is known to be responsible for cellular damage. While most of the radiation below 280 nm in wavelength is absorbed by the earth's atmosphere, photons possessing wavelengths ranging between 280 and 400 nm have been associated with several ocular disorders including corneal degenerative changes, and age-related cataract and macular degeneration. (See Statement on Ocular Ultraviolet Radiation Hazards in Sunlight, American Optometric Association, Nov. 10, 1993). The human cornea absorbs some radiation up to 320 nm in wavelength (30% transmission) (Doutch, J. J., Quantock, A. J., Joyce, N. C., Meek, K. M, *Biophys. J,* 2012, 102, 1258-1264), but is inefficient in protecting the back of the eye from radiation ranging from 320 to 400 nm in wavelength.

Contact lens standards define the upper UV radiation wavelength at 380 nm. The current Class I UV absorbing criteria defined by the American Optometric Association require >99% of the radiation between 280 and 315 nm (UV B) and >90% of the 316 to 380 nm (UV A) radiation to be absorbed by the contact lens. While the criteria effectively address protection of the cornea (<1% UV B transmittance), there is little attention paid to the lower energy UV radiation (>380<400 nm) associated with retinal damage (Ham, W. T, Mueller, H. A., Sliney, D. H. *Nature* 1976; 260(5547):153-5) or to HEV radiation.

HEV radiation may cause visual discomfort or circadian rhythm disruption. For example, natural sunlight, computer and electronic device screens, flat screen televisions, energy efficient lights, and light emitting diode (LED) sources are known to emit HEV light. Prolonged exposure to such sources of HEV light may cause eye strain. Viewing HEV light emitting devices at night is also postulated to disrupt the natural circadian rhythm leading, for example, to inadequate sleep.

Absorption of high energy light radiation before it reaches the eye continues to be a desirable goal in the ophthalmic field. However, the extent to which a particular wavelength range is absorbed is also important. For instance, in the UV A and UV B ranges, it may be desirable to absorb as much radiation as possible. On the other hand, since HEV light forms a part of the visible spectrum, complete absorption of HEV light may negatively affect vision. With HEV light, therefore, partial absorption may be more desirable.

Tinting contact lenses has been suggested as a means of influencing chromatic discrimination (not color appearance) in patients with color vision deficiencies (Elsherif et a., 2021). Heavy tinting (such as is sometimes done with lenses used in sports) has been shown to influence chromatic discrimination in normal subjects (Harris et al., 1976; Laxer, 1990). The effects of tinting as one might see in more common use on color appearance, however, has not been tested.

There is a need for materials that provide targeted absorption of undesirable wavelengths of high energy radiation, and that are processable into functional products. Compounds that absorb or attenuate high energy radiation, when used in ophthalmic devices, can help protect the cornea, as well as the interior cells in the ocular environment, from degradation, strain, and/or circadian rhythm disruption.

SUMMARY OF THE INVENTION

The invention relates to high energy light absorbing compounds that absorb UV and/or HEV light while substantially transmitting (e.g., greater than 80% transmission) at wavelengths longer than about 450 nm. The compounds are therefore effective at providing targeted absorption of high energy light, such as UV (UVA and UVB), low energy UV light (385 nm to 400 nm), or HEV light (e.g., 400 to 450 nm).

The compounds are also polymerizable and are generally compatible with other raw materials, as well as the polymerization and processing conditions that are typically used for making ophthalmic devices such as soft contact lenses. The compounds can therefore be readily covalently incorporated into the final product without the need for significant modification of existing manufacturing processes and equipment.

Accordingly, in one aspect the invention provides a compound of formula I:

Formula I

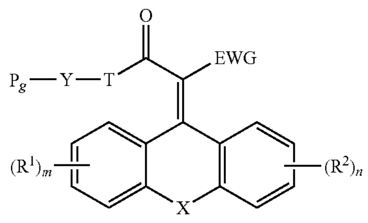

wherein:

m and n are independently 0, 1, 2, 3, or 4;

T is a bond, O, or NR;

X is O, S, NR, SO, or $SO_2$;

Y is a linking group;

$P_g$ is a polymerizable group;

R at each occurrence is independently H, $C_1$-$C_6$ alkyl, cycloalkyl, heterocycloalkyl, aryl, heteroaryl, or Y—$P_g$;

$R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group, such as cyano, amide, ester, keto, or aldehyde (preferably cyano).

In another aspect, the invention provides an ophthalmic device that is a free radical reaction product of a reactive mixture comprising: one or more monomers suitable for making the ophthalmic device; and a polymerizable high energy light absorbing compound comprising a compound of formula I as described herein.

In a further aspect, the invention provides a method for making an ophthalmic device. The method comprises: (a) providing a reactive mixture containing a compound of formula I as described herein, one or more device forming monomers, and a radical initiator; and (b) polymerizing the reactive mixture to form the ophthalmic device.

In a still further aspect, the invention provides an ophthalmic device that is a reaction product of a reactive mixture comprising: a polymerizable high energy light absorbing compound; and one or more monomers suitable for making an ophthalmic device, wherein the ophthalmic device transmits: 45 percent or less of light having a wavelength of 280 to 399 nm; from 1 percent to 70 percent of light having a wavelength of 400 to 409 nm; and at least 80 percent of light having a wavelength of 450 to 800 nm.

As an example, the nominal middle wavelength of the transition band of ophthalmic device in accordance with the present invention is 422 nm. In other words, the filter may nominally blocks 50% or more of HEV light from 422 nm and below. As a further example, a filter may be used to effect an ophthalmic device exhibiting between 1 and 70% transmission from 400 to 429 nm. As a further example, a filter may be used to effect an ophthalmic device transmits from 1 percent to 70 percent of light across a wavelength range of 400 to 409 nm, and from 10 percent to 95 percent of light across a wavelength range of 410 to 424 nm. The exhibited transmission may neglect surface reflectance, also referred to as Fresnel losses or Fresnel reflectance or reflection loss.

In a yet further aspect, the invention provides an ophthalmic device that is a polymerized reaction product of a reactive mixture comprising one or more reactive components (such as a hydrophilic component and a silicone containing compound), wherein the polymerized reaction product contains, as covalently bound substituents, one or more chromophores of formula IV:

Formula IV

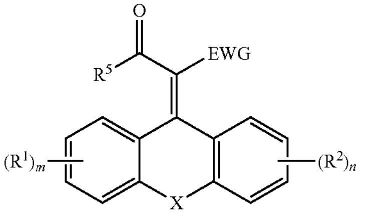

wherein m, n, X, $R^1$, $R^2$, $R^5$, and EWG are as defined herein.

BRIEF DESCRIPTION OF DRAWINGS

FIG. 1 shows UV-VIS Transmission Spectra of 0.2 mM solutions of exemplary Compounds (B), (C), and (E) in methanol.

FIG. 2 shows UV-VIS Transmission Spectra of 0.2 mM solutions of Compounds (G), (H), and (J) in methanol and of Compound (L) in dichloromethane FIG. 3 shows UV-VIS Transmission Spectrum of exemplary Silicone Hydrogel Contact Lenses 9A and 9B.

FIG. 4 shows UV-VIS Transmission Spectrum of exemplary Silicone Hydrogel Contact Lenses 9A and 9C.

FIG. 5 shows UV-VIS Transmission Spectrum of exemplary Silicone Hydrogel Contact Lenses 9A and 9D.

FIG. 6 shows UV-VIS Transmission Spectrum of exemplary Silicone Hydrogel Contact Lenses 10A and 10B.

FIG. 7 shows UV-VIS Transmission Spectrum of exemplary Silicone Hydrogel Contact Lenses 10A and 10C.

FIG. 8 shows UV-VIS Transmission Spectrum of exemplary Silicone Hydrogel Contact Lenses 10A and 10B.

FIG. 9 shows UV-VIS Transmission Spectra of Silicone Hydrogel Contact Lenses (11A) comprising Compound (B) after exposure to direct sunlight FIG. 10 shows UV-VIS Transmission Spectra of Silicone Hydrogel Contact Lenses (11B) comprising Compound (B) after exposure to indoor lighting FIG. 11 displays spectral transmission of a test and control lens according to the present disclosure.

DETAILED DESCRIPTION OF THE INVENTION

Figure 11:
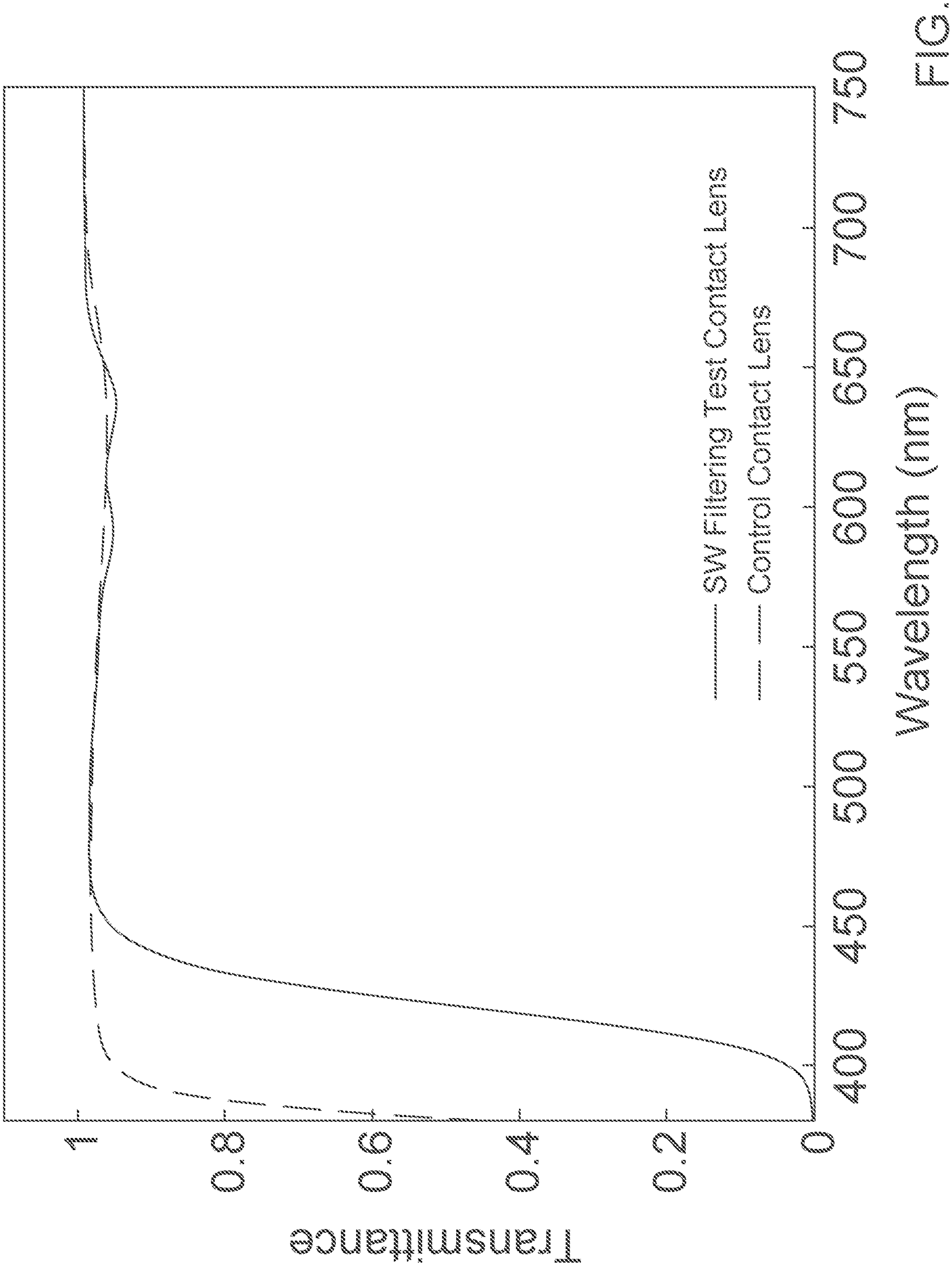

It is to be understood that the invention is not limited to the details of construction or process steps set forth in the following description. The invention is capable of other embodiments and of being practiced or being carried out in various ways using the teaching herein.

As noted above, in one aspect, the invention provides UV/HEV absorbing compounds. The compounds contain polymerizable functionality. It has been discovered that ophthalmic devices that absorb substantial amounts of UV light as well as some amounts of HEV light can be readily prepared as described herein.

It has also been discovered that light absorbing compounds can be selected to provide targeted absorption of UV and/or high energy visible light (e.g., increased UV absorption and less HEV absorption, or increased HEV absorption, etc.). Such targeting may be achieved, for example, with compounds of formula I, which contain a hetero tricyclic core chromophore. For instance, as described in more detail below, compounds of formula I where the heteroatom (X in formula I) is sulfur, may absorb HEV light. On the other hand, compounds of formula I where the heteroatom is oxygen (X is O) may absorb less HEV light, but more UV light. Thus, the compounds may be used to absorb select regions of UV and/or HEV light or they may be mixed together or with other absorbing compounds to provide broad spectrum protection (e.g., UV and HEV light). Advantageously, the compounds exhibit a transmission cut-off (e.g., they absorb 20 percent or less) at visible wavelengths of 450 nm or longer.

It has further been discovered that compounds of formula I are substantially photostable, meaning that the compounds, when incorporated in an ophthalmic device, do not undergo significant degradation over time when exposed to lighting, such as indoor or outdoor lighting. Such photostability can be determined by measuring the UV/Vis transmission spectrum of the ophthalmic device over a test period, such as 21 weeks. Significant changes in the spectrum over the test period are indicative of a lack of photostability. By way of example, ophthalmic devices (such as contact lenses) containing compounds of the invention, when exposed to indoor office lighting over a 21 week period at room temperature, exhibit 5% or less, preferable 2% or less, more preferably 0.5% or less, even more preferably 0.4% or less of change in their average transmission over a wavelength range of 380 to 700 nm. By way of further example, ophthalmic devices (such as contact lenses) containing compounds of the invention, when exposed to indoor office lighting over a 21 week period at room temperature, exhibit 5% or less, preferable 2% or less, more preferably 1% or less, even more preferably 0.7% or less of change in their average transmission over a wavelength range of 400 to 500 nm. Such changes may be calculated as the absolute value of the difference between the average transmission (over the indicated wavelength range) at time 21 weeks and at time zero.

Thus, compounds of the invention may successfully absorb UV (UVA, UVB), and/or HEV, while transmitting in the visible spectrum. The compounds are suitable for incorporation in a variety of products, including biomedical devices and ophthalmic devices.

The present disclosure relates to ophthalmic devices. Such devices may filter visible light in chosen regions, as described above. Light may be filtered in a variety of wavelengths including from about 400 nm to about 500 nm (e.g., short-wavelength (SW)) or from about 400 nm to about 450 nm (e.g., HEV), and the like. Filtering light in the previously disclosed wavelength ranges may impart a tint to an ophthalmic device, as shown in FIG. 11. The control lens of FIG. 11 comprises a UV absorbing compound and a blue visibility tint. Such a combination comprises a relatively clear color profile relative to the test lens. Clear color profile may transmit at least 85% across the visible spectrum from 400 to 700 nm.

The present disclosure relates to incorporation of compounds into biomedical and ophthalmic devices. Incorporation into such devices may influence color appearance to a user. This possibility requires that altered color appearance due to the incorporation of compounds be studied. Color appearance can be measured by additive tricolorimetry where three color primaries (red, green and blue) are mixed to achieve a perfect neutral white. Subject settings are plotted in CIE space as x,y chromaticity coordinates. This type of geometric representation of color space allows specification of the appearance of any mixture of light, rather than its spectral composition, by specific coordinates. Disruptions from normal trichromatic color vision are represented as alterations in the relative amounts of the color primaries used to create a perfect perceived neutral white. Because each variable is on a continuous scale, even small alterations in color appearance can be assessed.

Figure 18A:
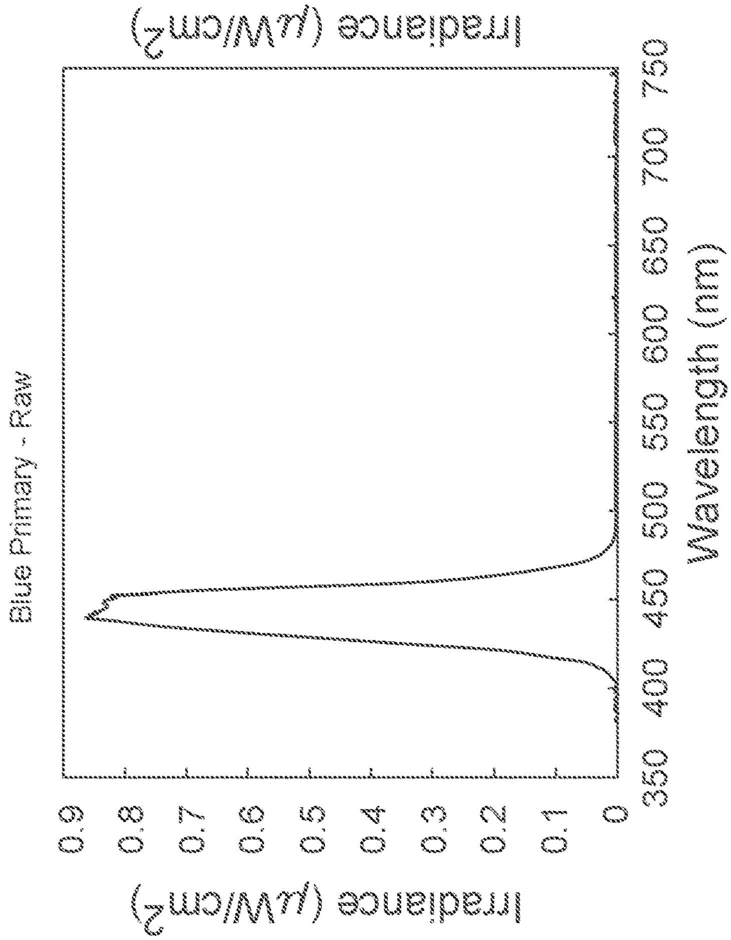
FIGS. 18A-18B display spectral radiance of blue primary (FIG. 18A) and blue primary filtered by short wavelength filtering and the clear control contact lenses (FIG. 18B).
Figure 18B:
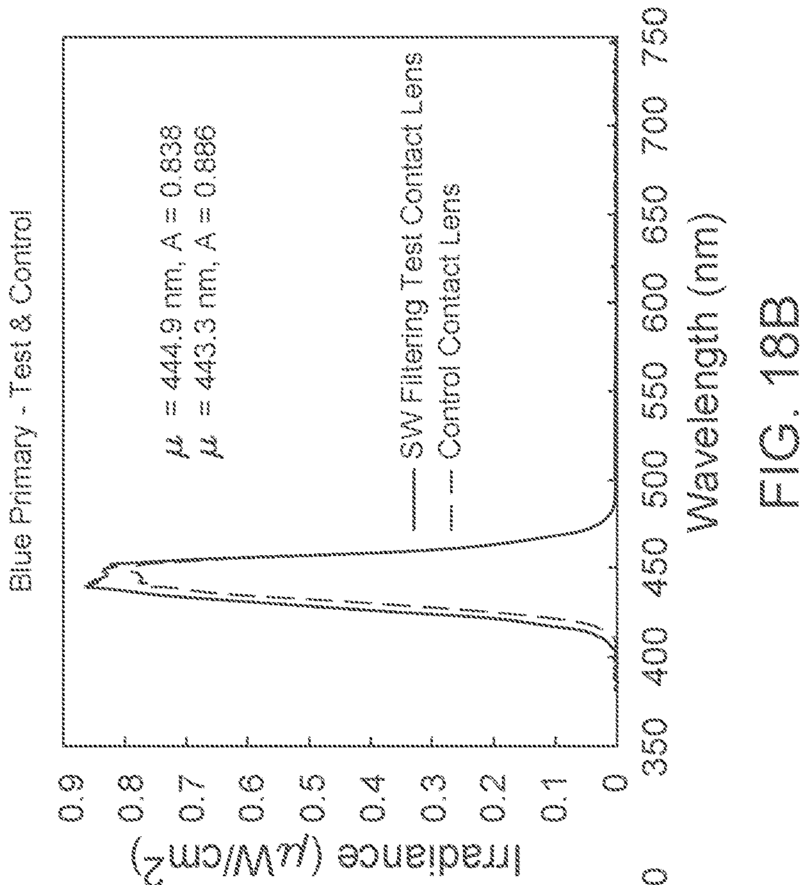

The present disclosure relates to compounds absorbing in HEV and SW spectrums while demonstrating negligible color perception impacts. SW-filtering compounds have a modest impact on the blue primary of the tristimulus colorimeter, shifting the peak wavelength by about 1.6 nm and decreasing the amplitude of the irradiance by about 5.4% (FIGS. 18A-18B). This modest impact implies a negligible effect of SW-filtering compounds on color perception of blue primary. Blue primary is often used in common display technology. This implies that SW-filtering compounds according to the present disclosure do not adversely impact color perception of similar displays.

The present disclosure relates to characterizing functional impacts of biomedical or ophthalmic devices with respect to natural light. Natural light may affect a user's perception of the natural world. Measuring functional impacts with respect to natural light may employ hyperspectral images of natural scenes. Any shifts in color chromaticity conferred by the SW-filtering lens may not equate to changes in color appearance. Chromatic adaptation may 'rebalance' color appearance to compensate for initial changes in receptor signals caused by the filter. However, the colored filter may still affect the range of color contrasts available to the observer. Colors in RGB images have different spectra to those in natural scenes, and correspondingly the effects of filters on RGB images will be different to their effects on natural scenes. It is therefore desirable to use hyperspectral images, where full spectral information is available at each pixel.

To estimate the impact of a SW-filtering lens on color perception in natural environments, models of the visual responses of individual observers to light in the real world were produced. Summary statistics of the predicted effects of the tested tinted lenses on the gamut of colors available to a standard observer in a series of hyperspectral images acquired in natural scenes indicates that the SW-filtering lenses using compounds of the present disclosure are not expected to change the gamut of color contrasts appreciably.

As an example, the nominal middle wavelength of the transition band of ophthalmic device in accordance with the present invention is 422 nm. In other words, the filter may nominally blocks 50% or more of HEV light from 422 nm and below. As a further example, a filter may be used to effect an ophthalmic device exhibiting between 1 and 70% transmission from 400 to 429 nm. As a further example, a filter may be used to effect an ophthalmic device transmits from 1 percent to 70 percent of light across a wavelength range of 400 to 409 nm, and from 10 percent to 95 percent of light across a wavelength range of 410 to 424 nm. The exhibited transmission may neglect surface reflectance, also referred to as Fresnel losses or Fresnel reflectance or reflection loss.

With respect to the terms used in this disclosure, the following definitions are provided.

Unless defined otherwise, all technical and scientific terms used herein have the same meaning as commonly understood by one of ordinary skill in the art to which the invention belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula $[***]_n$, is used to depict the number of repeating units in a polymer's chemical formula, the formula should be interpreted to represent the number average molecular weight of the macromolecule.

The term "individual" includes humans and vertebrates.

The term "biomedical device" refers to any article that is designed to be used while either in or on mammalian tissues or fluids, and preferably in or on human tissue or fluids. Examples of these devices include but are not limited to wound dressings, sealants, tissue fillers, drug delivery systems, coatings, adhesion prevention barriers, catheters, implants, stents, and ophthalmic devices such as intraocular lenses and contact lenses. The biomedical devices may be ophthalmic devices, particularly contact lenses, most particularly contact lenses made from silicone hydrogels or conventional hydrogels.

The term "ocular surface" includes the surface and glandular epithelia of the cornea, conjunctiva, lacrimal gland, accessory lacrimal glands, nasolacrimal duct and meibomian gland, and their apical and basal matrices, puncta and adjacent or related structures, including eyelids linked as a functional system by both continuity of epithelia, by innervation, and the endocrine and immune systems.

The term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include soft contact lenses, hard contact lenses, hybrid contact lenses, intraocular lenses, and overlay lenses. The ophthalmic device may comprise a contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet light absorbing, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

The biomedical devices, ophthalmic devices, and lenses of the present invention may be comprised of silicone hydrogels or conventional hydrogels. Silicone hydrogels typically contain at least one hydrophilic monomer and at least one silicone-containing component that are covalently bound to one another in the cured device.

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or cationic polymerization, for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyllactams, N-vinylamides, O-vinylcarbamates, O-vinylcarbonates, and other vinyl groups. Preferably, the free radical polymerizable groups comprise (meth)acrylate, (meth)acrylamide, N-vinyl lactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500, and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxypropyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result and as used herein, di-functional and multi-functional macromers, prepolymers, and crosslinkers may be used interchangeably.

A "silicone-containing component" is a monomer, macromer, prepolymer, cross-linker, initiator, additive, or polymer in the reactive mixture with at least one silicon-oxygen bond, typically in the form of siloxy groups, siloxane groups, carbosiloxane groups, and mixtures thereof.

Examples of silicone-containing components which are useful in this invention may be found in U.S. Pat. Nos. 3,808,178, 4,120,570, 4,136,250, 4,153,641, 4,740,533, 5,034,461, 5,070,215, 5,244,981, 5,314,960, 5,331,067, 5,371,147, 5,760,100, 5,849,811, 5,962,548, 5,965,631, 5,998,498, 6,367,929, 6,822,016, 6,943,203, 6,951,894, 7,052,131, 7,247,692, 7,396,890, 7,461,937, 7,468,398, 7,538,146, 7,553,880, 7,572,841, 7,666,921, 7,691,916, 7,786,185, 7,825,170, 7,915,323, 7,994,356, 8,022,158, 8,163,206, 8,273,802, 8,399,538, 8,415,404, 8,420,711, 8,450,387, 8,487,058, 8,568,626, 8,937,110, 8,937,111, 8,940,812, 8,980,972, 9,056,878, 9,125,808, 9,140,825, 9,156,934, 9,170,349, 9,217,813, 9,244,196, 9,244,197, 9,260,544, 9,297,928, 9,297,929, and European Patent No. 080539. These patents are hereby incorporated by reference in their entireties.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer.

A "polymeric network" is a cross-linked macromolecule that can swell but cannot dissolve in solvents. "Hydrogels" are polymeric networks that swell in water or aqueous solutions, typically absorbing at least 10 weight percent water. "Silicone hydrogels" are hydrogels that are made from at least one silicone-containing component with at least one hydrophilic component. Hydrophilic components may also include non-reactive polymers.

"Conventional hydrogels" refer to polymeric networks made from components without any siloxy, siloxane or carbosiloxane groups. Conventional hydrogels are prepared from reactive mixtures comprising hydrophilic monomers. Examples include 2-hydroxyethyl methacrylate ("HEMA"), N-vinyl pyrrolidone ("NVP"), N, N-dimethylacrylamide ("DMA") or vinyl acetate. U.S. Pat. Nos. 4,436,887, 4,495, 313, 4,889,664, 5,006,622, 5,039459, 5,236,969, 5,270,418, 5,298,533, 5,824,719, 6,420,453, 6,423,761, 6,767,979, 7,934,830, 8,138,290, and 8,389,597 disclose the formation of conventional hydrogels. Commercially available conventional hydrogels include, but are not limited to, etafilcon, genfilcon, hilafilcon, lenefilcon, nesofilcon, omafilcon, polymacon, and vifilcon, including all of their variants.

"Silicone hydrogels" refer to polymeric networks made from at least one hydrophilic component and at least one silicone-containing component. Examples of silicone hydrogels include acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties.

An "interpenetrating polymeric network" comprises two or more networks which are at least partially interlaced on the molecular scale but not covalently bonded to each other and which cannot be separated without braking chemical bonds. A "semi-interpenetrating polymeric network" comprises one or more networks and one or more polymers characterized by some mixing on the molecular level between at least one network and at least one polymer. A mixture of different polymers is a "polymer blend." A semi-interpenetrating network is technically a polymer blend, but in some cases, the polymers are so entangled that they cannot be readily removed.

The terms "reactive mixture" and "reactive monomer mixture" refer to the mixture of components (both reactive and non-reactive) which are mixed together and, when subjected to polymerization conditions, form the conventional or silicone hydrogels of the present invention as well as biomedical devices, ophthalmic devices, and contact lenses made therefrom. The reactive monomer mixture may comprise reactive components such as the monomers, macromers, prepolymers, cross-linkers, and initiators, additives such as wetting agents, polymers, dyes, light absorbing compounds such as UV absorbers, pigments, dyes and photochromic compounds, any of which may be reactive or non-reactive but are capable of being retained within the resulting biomedical device, as well as pharmaceutical and nutraceutical compounds, and any diluents. It will be appreciated that a wide range of additives may be added based upon the biomedical device which is made and its intended use. Concentrations of components of the reactive mixture are expressed as weight percentages of all components in the reactive mixture, excluding diluent. When diluents are used, their concentrations are expressed as weight percentages based upon the amount of all components in the reactive mixture and the diluent.

"Reactive components" are the components in the reactive mixture which become part of the chemical structure of the polymeric network of the resulting hydrogel by covalent bonding, hydrogen bonding, electrostatic interactions, the formation of interpenetrating polymeric networks, or any other means.

The term "silicone hydrogel contact lens" refers to a hydrogel contact lens that is made from at least one silicone-containing compound. Silicone hydrogel contact lenses generally have increased oxygen permeability compared to conventional hydrogels. Silicone hydrogel contact lenses use both their water and polymer content to transmit oxygen to the eye.

The term "multi-functional" refers to a component having two or more polymerizable groups. The term "mono-functional" refers to a component having one polymerizable group.

The terms "halogen" or "halo" indicate fluorine, chlorine, bromine, and iodine.

"Alkyl" refers to an optionally substituted linear or branched alkyl group containing the indicated number of carbon atoms. If no number is indicated, then alkyl (including any optional substituents on alkyl) may contain 1 to 16 carbon atoms. Preferably, the alkyl group contains 1 to 10 carbon atoms, alternatively 1 to 8 carbon atoms, alternatively 1 to 6 carbon atoms, or alternatively 1 to 4 carbon atoms. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, thioalkyl, carbamate, carbonate, halogen, phenyl, benzyl, and combinations thereof. "Alkylene" means a divalent alkyl group, such as $—CH_2—$, $—CH_2CH_2—$, $—CH_2CH_2CH_2—$, $—CH_2CH(CH_3)CH_2—$, and $—CH_2CH_2CH_2CH_2—$.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as $—CF_3—$ or $—CF_2CF_3—$. "Haloalkylene" means a divalent haloalkyl group, such as $—CH_2CF_2—$.

"Cycloalkyl" refers to an optionally substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, thioalkyl, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an optionally substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, thioalkyl, carbamate, carbonate, halo, phenyl, benzyl, and combinations thereof. "Arylene" means a divalent aryl group, for example 1,2-phenylene, 1,3-phenylene, or 1,4-phenylene.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Thioalkyl" means an alkyl group attached to the parent molecule through a sulfur bridge. Examples of thioalkyl groups include, for instance, methylthio, ethylthio, n-propylthio and iso-propylthio. "Aryloxy" refers to an aryl group attached to a parent molecular moiety through an oxygen bridge. Examples include phenoxy. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as $—CH_2CH_2NH—$.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]$_n$—, where n is 2 or more). Each silicon atom in the siloxanyl group is substituted with independently selected $R^A$ groups (where $R^A$ is as defined in formula A options (b)-(i)) to complete their valence.

"Silyl" refers to a structure of formula $R^3Si$— and "siloxy" refers to a structure of formula $R^3Si$—O—, where each R in silyl or siloxy is independently selected from trimethylsiloxy, $C_1$-$C_8$ alkyl (preferably $C_1$-$C_3$ alkyl, more preferably ethyl or methyl), and $C_3$-$C_8$ cycloalkyl.

"Alkyleneoxy" refers to groups of the general formula -(alkylene-O)$_p$— or —(O-alkylene)$_p$-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., HO—[$CH_2CH_2O$]$_p$— or $CH_3O$—[$CH_2CH_2O$]$_p$—). Examples of alkyleneoxy include polyethyleneoxy, polypropyleneoxy, polybutyleneoxy, and poly(ethyleneoxy-co-propyleneoxy).

"Oxaalkylene" refers to an alkylene group as defined above where one or more non-adjacent $CH_2$ groups have been substituted with an oxygen atom, such as —$CH_2CH_2OCH(CH_3)CH_2$—. "Thiaalkylene" refers to an alkylene group as defined above where one or more non-adjacent $CH_2$ groups have been substituted with a sulfur atom, such as —$CH_2CH_2SCH(CH_3)CH_2$—.

The term "linking group" refers to a moiety that links a polymerizable group to the parent molecule. The linking group may be any moiety that is compatible with the compound of which it is a part, and that does not undesirably interfere with the polymerization of the compound, is stable under the polymerization conditions as well as the conditions for the processing and storage of the final product. For instance, the linking group may be a bond, or it may comprise one or more alkylene, haloalkylene, amide, amine, alkyleneamine, carbamate, ester (—$CO_2$—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —$OCF_2$—, —$OCF_2CF_2$—, —$OCF_2CH_2$—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include $C_1$-$C_8$ alkylene (preferably $C_2$-$C_6$ alkylene) and $C_1$-$C_8$ oxaalkylene (preferably $C_2$-$C_6$ oxaalkylene), each of which is optionally substituted with 1 or 2 groups independently selected from hydroxyl and siloxy. Preferred linking groups also include carboxylate, amide, $C_1$-$C_8$ alkylene-carboxylate-$C_1$-$C_8$ alkylene, or $C_1$-$C_8$ alkylene-amide-$C_1$-$C_8$ alkylene.

When the linking group is comprised of combinations of moieties as described above (e.g., alkylene and cycloalkylene), the moieties may be present in any order. For instance, if in Formula E below, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg or Pg) to which the linking group is attached. For example, if in Formula E, L and $L^2$ are indicated as both being alkylene-cycloalkylene, then Rg-L is preferably Rg-alkylene-cycloalkylene- and -$L^2$-Rg is preferably -cycloalkylene-alkylene-Rg.

The term "electron withdrawing group" (EWG) refers to a chemical group which withdraws electron density from the atom or group of atoms to which the electron withdrawing group is attached. Examples of EWGs include, but are not limited to, cyano, amide, ester, keto, or aldehyde. A preferred EWG is cyano (CN).

The terms "high energy radiation absorber," "UV/HEV absorber," or "high energy light absorbing compound" refer to chemical materials that absorb various wavelengths of ultraviolet light, high energy visible light, or both. A material's ability to absorb certain wavelengths of light can be determined by measuring its UV/Vis transmission spectrum. Compounds that exhibit no absorption at a particular wavelength will exhibit substantially 100 percent transmission at that wavelength. Conversely, compounds that completely absorb at a particular wavelength will exhibit substantially 0% transmission at that wavelength. If the amount of a material's transmission is indicated as a percentage for a particular wavelength range, it is to be understood that the material exhibits the percent transmission at all wavelengths within that range.

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

As noted above, one aspect the invention provides an ophthalmic device that is a reaction product of a reactive mixture comprising: one or more polymerizable high energy light absorbing compounds and one or more monomers suitable for making an ophthalmic device, wherein the ophthalmic device transmits: 45 percent or less of light having a wavelength of 280 to 399 nm; at least 1 percent and up to 70 percent of light having a wavelength of 400 to 409 nm; and at least 80 percent of light having a wavelength of 450 to 800 nm. Preferably the ophthalmic device also transmits at least 10 percent and up to 95 percent of light having a wavelength of 410 to 424 nm. Also preferably, the ophthalmic device transmits at least 50 percent of light having a wavelength of 425 to 449 nm. Further preferably, the ophthalmic device transmits 10 percent or less of light having a wavelength of 200 to 279 nm.

Preferably, the transmission of the ophthalmic device at 200 to 279 nm is 5 percent or less or 1 percent or less. Or preferably it is less than 1 percent.

Preferably, the transmission of the ophthalmic device at 280 to 399 nm is 35 percent or less, or 25 percent or less, or 20 percent or less, or 10 percent or less, or 5 percent or less, or 1 percent or less.

Preferably, the transmission of the ophthalmic device at 400 to 409 nm is at least 2 percent, at least 3 percent, or at least 4 percent. Also preferably, the transmission of the ophthalmic device at 400 to 409 nm is up to 60 percent, or up to 50 percent, or up to 40 percent, or up to 30 percent, or up 20 percent.

Preferably, the transmission of the ophthalmic device at 410 to 424 nm is at least 15 percent. Also preferably, the transmission of the ophthalmic device at 410 to 424 nm is up to 85 percent, up to 75 percent, or up 65 percent.

Preferably, the transmission of the ophthalmic device at 425 to 449 nm is at least 60 percent.

Preferably, the transmission of the ophthalmic device at 450 to 800 nm is at least 85 percent.

Preferred ophthalmic devices are contact lenses, more preferably soft hydrogel contact lenses. The foregoing transmission wavelengths and percentages may be measured on various thicknesses of lenses. For example, the center thickness may be from 80 to 100 microns, or from 90 to 100 microns or from 90 to 95 microns. Various concentrations of the one or more polymerizable high energy light absorbing compounds may be used to achieve the foregoing results. For instance, the concentration may be in the range of at least 0.1 percent or at least 2 percent; and up to 10 percent or up to 5 percent, based on the weight percentages of all components in the reactive mixture, excluding diluent. A typical concentration may be in the range of 1 to 5 percent.

The invention also provides UV/HEV absorbing compounds of formula I:

Formula I

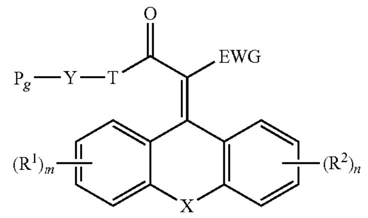

wherein:

m and n are independently 0, 1, 2, 3, or 4;

T is a bond, O, or NR;

X is O, S, NR, SO, or $SO_2$;

Y is a linking group;

$P_g$ is a polymerizable group;

R at each occurrence is independently H, $C_1$-$C_6$ alkyl, cycloalkyl, heterocycloalkyl, aryl, heteroaryl, or Y—$P_g$;

$R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group.

Compounds of formula I preferably contain one or two Y—$P_g$ groups. More preferably, the compounds contain one Y—$P_g$ group.

Formula I-1. Compounds of formula I may include compounds of formula I-1, which are compounds of formula I wherein X is S.

I-2. Compounds of formula I may include compounds of formula I-2, which are compounds of formula I wherein X is O.

I-3. Compounds of formula I may include compounds of formula I-3, which are compounds of formula I wherein X is NR, preferably NH or N-alkyl.

I-4. Compounds of formula I may include compounds of formula I-4, which are compounds of formula I wherein X is SO.

I-5. Compounds of formula I may include compounds of formula I-5, which are compounds of formula I wherein X is $SO_2$.

I-6. Compounds of formulae I, I-1, I-2, I-3, I-4, and I-5 may include compounds of formula I-6, which are compounds of formula I, I-1, I-2, I-3, I-4, or I-5 wherein m and n are independently 0 or 1, or alternatively both are 0.

I-7. Compounds of formulae I, I-1, I-2, I-3, I-4, and I-5 may include compounds of formula I-7, which are compounds of formula I, I-1, I-2, I-3, I-4, or I-5 wherein m is 1 and $R^1$ is $C_1$-$C_6$ alkyl, preferably ethyl or methyl.

I-8. Compounds of formulae I, I-1, I-2, I-3, I-4, I-5, and I-7 may include compounds of formula I-8, which are compounds of formula I, I-1, I-2, I-3, I-4, I-5, or I-7 wherein n is 1 and $R^2$ is $C_1$-$C_6$ alkyl, preferably ethyl or methyl.

I-9. Compounds of formulae I, I-1, I-2, I-3, I-4, I-5, I-6, I-7 and I-8 may include compounds of formula I-9, which are compounds of formula I, I-1, I-2, I-3, I-4, I-5, I-6, I-7 or I-8 wherein R is H, or $C_1$-$C_6$ alkyl. Preferably, R in the group T is H.

I-10. Compounds of formulae I, I-1, I-2, I-3, I-4, I-5, I-6, I-7, I-8, and I-9 may include compounds of formula I-10, which are compounds of formula I, I-1, I-2, I-3, I-4, I-5, I-6, I-7, I-8, or I-9 wherein $P_g$ (a polymerizable group) at each occurrence independently comprises styryl, vinyl carbonate, vinyl ether, vinyl carbamate, N-vinyl lactam, N-vinylamide, (meth)acrylate, or (meth)acrylamide. The polymerizable group allows the compounds of the invention to form covalent bonds when reacted with monomers, crosslinking agents, and other components generally used in making polymeric devices. The compatibility of the compounds with the reactive mixture can be controlled via the selection of the polymerizable group (and the linking group). Preferred polymerizable groups include (meth)acrylate or (meth)acrylamide. A more preferred polymerizable group is methacrylate.

I-11. Compounds of formulae I, I-1, I-2, I-3, I-4, I-5, I-6, I-7, I-8, I-9, and I-10 may include compounds of formula I-11, which are compounds of formula I, I-1, I-2, I-3, I-4, I-5, I-6, I-7, I-8, I-9, or I-10 wherein Y (a linking group) is alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ alkylene-amide-$C_1$-$C_8$ alkylene, and $C_1$-$C_8$ alkylene-amine-$C_1$-$C_8$ alkylene. Particularly preferred is $C_1$-$C_8$ alkylene, especially ethylene ($—CH_2CH_2—$). When T in the compound of formula I is O, it is preferred that the carbon atom of the linking group to which the O is attached be hindered. For instance, if T is O and Y is alkylene, a preferred alkylene is $—C(R^H)_2(CH_2)_x—$, where $R^H$ is independently $C_1$-$C_6$ alkyl (preferably independently methyl or ethyl) and x is from 1 to 5.

I-12. Compounds of formulae I, I-1, I-2, I-3, I-4, I-5, I-6, I-7, I-8, I-9, I-10, and I-11 may include compounds of formula I-12, which are compounds of formula I, I-1, I-2, I-3, I-4, I-5, I-6, I-7, I-8, I-9, I-10, or I-11 wherein T is a bond or is NR (preferably NH).

I-13. Compounds of formulae I, I-1, I-2, I-3, I-4, I-5, I-6, I-7, I-8, I-9, I-10, I-11, and I-12 may include compounds of formula I-13, which are compounds of formula I, I-1, I-2, I-3, I-4, I-5, I-6, I-7, I-8, I-9, I-10, I-11, or I-12 wherein EWG is cyano, amide, ester, keto, or aldehyde. Preferably, EWG is cyano.

Preferred compounds of formula I include compounds of formula II:

Formula II

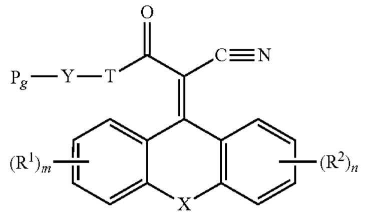

wherein:

m and n are independently 0, 1, 2, 3, or 4;

T is a bond, O, or NR;

X is O, S, NR, SO, or $SO_2$;

Y is a linking group;

$P_g$ is a polymerizable group;

R at each occurrence is independently H, $C_1$-$C_6$ alkyl, cycloalkyl, heterocycloalkyl, aryl, heteroaryl, or Y—$P_g$; and $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring. Compounds of formula I preferably contain one or two Y—$P_g$ groups. More preferably, the compounds contain one Y—$P_g$ group.

Formula II-1. Compounds of formula II may include compounds of formula II-1, which are compounds of formula II wherein X is S.

II-2. Compounds of formula II may include compounds of formula II-2, which are compounds of formula II wherein X is O.

II-3. Compounds of formula II may include compounds of formula II-3, which are compounds of formula II wherein X is NR, preferably NH or N-alkyl.

II-4. Compounds of formula II may include compounds of formula II-4, which are compounds of formula II wherein X is SO.

II-5. Compounds of formula II may include compounds of formula II-5, which are compounds of formula II wherein X is $SO_2$.

II-6. Compounds of formulae II, II-1, II-2, II-3, II-4, and II-5 may include compounds of formula II-6, which are compounds of formula II, II-1, II-2, II-3, II-4, or II-5 wherein m and n are independently 0 or 1, or alternatively both are 0.

II-7. Compounds of formulae II, II-1, II-2, II-3, II-4, and II-5 may include compounds of formula II-7, which are compounds of formula II, II-1, II-2, II-3, II-4, or II-5 wherein m is 1 and $R^1$ is $C_1$-$C_6$ alkyl, preferably ethyl or methyl.

II-8. Compounds of formulae II, II-1, II-2, II-3, II-4, II-5, and II-7 may include compounds of formula II-8, which are compounds of formula II, II-1, II-2, II-3, II-4, II-5, or II-7 wherein n is 1 and $R^2$ is $C_1$-$C_6$ alkyl, preferably ethyl or methyl.

II-9. Compounds of formulae II, II-1, II-2, II-3, II-4, II-5, II-6, II-7 and II-8 may include compounds of formula II-9, which are compounds of formula II, II-1, II-2, II-3, II-4, II-5, II-6, II-7 or II-8 wherein R is H, or $C_1$-$C_6$ alkyl. Preferably, R in the group T is H.

II-10. Compounds of formulae II, II-1, II-2, II-3, II-4, II-5, II-6, II-7, II-8, and II-9 may include compounds of formula II-10, which are compounds of formula II, II-1, II-2, II-3, II-4, II-5, II-6, II-7, II-8, or II-9 wherein $P_g$ (a polymerizable group) at each occurrence independently comprises styryl, vinyl carbonate, vinyl ether, vinyl carbamate, N-vinyl lactam, N-vinylamide, (meth)acrylate, or (meth)acrylamide. The polymerizable group allows the compounds of the invention to form covalent bonds when reacted with monomers, crosslinking agents, and other components generally used in making polymeric devices. The compatibility of the compounds with the reactive mixture can be controlled via the selection of the polymerizable group (and the linking group). Preferred polymerizable groups include (meth)acrylate or (meth)acrylamide. A more preferred polymerizable group is methacrylate.

II-11. Compounds of formulae II, II-1, II-2, II-3, II-4, II-5, II-6, II-7, II-8, II-9, and II-10 may include compounds of formula II-11, which are compounds of formula II, II-1, II-2, II-3, II-4, II-5, II-6, II-7, II-8, II-9, or II-10 wherein Y (a linking group) is alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ alkylene-amide-$C_1$-$C_8$ alkylene, and $C_1$-$C_8$ alkylene-amine-$C_1$-$C_8$ alkylene. Particularly preferred is $C_1$-$C_8$ alkylene, especially ethylene (—$CH_2CH_2$—). When T in the compound of formula II is O, it is preferred that the carbon atom of the linking group to which the O is attached be hindered. For instance, if T is O and Y is alkylene, a preferred alkylene is —$C(R^H)_2(CH_2)_x$—, where $R^H$ is independently $C_1$-$C_6$ alkyl (preferably independently methyl or ethyl) and x is from 1 to 5.

II-12. Compounds of formulae II, II-1, II-2, II-3, II-4, II-5, II-6, II-7, II-8, II-9, II-10, and II-11 may include compounds of formula II-12, which are compounds of formula II, II-1, II-2, II-3, II-4, II-5, II-6, II-7, II-8, II-9, II-10, or II-11 wherein T is a bond or is NR (preferably NH).

Preferred compounds of formula I and formula II include compounds of formula III:

Formula III

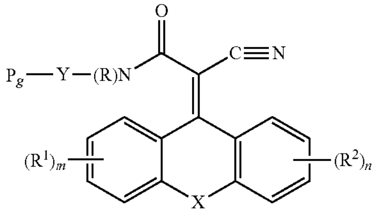

wherein:

m and n are independently 0, 1, 2, 3, or 4;

X is O, S, NR, SO, or $SO_2$;

Y is a linking group;

$P_g$ is a polymerizable group;

R at each occurrence is independently H, $C_1$-$C_6$ alkyl, cycloalkyl, heterocycloalkyl, aryl, heteroaryl, or Y—$P_g$; and $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring. Compounds of formula II preferably contain one or two Y—$P_g$ groups. More preferably, the compounds contain one Y—$P_g$ group.

Formula III-1. Compounds of formula III may include compounds of formula III-1, which are compounds of formula III wherein X is S.

III-2. Compounds of formula III may include compounds of formula III-2, which are compounds of formula III wherein X is O.

III-3. Compounds of formula III may include compounds of formula III-3, which are compounds of formula III wherein X is NR, preferably NH or N-alkyl.

III-4. Compounds of formula III may include compounds of formula III-4, which are compounds of formula III wherein X is SO.

III-5. Compounds of formula III may include compounds of formula III-5, which are compounds of formula III wherein X is 502.

III-6. Compounds of formulae III, III-1, III-2, III-3, III-4, and III-5 may include compounds of formula III-6, which are compounds of formula III, III-1, III-2, III-3, III-4, or III-5 wherein m and n are independently 0 or 1, or alternatively both are 0.

III-7. Compounds of formulae III, III-1, III-2, III-3, III-4, and III-5 may include compounds of formula III-7, which are compounds of formula III, III-1, III-2, III-3, III-4, or III-5 wherein m is 1 and $R^1$ is $C_1$-$C_6$ alkyl, preferably ethyl or methyl.

III-8. Compounds of formulae III, III-1, III-2, III-3, III-4, III-5, and III-7 may include compounds of formula III-8, which are compounds of formula III, III-1, III-2, III-3, III-4, III-5, or III-7 wherein n is 1 and $R^2$ is $C_1$-$C_6$ alkyl, preferably ethyl or methyl.

III-9. Compounds of formulae III, III-1, III-2, III-3, III-4, III-5, III-6, III-7 and III-8 may include compounds of formula III-9, which are compounds of formula III, III-1, III-2, III-3, III-4, III-5, III-6, III-7 or III-8 wherein R at each occurrence is independently H, or $C_1$-$C_6$ alkyl. Preferably, R at each occurrence is H. Preferably R in the group T is H III-10. Compounds of formulae III, III-1, III-2, III-3, III-4, III-5, III-6, III-7, III-8, and III-9 may include compounds of formula III-10, which are compounds of formula III, III-1, III-2, III-3, III-4, III-5, III-6, III-7, III-8, or III-9 wherein Pg (a polymerizable group) at each occurrence independently comprises styryl, vinyl carbonate, vinyl ether, vinyl carbamate, N-vinyl lactam, N-vinylamide, (meth)acrylate, or (meth)acrylamide. The polymerizable group allows the compounds of the invention to form covalent bonds when reacted with monomers, crosslinking agents, and other components generally used in making polymeric devices. The compatibility of the compounds with the reactive mixture can be controlled via the selection of the polymerizable group (and the linking group). Preferred polymerizable groups include (meth)acrylate or (meth)acrylamide. A more preferred polymerizable group is methacrylate.

III-11. Compounds of formulae III, III-1, III-2, III-3, III-4, III-5, III-6, III-7, III-8, III-9, and III-10 may include compounds of formula III-11, which are compounds of formula III, III-1, III-2, III-3, III-4, III-5, III-6, III-7, III-8, III-9, or III-10 wherein Y (a linking group) is alkylene, cycloalkylene, heterocycloalkylene, arylene (e.g., phenylene), heteroarylene, oxaalkylene, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ alkylene-amide-$C_1$-$C_8$ alkylene, and $C_1$-$C_8$ alkylene-amine-$C_1$-$C_8$ alkylene. Particularly preferred is $C_1$-$C_8$ alkylene, especially ethylene (—$CH_2CH_2$—).

Specific examples of compounds of formula I include, but are not limited to, the compounds shown in Table 1.

TABLE 1

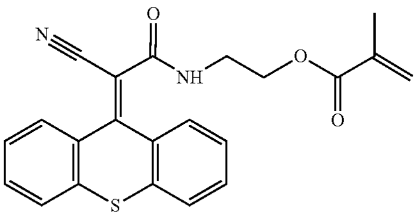 [SMILES: C=C(C)C(=O)OCCNC(=O)C(C#N)=C1c2ccccc2Sc2ccccc21]

2-(2-cyano-2-(9H-thioxanthen-9-ylidene)acetamido)ethyl methacrylate

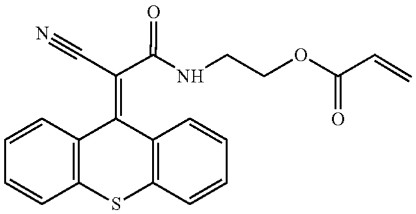

2-(2-cyano-2-(9H-thioxanthen-9-ylidene)acetamido)ethyl acrylate

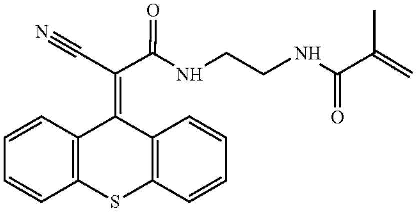 [SMILES: C=C(C)C(=O)NCCNC(=O)C(C#N)=C1c2ccccc2Sc2ccccc21]

N-(2-(2-cyano-2-(9H-thioxanthen-9-ylidene)acetamido)ethyl)methacrylamide

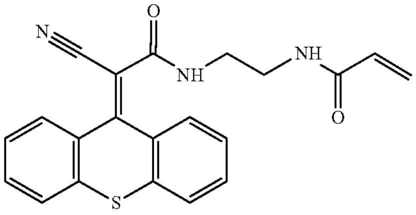 [SMILES: C=CC(=O)NCCNC(=O)C(C#N)=C1c2ccccc2Sc2ccccc21]

N-(2-(2-cyano-2-(9H-thioxanthen-9-ylidene)acetamido)ethyl)acrylamide

TABLE 1-continued

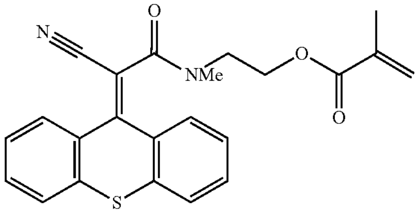 [SMILES: C=C(C)C(=O)OCCN(C)C(=O)C(C#N)=C1c2ccccc2Sc2ccccc21]

2-(2-cyano-N-methyl-2-(9H-thioxanthen-9-ylidene)acetamido)ethyl methacrylate

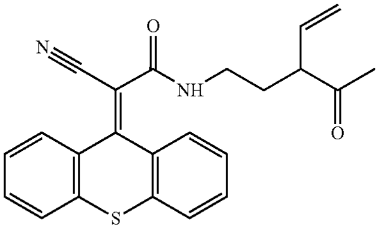 [SMILES: C=CC(CCNC(=O)C(C#N)=C1c2ccccc2Sc2ccccc21)C(C)=O]

2-cyano-2-(9H-thioxanthen-9-ylidene)-N-(2-(N-vinylacetamido)ethyl)acetamide

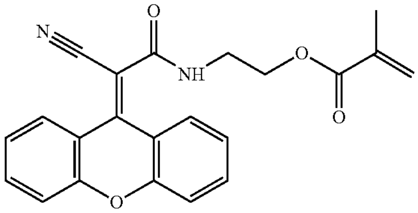

2-(2-cyano-2-(9H-xanthen-9-ylidene)acetamido)ethyl methacrylate

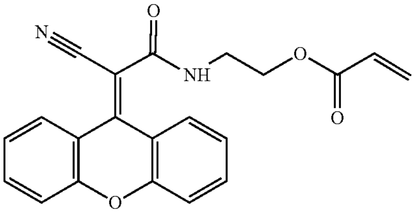 [SMILES: C=CC(=O)OCCNC(=O)C(C#N)=C1c2ccccc2Oc2ccccc21]

2-(2-cyano-2-(9H-xanthen-9-ylidene)acetamido)ethyl acrylate

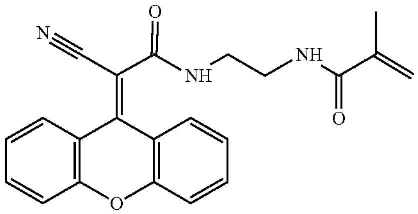 [SMILES: C=C(C)C(=O)NCCNC(=O)C(C#N)=C1c2ccccc2Oc2ccccc21]

N-(2-(2-cyano-2-(9H-xanthen-9-ylidene)acetamido)ethyl)methacrylamide

TABLE 1-continued

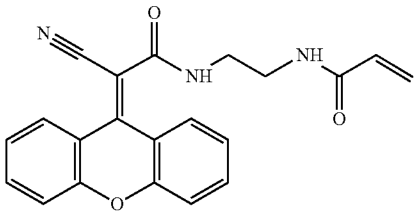 [SMILES: C=CC(=O)NCCNC(=O)C(C#N)=C1c2ccccc2Oc2ccccc21]

N-(2-(2-cyano-2-(9H-xanthen-9-ylidene)acetamido)ethyl)acrylamide

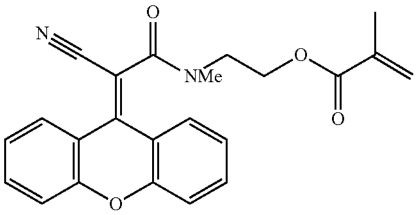

2-(2-cyano-N-methyl-2-(9H-xanthen-9-ylidene)acetamido)ethyl methacrylate

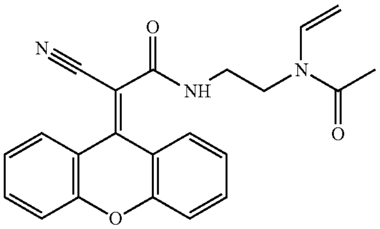 [SMILES: C=CN(CCNC(=O)C(C#N)=C1c2ccccc2Oc2ccccc21)C(C)=O]

2-cyano-N-(2-(N-vinylacetamido)ethyl)-2-(9H-xanthen-9-ylidene)acetamide

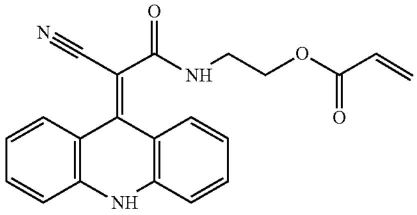 [SMILES: C=CC(=O)OCCNC(=O)C(C#N)=C1c2ccccc2Nc2ccccc21]

2-(2-(acridin-9(10H)-ylidene)-2-cyanoacetamido)ethyl acrylate

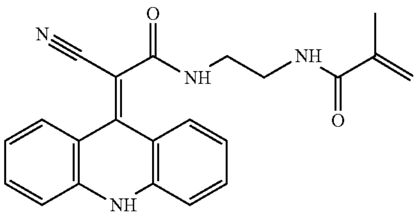 [SMILES: C=C(C)C(=O)NCCNC(=O)C(C#N)=C1c2ccccc2Nc2ccccc21]

N-(2-(2-(acridin-9(10H)-ylidene)-2-cyanoacetamido)ethyl)methacrylamide

TABLE 1-continued

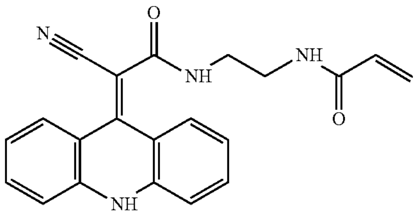 [SMILES: C=CC(=O)NCCNC(=O)C(C#N)=C1c2ccccc2Nc2ccccc21]

N-(2-(2-(acridin-9(10H)-ylidene)-2-cyanoacetamido) ethyl)acrylamide

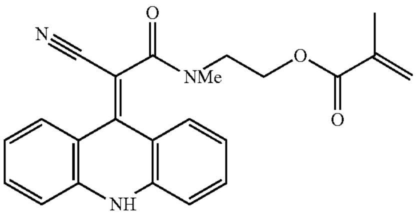 [SMILES: C=C(C)C(=O)OCCN(C)C(=O)C(C#N)=C1c2ccccc2Nc2ccccc21]

2-(2-(acridin-9(10H)-ylidene)-2-cyano-N-methylacetamido)ethyl methacrylate

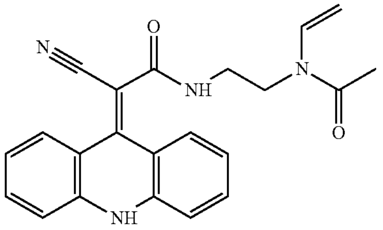 [SMILES: C=CN(CCNC(=O)C(C#N)=C1c2ccccc2Nc2ccccc21)C(C)=O]

2-(acridin-9(10H)-ylidene)-2-cyano-N-(2-(N-vinylacetamido)ethyl)acetamide

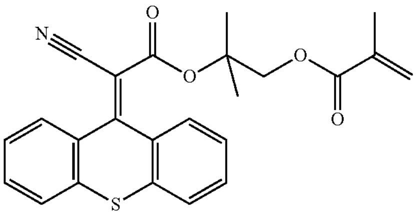 [SMILES: C=C(C)C(=O)OCC(C)(C)OC(=O)C(C#N)=C1c2ccccc2Sc2ccccc21]

2-(2-cyano-2-(9H-thioxanthen-9-ylidene)acetamido)-2-methylpropyl methacrylate

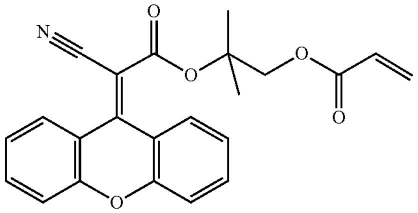 [SMILES: C=CC(=O)OCC(C)(C)OC(=O)C(C#N)=C1c2ccccc2Oc2ccccc21]

2-(2-cyano-2-(9H-xanthen-9-ylidene)acetoxy)-2-methylpropyl acrylate

TABLE 1-continued

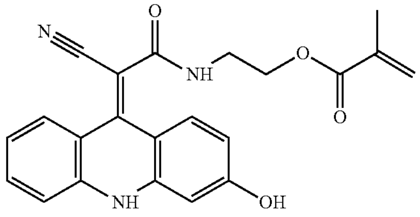 [SMILES: C=C(C)C(=O)OCCNC(=O)/C(C#N)=C1/c2ccccc2Nc2cc(O)ccc21]

(Z)-2-(2-cyano-2-(3-hydroxyacridin-9(10H)-ylidene)acetamido)ethyl methacrylate

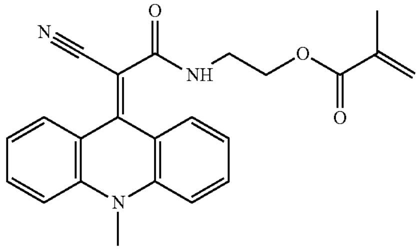 [SMILES: C=C(C)C(=O)OCCNC(=O)C(C#N)=C1c2ccccc2N(C)c2ccccc21]

2-(2-cyano-2-(10-methylacridin-9(10H)-ylidene)acetamido)ethyl methacrylate

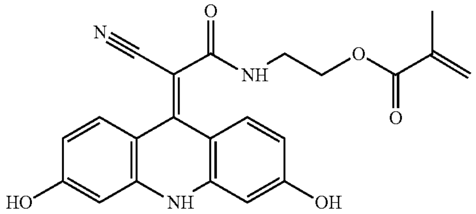 [SMILES: C=C(C)C(=O)OCCNC(=O)C(C#N)=C1c2ccc(O)cc2Nc2cc(O)ccc21]

2-(2-cyano-2-(3,6-dihydroxyacridin-9(10H)-ylidene)acetamido)ethyl methacrylate

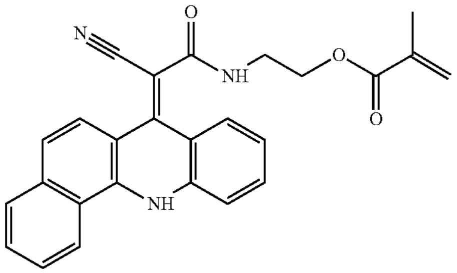 [SMILES: C=C(C)C(=O)OCCNC(=O)/C(C#N)=C1\c2ccccc2Nc2c1ccc1ccccc21]

(E)-2-(2-(7H-benzo[c]xanthen-7-ylidene)-2-cyanoacetamido)ethyl methacrylate

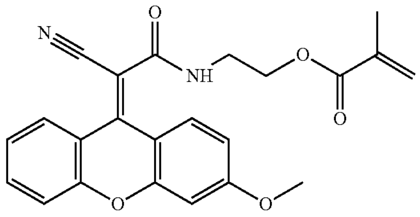 [SMILES: C=C(C)C(=O)OCCNC(=O)/C(C#N)=C1/c2ccccc2Oc2cc(OC)ccc21]

(Z)-2-(2-cyano-2-(3-methoxy-9H-xanthen-9-ylidene)acetamido)ethyl methacrylate

TABLE 1-continued

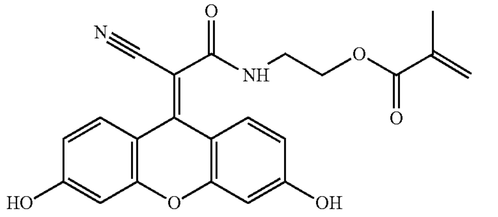 [SMILES: C=C(C)C(=O)OCCNC(=O)C(C#N)=C1c2ccc(O)cc2Oc2cc(O)ccc21]

2-(2-cyano-2-(3,6-dihydroxy-9H-xanthen-9-ylidene)acetamido)ethyl methacrylate

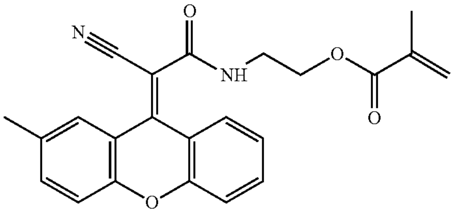 [SMILES: C=C(C)C(=O)OCCNC(=O)/C(C#N)=C1\c2ccccc2Oc2ccc(C)cc21]

(E)-2-(2-cyano-2-(2-methyl-9H-xanthen-9-ylidene)acetamido)ethyl methacrylate

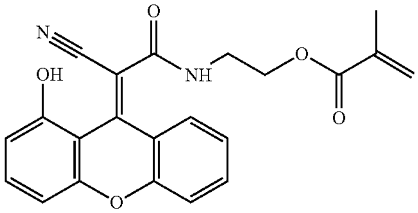 [SMILES: C=C(C)C(=O)OCCNC(=O)/C(C#N)=C1\c2ccccc2Oc2cccc(O)c21]

(E)-2-(2-cyano-2-(1-hydroxy-9H-xanthen-9-ylidene)acetamido)ethyl methacrylate

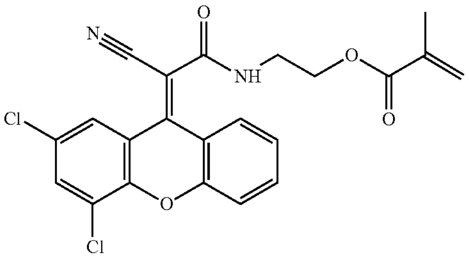 [SMILES: C=C(C)C(=O)OCCNC(=O)/C(C#N)=C1\c2ccccc2Oc2c(Cl)cc(Cl)cc21]

(E)-2-(2-cyano-2-(2,4-dichloro-9H-thioxanthen-9-ylidene)acetamido)ethyl methacrylate

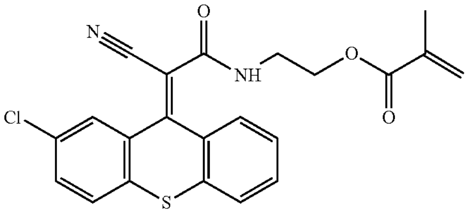 [SMILES: C=C(C)C(=O)OCCNC(=O)/C(C#N)=C1\c2ccccc2Sc2ccc(Cl)cc21]

(E)-2-(2-(2-chloro-9H-thioxanthen-9-ylidene)-2-cyanoacetamido)ethyl methacrylate TABLE 1-continued

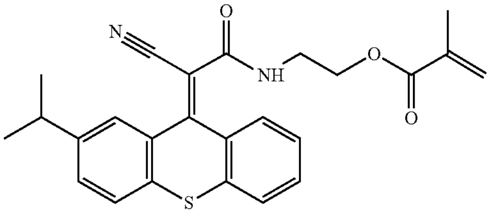 [SMILES: C=C(C)C(=O)OCCNC(=O)/C(C#N)=C1\c2ccccc2Sc2ccc(C(C)C)cc21]

(E)-2-(2-cyano-2-(2-isopropyl-9H-thioxanthen-9-ylidene)acetamido)ethyl methacrylate

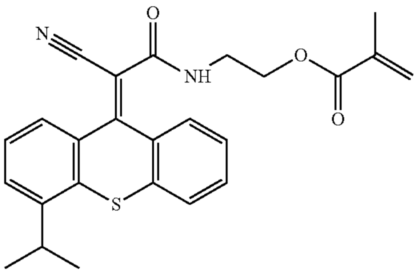 [SMILES: C=C(C)C(=O)OCCNC(=O)/C(C#N)=C1\c2ccccc2Sc2c1cccc2C(C)C]

(E)-2-(2-cyano-2-(4-isopropyl-9H-thioxanthen-9-ylidene)acetamido)ethyl methacrylate

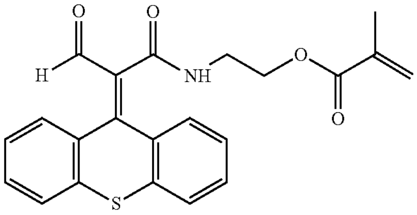 [SMILES: C=C(C)C(=O)OCCNC(=O)C(C=O)=C1c2ccccc2Sc2ccccc21]

2-(3-oxo-2-(9H-thioxanthen-9-ylidene)propanamido)ethyl methacrylate

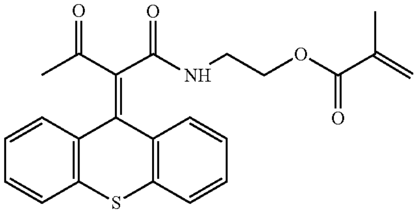 [SMILES: C=C(C)C(=O)OCCNC(=O)C(C(C)=O)=C1c2ccccc2Sc2ccccc21]

2-(3-oxo-2-(9H-thioxanthen-9-ylidene)butanamido)ethyl methacrylate

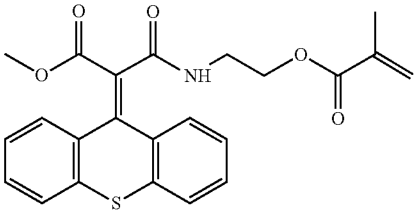 [SMILES: C=C(C)C(=O)OCCNC(=O)C(C(=O)OC)=C1c2ccccc2Sc2ccccc21]

2-(3-methoxy-3-oxo-2-(9H-thioxanthen-9-ylidene)propanamido)ethyl methacrylate

TABLE 1-continued

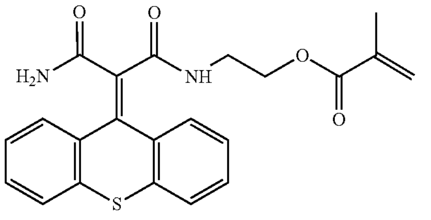 [SMILES: C=C(C)C(=O)OCCNC(=O)C(C(N)=O)=C1c2ccccc2Sc2ccccc21]

2-(3-amino-3-oxo-2-(9H-thioxanthen-9-ylidene)propanamido)ethyl methacrylate
2-(2-cyano-2-(10,10-dioxido-9H-thioxanthen-9-ylidene)acetamido)ethyl methacrylate
N-(2-(2-cyano-2-(10-methylacridin-9(10H)ylidene)acetamido)ethyl) methacrylamide
2-(2-cyano-2-(9H-thioxanthen-9-ylidene)acetoxy)ethyl methacrylate Compounds of the invention can be selected to provide targeted absorption of UV and/or high energy visible light. Such targeting may be achieved, for example, through selection of the hetero atom of the core tricyclic structure (X in formula I). For instance, compounds of formula I-1 (the heteroatom is sulfur) may absorb HEV light. On the other hands, compounds of formula I-2 (the heteroatom is oxygen) may absorb UV light and some HEV light although to a lesser extent than formula I-1 compounds.

Additional tuning of the absorption characteristics for a given X in the compounds of formula I may be provided by adding or varying the substituents $R^1$ and $R^2$ to, for instance, obtain bathochromic or hypsochromic shifts. Electron donating substituents may, for example, may cause red shifts to the UV-VIS absorption spectrum, while electron withdrawing groups may cause blue shifts; the magnitude of these shifts may depend on the electron donating or withdrawing ability, and the position, of the substituent. For example, an alkoxy substituent may result in a smaller red shift than, for instance, an amino or thioalkyl group at the same carbon center.

Preferred X groups in the compounds of the invention are S, O, and NR, more preferably S and O. However, additional oxidation states of sulfur such as sulfoxide and sulfone may also provide a means to modify UV-VIS spectra of the compounds. Sulfoxide and sulfone have reduced electron density on the sulfur atom and may be used to create hypsochromic (blue) shifted spectra.

Compounds of formula I may be used in combination with other absorbing compounds to provide desirable absorption characteristics. For example, preferred compositions may comprise a compound of formula I-1 (X is S) and a second compound that absorbs UV. The second compound may, for example, also be a compound of formula I that absorbs in the UV region (such as compounds of formula I-2 (X is O)), or it may be another UV absorbing compound. Suitable UV absorbing compounds are known in the art, and fall into several classes which include, but are not limited to, benzophenones, benzotriazoles, triazines, substituted acrylonitriles, salicyclic acid derivatives, benzoic acid derivatives, cinnamic acid derivatives, chalcone derivatives, dypnone derivatives, crotonic acid derivatives, or any mixtures thereof. A preferred class of UV absorbing compound is benzotriazoles, such as Norbloc (2-(2'-hydroxy-5-methacrylyloxyethylphenyl)-2H-benzotriazole).

A particularly preferred composition comprises 2-(2-cyano-2-(9H-thioxanthen-9-ylidene)acetamido)ethyl methacrylate and 2-(2-cyano-2-(9H-xanthen-9-ylidene)acetamido)ethyl methacrylate. Another preferred composition comprises 2-(2-cyano-2-(9H-thioxanthen-9-ylidene)acetamido)ethyl methacrylate and 2-(2'-hydroxy-5-methacrylyloxyethylphenyl)-2H-benzotriazole. A further preferred composition comprises N-(2-(2-cyano-2-(10-methylacridin-9(10H)ylidene)acetamido)ethyl) methacrylamide.

Compounds of formula I may be prepared by those skilled in the art using literature methods. By way of example, various compounds of formula I where the EWG is cyano may be prepared as shown in Scheme 1 and the associated description. Exemplary reagents and procedures for these reactions appear in the working examples.

Scheme 1

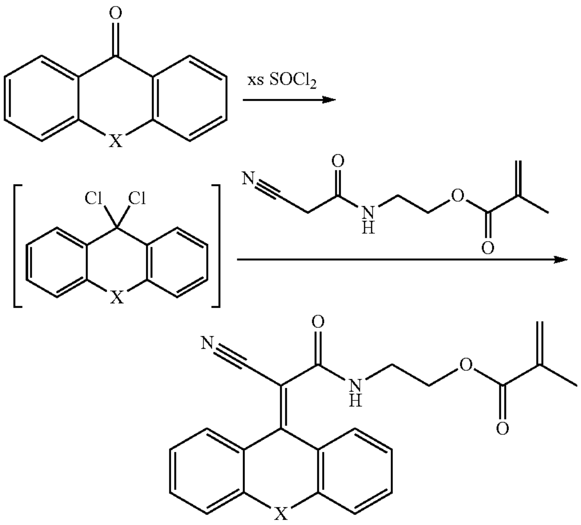

Scheme 1 shows a method for preparing exemplary compounds of the invention. Thus, the carbonyl moiety of the starting material is converted to a reactive dihalide intermediate, which is further reacted with the active methylene compound without further purification or isolation. The reaction mixture is protected from air and moisture until completion of the reaction with the cyanomethyl amide derivative. Other compounds of the invention may be prepared by those skilled in the art using analogous procedures to those shown in Scheme 1 with appropriate substitution of reagents.

High energy light absorbing compounds, such as the compounds of formula I, may be included in reactive mixtures to form various products, including biomedical devices and ophthalmic devices. Generally, the high energy light absorbing compounds can be present in any amount up to the limit of their solubility. For instance, the compounds may be present in an amount in the range of about 0.1% to about 10% by weight, or from about 0.5 to about 5% by weight, or from about 0.75% to about 4% by weight. The upper limit is typically determined by the solubility of the compound with other co-monomers and or diluents in the reactive monomer mix.

Preferably, the high energy light absorbing compounds of the invention are included in ophthalmic devices. A variety of ophthalmic devices may be prepared, including hard contact lenses, soft contact lenses, corneal onlays, corneal inlays, intraocular lenses, or overlay lenses. Preferably, the ophthalmic device is a soft contact lens, which may be made from conventional or silicone hydrogel formulations.

Ophthalmic devices of the invention comprise a free radical reaction product of a reactive mixture containing one or more polymerizable high energy light absorbing compounds, such as compounds of formula I, one or more monomers suitable for making the desired ophthalmic device (also referred to herein as device forming monomers or hydrogel forming monomers), and optional components. Thus, the reactive mixture may, for example, include, in addition to a polymerizable high energy light absorbing compound as described above, one or more of: hydrophilic components, hydrophobic components, silicone-containing components, wetting agents such as polyamides, crosslinking agents, and further components such as diluents and initiators.

Hydrophilic Components

Examples of suitable families of hydrophilic monomers include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof.

Non-limiting examples of hydrophilic (meth)acrylate and (meth)acrylamide monomers include: acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl) (meth)acrylamide, N,N-bis(2-hydroxyethyl) (meth)acrylamide, N-(2-hydroxypropyl) (meth)acrylamide, N,N-bis(2-hydroxypropyl) (meth)acrylamide, N-(3-hydroxypropyl) (meth)acrylamide, N-(2-hydroxybutyl) (meth) acrylamide, N-(3-hydroxybutyl) (meth)acrylamide, N-(4-hydroxybutyl) (meth)acrylamide, 2-aminoethyl (meth) acrylate, 3-aminopropyl (meth)acrylate, 2-aminopropyl (meth)acrylate, N-2-aminoethyl (meth)acrylamides), N-3-aminopropyl (meth)acrylamide, N-2-aminopropyl (meth) acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile, and mixtures thereof.

Hydrophilic monomers may also be ionic, including anionic, cationic, zwitterions, betaines, and mixtures thereof. Non-limiting examples of such charged monomers include (meth)acrylic acid, N-[(ethenyloxy)carbonyl]-β-alanine (VINAL), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl) amino]propyl]-3-sulfo-, inner salt (SBT), 3,5-Dioxa-8-aza-4-phosphaundec-10-en-1-aminium, 4-hydroxy-N,N,N-trimethyl-9-oxo-, inner salt, 4-oxide (9CI) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), and methacryloyloxy)propyl) dimethylammonio)propane-1-sulfonate (MAPDAPS).

Non-limiting examples of hydrophilic N-vinyl lactam and N-vinyl amide monomers include: N-vinyl pyrrolidone (NVP), N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, N-vinyl acetamide (NVA), N-vinyl-N-methylacetamide (VMA), N-vinyl-N-ethyl acetamide, N-vinyl-N-ethyl formamide, N-vinyl formamide, N-vinyl-N-methylpropionamide, N-vinyl-N-methyl-2-methylpropionamide, N-vinyl-2-methylpropionamide, N-vinyl-N,N'-dimethylurea, 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-N-propyl-3-methylene-2-pyrrolidone, 1-N-propyl-5-methylene-2-pyrrolidone, 1-isopropyl-3-methylene-2-pyrrolidone, 1-isopropyl-5-methylene-2-pyrrolidone, N-vinyl-N-ethyl acetamide, N-vinyl-N-ethyl formamide, N-vinyl formamide, N-vinyl isopropylamide, N-vinyl caprolactam, N-vinylimidazole, and mixtures thereof Non-limiting examples of hydrophilic O-vinyl carbamates and O-vinyl carbonates monomers include N-2-hydroxyethyl vinyl carbamate and N-carboxy-ß-alanine N-vinyl ester. Further examples of hydrophilic vinyl carbonate or vinyl carbamate monomers are disclosed in U.S. Pat. No. 5,070,215. Hydrophilic oxazolone monomers are disclosed in U.S. Pat. No. 4,910,277.

Other hydrophilic vinyl compounds include ethylene glycol vinyl ether (EGVE), di(ethylene glycol) vinyl ether (DEGVE), allyl alcohol, and 2-ethyl oxazoline.

The hydrophilic monomers may also be macromers or prepolymers of linear or branched poly(ethylene glycol), poly(propylene glycol), or statistically random or block copolymers of ethylene oxide and propylene oxide, having polymerizable moieties such as (meth)acrylates, styrenes, vinyl ethers, (meth)acrylamides, N-vinylamides, and the like. The macromers of these polyethers have one polymerizable group; the prepolymers may have two or more polymerizable groups.

The preferred hydrophilic monomers of the present invention are DMA, NVP, HEMA, VMA, NVA, and mixtures thereof. Preferred hydrophilic monomers include mixtures of DMA and HEMA. Other suitable hydrophilic monomers will be apparent to one skilled in the art.

Generally, there are no particular restrictions with respect to the amount of the hydrophilic monomer present in the reactive monomer mixture. The amount of the hydrophilic monomers may be selected based upon the desired characteristics of the resulting hydrogel, including water content, clarity, wettability, protein uptake, and the like. Wettability may be measured by contact angle, and desirable contact angles are less than about 100°, less than about 80°, and less than about 60°. The hydrophilic monomer may be present in an amount in the range of, for instance, about 0.1 to about 100 weight percent, alternatively in the range of about 1 to about 80 weight percent, alternatively about 5 to about 65 weight percent, alternatively in the range of about 40 to about 60 weight percent, or alternatively about 55 to about 60 weight percent, based on the total weight of the reactive components in the reactive monomer mixture.

Silicone-Containing Components

Silicone-containing components suitable for use in the invention comprise one or more polymerizable compounds, where each compound independently comprises at least one polymerizable group, at least one siloxane group, and one or more linking groups connecting the polymerizable group(s) to the siloxane group(s). The silicone-containing components may, for instance, contain from 1 to 220 siloxane repeat units, such as the groups defined below. The silicone-containing component may also contain at least one fluorine atom.

The silicone-containing component may comprise: one or more polymerizable groups as defined above; one or more optionally repeating siloxane units; and one or more linking groups connecting the polymerizable groups to the siloxane units. The silicone-containing component may comprise: one or more polymerizable groups that are independently a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing; one or more optionally repeating siloxane units; and one or more linking groups connecting the polymerizable groups to the siloxane units.

The silicone-containing component may comprise: one or more polymerizable groups that are independently a (meth) acrylate, a (meth)acrylamide, an N-vinyl lactam, an N-vinylamide, a styryl, or mixtures of the foregoing; one or more optionally repeating siloxane units; and one or more linking groups connecting the polymerizable groups to the siloxane units.

The silicone-containing component may comprise: one or more polymerizable groups that are independently a (meth) acrylate, a (meth)acrylamide, or mixtures of the foregoing; one or more optionally repeating siloxane units; and one or more linking groups connecting the polymerizable groups to the siloxane units.

Formula A. The silicone-containing component may comprise one or more polymerizable compounds of Formula A:

Formula A

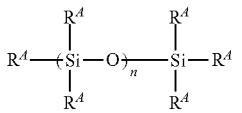

wherein:

at least one $R^A$ is a group of formula $R_g$-L- wherein $R_g$ is a polymerizable group and L is a linking group, and the remaining $R^A$ are each independently:

(a) $R_g$-L-, (b) $C_1$-$C_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof, (c) $C_3$-$C_{12}$ cycloalkyl optionally substituted with one or more alkyl, hydroxy, amino, amido, oxa, carbonyl, alkoxy, amido, carbamate, carbonate, halo, phenyl, benzyl, or combinations thereof, (d) a $C_6$-$C_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof, (e) halo, (f) alkoxy, cyclic alkoxy, or aryloxy, (g) siloxy, (h) alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or (i) a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^A$ substituents and if different $R^A$ substituents are present, the n groups may be in random or block configuration.

In Formula A, three $R^A$ may each comprise a polymerizable group, alternatively two $R^A$ may each comprise a polymerizable group, or alternatively one $R^A$ may comprise a polymerizable group.

Formula B. The silicone-containing component of formula A may be a mono-functional polymerizable compound of formula B:

Formula B

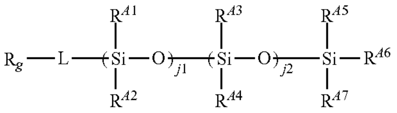

wherein:

Rg is a polymerizable group;

L is a linking group;

j1 and j2 are each independently whole numbers from 0 to 220, provided that the sum of j1 and j2 is from 1 to 220;

$R^{A1}$, $R^{A2}$, $R^{A3}$, $R^{A4}$, $R^{A5}$, and $R^{A7}$ are independently at each occurrence $C_1$-$C_6$ alkyl, $C_3$-$C_{12}$ cycloalkyl, $C_1$-$C_6$ alkoxy, $C_4$-$C_{12}$ cyclic alkoxy, alkoxy-alkyleneoxy-alkyl, aryl (e.g., phenyl), aryl-alkyl (e.g., benzyl), haloalkyl (e.g., partially or fully fluorinated alkyl), siloxy, fluoro, or combinations thereof, wherein each alkyl in the foregoing groups is optionally substituted with one or more hydroxy, amino, amido, oxa, carboxy, alkyl carboxy, carbonyl, alkoxy, carbamate, carbonate, halo, phenyl, or benzyl, each cycloalkyl is optionally substituted with one or more alkyl, hydroxy, amino, amido, oxa, carbonyl, alkoxy, carbamate, carbonate, halo, phenyl, or benzyl and each aryl is optionally substituted with one or more alkyl, hydroxy, amino, amido, oxa, carboxy, alkyl carboxy, carbonyl, alkoxy, carbamate, carbonate, halo, phenyl, or benzyl; and $R^{A6}$ is siloxy, $C_1$-$C_8$ alkyl (e.g., $C_1$-$C_4$ alkyl, or butyl, or methyl), or aryl (e.g., phenyl), wherein alkyl and aryl may optionally be substituted with one or more fluorine atoms.

Formula B-1. Compounds of formula B may include compounds of formula B-1, which are compounds of formula B wherein j1 is zero and j2 is from 1 to 220, or j2 is from 1 to 100, or j2 is from 1 to 50, or j2 is from 1 to 20, or j2 is from 1 to 5, or j2 is 1.

B-2. Compounds of formula B may include compounds of formula B-2, which are compounds of formula B wherein j1 and j2 are independently from 4 to 100, or from 4 to 20, or from 4 to 10, or from 24 to 100, or from 10 to 100.

B-3. Compounds of formulae B, B-1, and B-2 may include compounds of formula B-3, which are compounds of formula B, B-1, or B-2 wherein $R^{A1}$, $R^{A2}$, $R^{A3}$, and $R^{A4}$ are independently at each occurrence $C_1$-$C_6$ alkyl or siloxy. Preferred alkyl are $C_1$-$C_3$ alkyl, or more preferably, methyl. Preferred siloxy is trimethylsiloxy.

B-4. Compounds of formulae B, B-1, B-2, and B-3 may include compounds of formula B-4, which are compounds of formula B, B-1, B-2, or B-3 wherein $R^{A5}$ and $R^{A7}$ are independently alkoxy-alkyleneoxy-alkyl, preferably they are independently a methoxy capped polyethyleneoxyalkyl of formula $CH_3O—[CH_2CH_2O]_p—CH_2CH_2CH_2$, wherein p is a whole number from 1 to 50.

B-5. Compounds of formulae B, B-1, B-2, and B-3 may include compounds of formula B-5, which are compounds of formula B, B-1, B-2, or B-3 wherein $R^{A5}$ and $R^{A7}$ are independently siloxy, such as trimethylsiloxy.

B-6. Compounds of formulae B, B-1, B-2, and B-3 may include compounds of formula B-6, which are compounds of formula B, B-1, B-2, or B-3 wherein $R^{A5}$ and $R^{A7}$ are independently $C_1$-$C_6$ alkyl, alternatively $C_1$-$C_4$ alkyl, or alternatively, butyl or methyl.

B-7. Compounds of formulae B, B-1, B-2, B-3, B-4, B-5, and B-6 may include compounds of formula B-7, which are compounds of formula B, B-1, B-2, B-3, B-4, B-5, or B-6 wherein $R^{A6}$ is $C_1$-$C_8$ alkyl, preferably $C_1$-$C_6$ alkyl, more preferably $C_1$-$C_4$ alkyl (for example methyl, ethyl, n-propyl, or n-butyl). More preferably $R^{A6}$ is n-butyl.

B-8. Compounds of formulae B, B-1, B-2, B-3, B-4, B-5, B-6, and B-7, may include compounds of formula B-8, which are compounds of formula B, B-1, B-2, B-3, B-4, B-5, B-6, or B-7 wherein Rg comprises styryl, vinyl carbonate, vinyl ether, vinyl carbamate, N-vinyl lactam, N-vinylamide, (meth)acrylate, or (meth)acrylamide. Preferably, Rg comprises (meth)acrylate, (meth)acrylamide, or styryl. More preferably, Rg comprises (meth)acrylate or (meth)acrylamide. When Rg is (meth)acrylamide, the nitrogen group may be substituted with $R^{A9}$, wherein $R^{A9}$ is H, $C_1$-$C_8$ alkyl (preferably $C_1$-$C_4$ alkyl, such as n-butyl, n-propyl, methyl or ethyl), or $C_3$-$C_8$ cycloalkyl (preferably $C_5$-$C_6$ cycloalkyl), wherein alkyl and cycloalkyl are optionally substituted with one or more groups independently selected from hydroxyl, amide, ether, silyl (e.g., trimethylsilyl), siloxy (e.g., trimethylsiloxy), alkyl-siloxanyl (where alkyl is itself optionally substituted with fluoro), aryl-siloxanyl (where aryl is itself optionally substituted with fluoro), and silyl-oxaalkylene-(where the oxaalkylene is itself optionally substituted with hydroxyl).

B-9. Compounds of formulae B, B-1, B-2, B-3, B-4, B-5, B-6, B-7, and B-8 may include compounds of formula B-9, which are compounds of formula B, B-1, B-2, B-3, B-4, B-5, B-6, B-7, or B-8 wherein the linking group comprises alkylene (preferably $C_1$-$C_4$ alkylene), cycloalkylene (preferably $C_5$-$C_6$ cycloalkylene), alkyleneoxy (preferably ethyleneoxy), haloalkyleneoxy (preferably haloethyleneoxy), amide, oxaalkylene (preferably containing 3 to 6 carbon atoms), siloxanyl, alkylenesiloxanyl, carbamate, alkyleneamine (preferably $C_1$-$C_6$ alkyleneamine), or combinations of two or more thereof, wherein the linking group is optionally substituted with one or more substituents independently selected from alkyl, hydroxyl, ether, amine, carbonyl, siloxy, and carbamate.

B-10. Compounds of formulae B, B-1, B-2, B-3, B-4, B-5, B-6, B-7, B-8, and B-9 may include compounds of formula B-10, which are compounds of formula B, B-1, B-2, B-3, B-4, B-5, B-6, B-7, B-8, or B-9 wherein the linking group is alkylene-siloxanyl-alkylene-alkyleneoxy-, or alkylene-siloxanyl-alkylene-[alkyleneoxy-alkylene-siloxanyl]$_q$-alkyleneoxy-, where q is from 1 to 50.

B-11. Compounds of formulae B, B-1, B-2, B-3, B-4, B-5, B-6, B-7, B-8, and B-9 may include compounds of formula B-11, which are compounds of formula B, B-1, B-2, B-3, B-4, B-5, B-6, B-7, B-8, or B-9 wherein the linking group is $C_1$-$C_6$ alkylene, preferably $C_1$-$C_3$ alkylene, more preferably n-propylene.

B-12. Compounds of formulae B, B-1, B-2, B-3, B-4, B-5, B-6, B-7, B-8, and B-9 may include compounds of formula B-12, which are compounds of formula B, B-1, B-2, B-3, B-4, B-5, B-6, B-7, B-8, or B-9 wherein the linking group is alkylene-carbamate-oxaalkylene. Preferably, the linking group is $CH_2CH_2N(H)—C(=O)—O—CH_2CH_2—O—CH_2CH_2CH_2$.

B-13. Compounds of formulae B, B-1, B-2, B-3, B-4, B-5, B-6, B-7, B-8, and B-9 may include compounds of formula B-13, which are compounds of formula B, B-1, B-2, B-3, B-4, B-5, B-6, B-7, B-8, or B-9 wherein the linking group is oxaalkylene. Preferably, the linking group is $CH_2CH_2—O—CH_2CH_2CH_2$.

B-14. Compounds of formulae B, B-1, B-2, B-3, B-4, B-5, B-6, B-7, B-8, and B-9 may include compounds of formula B-14, which are compounds of formula B, B-1, B-2, B-3, B-4, B-5, B-6, B-7, B-8, or B-9 wherein the linking group is alkylene-[siloxanyl-alkylene]$_q$-, where q is from 1 to 50. An example of such a linking group is: $—(CH_2)_3—[Si(CH_3)_2—O—Si(CH_3)_2—(CH_2)_2]_q—$.

B-15. Compounds of formulae B, B-1, B-2, B-3, B-4, B-5, B-6, B-7, B-8, and B-9 may include compounds of formula B-15, which are compounds of formula B, B-1, B-2, B-3, B-4, B-5, B-6, B-7, B-8, or B-9 wherein the linking group is alkyleneoxy-carbamate-alkylene-cycloalkylene-carbamate-oxaalkylene, wherein cycloalkylene is optionally substituted with or 1, 2, or 3 independently selected alkyl groups (preferably $C_1$-$C_3$ alkyl, more preferably methyl). An example of such a linking group is $—[OCH_2CH_2]_q—OC(=O)—NH—CH_2$-[1,3-cyclohexylene]-$NHC(=O)O—CH_2CH_2—O—CH_2CH_2—$, wherein the cyclohexylene is substituted at the 1 and 5 positions with 3 methyl groups.

B-16. Compounds of formulae B, B-1, B-2, B-3, B-4, B-5, B-6, B-7, B-8, and B-9 may include compounds of formula B-16, which are compounds of formula B, B-1, B-2, B-3, B-4, B-5, B-6, B-7, B-8, or B-9 wherein Rg comprises styryl and the linking group is a bond or is alkyleneoxy, wherein each alkylene in alkyleneoxy is independently optionally substituted with hydroxyl. An example of such a linking group is $—O—(CH_2)_3—$. Another example of such a linking group is $—O—CH_2CH(OH)CH_2—O—(CH_2)_3—$.

B-17. Compounds of formulae B, B-1, B-2, B-3, B-4, B-5, B-6, B-7, B-8, and B-9 may include compounds of formula B-17, which are compounds of formula B, B-1, B-2, B-3, B-4, B-5, B-6, B-7, B-8, or B-9 wherein Rg comprises styryl and the linking group is alkyleneamine. An example of such a linking group is $—NH—(CH_2)_3—$.

B-18. Compounds of formulae B, B-1, B-2, B-3, B-4, B-5, B-6, B-7, B-8, and B-9 may include compounds of formula B-18, which are compounds of formula B, B-1, B-2, B-3, B-4, B-5, B-6, B-7, B-8, or B-9 wherein the linking group is oxaalkylene optionally substituted with hydroxyl, siloxy, or silyl-alkyleneoxy (where the alkyleneoxy is itself optionally substituted with hydroxyl). An example of such a linking group is $—CH_2CH(G)CH_2—O—(CH_2)_3—$, wherein G is hydroxyl. In another example, G is $R^3SiO—$ wherein two R groups are trimethylsiloxy and the third is $C_1$-$C_8$ alkyl (preferably $C_1$-$C_3$ alkyl, more preferably methyl) or the third is $C_3$-$C_8$ cycloalkyl. In a further example, G is $R^3Si—(CH_2)_3—O—CH_2CH(OH)CH_2—O—$, wherein two R groups are trimethylsiloxy and the third is $C_1$-$C_8$ alkyl (preferably $C_1$-$C_3$ alkyl, more preferably methyl) or $C_3$-$C_5$ cycloalkyl. In a still further example, G is a polymerizable group, such as (meth)acrylate. Such compounds may function as crosslinkers.

B-19. Compounds of formulae B, B-1, B-2, B-3, B-4, B-5, B-6, B-7, B-8, and B-9 may include compounds of formula B-19, which are compounds of formula B, B-1, B-2, B-3, B-4, B-5, B-6, B-7, B-8, or B-9 wherein Rg comprises styryl and the linking group is amine-oxaalkylene optionally substituted with hydroxyl. An example of such a linking group is $—NH—CH_2CH(OH)CH_2—O—(CH_2)_3—$.

B-20. Compounds of formulae B, B-1, B-2, B-3, B-4, B-5, B-6, B-7, B-8, and B-9 may include compounds of formula B-20, which are compounds of formula B, B-1, B-2, B-3, B-4, B-5, B-6, B-7, B-8, or B-9 wherein Rg comprises styryl and the linking group is alkyleneoxy-carbamate-oxaalkylene. An example of such a linking group is $—O—(CH_2)_2—N(H)C(=O)O—(CH_2)_2—O—(CH_2)_3—$.

B-21. Compounds of formulae B, B-1, B-2, B-3, B-4, B-5, B-6, B-7, B-8, and B-9 may include compounds of formula B-21, which are compounds of formula B, B-1, B-2, B-3, B-4, B-5, B-6, B-7, B-8, or B-9 wherein the linking group is alkylene-carbamate-oxaalkylene. An example of such a linking group is $—(CH_2)_2—N(H)C(=O)O—(CH_2)_2—O—(CH_2)_3—$.

Formula C. Silicone-containing components of formulae A, B, B-1, B-2, B-3, B-4, B-5, B-6, B-7, B-8, B-9, B-10, B-11, B-12, B-13, B-14, B-15, B-18, and B-21 may include compounds of formula C, which are compounds of formula A, B, B-1, B-2, B-3, B-4, B-5, B-6, B-7, B-8, B-9, B-10, B-11, B-12, B-13, B-14, B-15, B-18, or B-21 having the structure:

Formula C

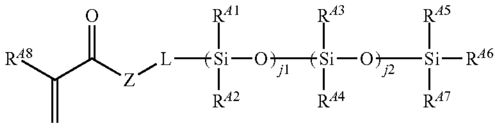

wherein $R^{A8}$ is hydrogen or methyl;

Z is O, S, or $N(R^{A9})$; and

L, j1, j2, $R^{A1}$, $R^{A2}$, $R^{A3}$, $R^{A4}$, $R^{A5}$, $R^{A6}$, $R^{A7}$, and $R^{A9}$ are as defined in formula B or its various sub-formulae (e.g., B-1, B-2, etc.).

C-1. Compounds of formula C may include (meth)acrylates of formula C-1, which are compounds of formula C wherein Z is O.

C-2. Compounds of formula C may include (meth)acrylamides of formula C-2, which are compounds of formula C wherein Z is $N(R^{A9})$, and $R^{A9}$ is H.

C-3. Compounds of formulae C may include (meth) acrylamides of formula C-3, which are compounds of formula C wherein Z is $N(R^{A9})$, and $R^{A9}$ is $C_1$-$C_8$ alkyl that is unsubstituted or is optionally substituted as indicated above. Examples of $R^{A9}$ include $CH_3$, $—CH_2CH(OH)CH_2(OH)$, $—(CH_2)_3$-siloxanyl, $—(CH_2)_3—SiR_3$, and $—CH_2CH(OH)CH_2—O—(CH_2)_3—SiR_3$ where each R in the foregoing groups is independently selected from trimethylsiloxy, $C_1$-$C_8$ alkyl (preferably $C_1$-$C_3$ alkyl, more preferably methyl), and $C_3$-$C_8$ cycloalkyl. Further examples of $R^{A9}$ include: $—(CH_2)_3—Si(Me)(SiMe_3)_2$, and $—(CH_2)_3—Si(Me_2)—[O—SiMe_2]_{1-10}$-$CH_3$.

Formula D. Compounds of formula C may include compounds of formula D:

Formula D

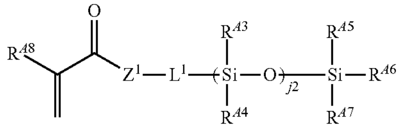

wherein $R^{A5}$ is hydrogen or methyl;

$Z^1$ is O or $N(R^{A9})$;

$L^1$ is alkylene containing 1 to 8 carbon atoms, or oxaalkylene containing 3 to 10 carbon atoms, wherein $L^1$ is optionally substituted with hydroxyl; and j2, $R^{A3}$, $R^{A4}$, $R^{A5}$, $R^{A6}$, $R^{A7}$, and $R^{A9}$ are as defined above in formula B or its various sub-formulae (e.g., B-1, B-2, etc.).

D-1. Compounds of formula D may include compounds of formula D-1, which are compounds of formula D wherein $L^1$ is $C_2$-$C_5$ alkylene optionally substituted with hydroxyl. Preferably $L^1$ is n-propylene optionally substituted with hydroxyl.

D-2. Compounds of formula D may include compounds of formula D-2, which are compounds of formula D wherein $L^1$ is oxaalkylene containing 4 to 8 carbon atoms optionally substituted with hydroxyl. Preferably $L^1$ is oxaalkylene containing five or six carbon atoms optionally substituted with hydroxyl. Examples include $—(CH_2)_2—O—(CH_2)_3—$, and $—CH_2CH(OH)CH_2—O—(CH_2)_3—$.

D-3. Compounds of formulae D, D-1, and D-2 may include compounds of formula D-3, which are compounds of formula D, D-1, or D-2 wherein $Z^1$ is O.

D-4. Compounds of formulae D, D-1, and D-2 may include compounds of formula D-4, which are compounds of formula D, D-1, or D-2 wherein $Z^1$ is $N(R^{A9})$, and $R^{A9}$ is H.

D-5. Compounds of formulae D, D-1, and D-2 may include compounds of formula D-5, which are compounds of formula D, D-1, or D-2 wherein $Z^1$ is $N(R^{A9})$, and $R^{A9}$ is $C_1$-$C_4$ alkyl optionally substituted with 1 or 2 substituents selected from hydroxyl, siloxy, and $C_1$-$C_6$ alkyl-siloxanyl-.

D-6. Compounds of formulae D, D-1, D-2, D-3, D-4, and D-5 may include compounds of formula D-6, which are compounds of formula D, D-1, D-2, D-3, D-4, or D-5 wherein j2 is 1.

D-7. Compounds of formulae D, D-1, D-2, D-3, D-4, and D-5 may include compounds of formula D-7, which are compounds of formula D, D-1, D-2, D-3, D-4, or D-5 wherein j2 is from 2 to 220, or from 2 to 100, or from 10 to 100, or from 24 to 100, or from 4 to 20, or from 4 to 10.

D-8. Compounds of formulae D, D-1, D-2, D-3, D-4, D-5, D-6, and D-7 may include compounds of formula D-8, which are compounds of formula D, D-1, D-2, D-3, D-4, D-5, D-6, or D-7 wherein $R^{A3}$, $R^{A4}$, $R^{A5}$, $R^{A6}$, and $R^{A7}$ are independently $C_1$-$C_6$ alkyl or siloxy. Preferably $R^{A3}$, $R^{A4}$, $R^{A5}$, $R^{A6}$, and $R^{A7}$ are independently selected from methyl, ethyl, n-propyl, n-butyl, and trimethylsiloxy. More preferably, $R^{A3}$, $R^{A4}$, $R^{A5}$, $R^{A6}$, and $R^{A7}$ are independently selected from methyl, n-butyl, and trimethylsiloxy.

D-9. Compounds of formulae D, D-1, D-2, D-3, D-4, D-5, D-6, and D-7 may include compounds of formula D-9, which are compounds of formula D, D-1, D-2, D-3, D-4, D-5, D-6, or D-7 wherein $R^{A3}$ and $R^{A4}$ are independently $C_1$-$C_6$ alkyl (e.g., methyl or ethyl) or siloxy (e.g., trimethylsiloxy), and $R^{A5}$, $R^{A6}$, and $R^{A7}$ are independently $C_1$-$C_6$ alkyl (e.g., methyl, ethyl, n-propyl, or n-butyl).

Formula E. The silicone-containing component for use in the invention may comprise a multi-functional silicone-containing component. Thus, for example, the silicone-containing component of formula A may comprise a bifunctional material of formula E:

Formula E

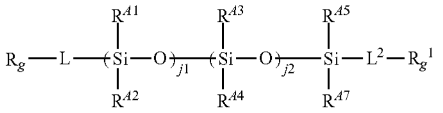

wherein

Rg, L, j1, j2, $R^{A1}$, $R^{A2}$, $R^{A3}$, $R^{A4}$, $R^{A5}$, and $R^{A7}$ are as defined above for formula B or its various sub-formulae (e.g., B-1, B-2, etc.);

$L^2$ is a linking group; and $Rg^1$ is a polymerizable group.

E-1. Compounds of formula E may include compounds of formula E-1, which are compounds of formula E wherein Rg and $Rg^1$ are each a vinyl carbonate of structure $CH_2$═CH—O—C(═O)—O— or structure $CH_2$═C($CH_3$)—O—C(═O)—O—.

E-2. Compounds of formula E may include compounds of formula E-2, which are compounds of formula E wherein Rg and $Rg^1$ are each (meth)acrylate.

E-3. Compounds of formula E may include compounds of formula E-3, which are compounds of formula E wherein Rg and $Rg^1$ are each (meth)acrylamide, wherein the nitrogen group may be substituted with $R^{A9}$ (wherein $R^{A9}$ is as defined above).

E-4. Suitable compounds of formulae E, E-1, E-2, and E-3 include compounds of formula E-4, which are compounds of formula E, E-1, E-2, or E-3 wherein j1 is zero and j2 is from 1 to 220, or j2 is from 1 to 100, or j2 is from 1 to 50, or j2 is from 1 to 20.

E-5. Suitable compounds of formulae E, E-1, E-2, and E-3 include compounds of formula E-5, which are compounds of formula E, E-1, E-2, or E-3, wherein j1 and j2 are independently from 4 to 100.

E-6. Suitable compounds of formulae E, E-1, E-2, E-3, E-4, and E-5 include compounds of formula E-6, which are compounds of formula E, E-1, E-2, E-3, E-4, or E-5 wherein $R^{A1}$, $R^{A2}$, $R^{A3}$, $R^{A4}$, and $R^{A5}$ are independently at each occurrence $C_1$-$C_6$ alkyl, preferably they are independently $C_1$-$C_3$ alkyl, or preferably, each is methyl.

E-7. Suitable compounds of formulae E, E-1, E-2, E-3, E-4, E-5, and E-6 include compounds of formula E-7, which are compounds of formula E, E-1, E-2, E-3, E-4, E-5, or E-6 wherein $R^{A7}$ is alkoxy-alkyleneoxy-alkyl, preferably it is a methoxy capped polyethyleneoxyalkyl of formula $CH_3O$—$[CH_2CH_2O]_p$—$CH_2CH_2CH_2$, wherein p is a whole number from 1 to 50, or from 1 to 30, or from 1 to 10, or from 6 to 10.

E-8. Suitable compounds of formulae E, E-1, E-2, E-3, E-4, E-5, E-6, and E-7 include compounds of formula E-8, which are compounds of formula E, E-1, E-2, E-3, E-4, E-5, E-6, or E-7 wherein L comprises alkylene, carbamate, siloxanyl, cycloalkylene, amide, haloalkyleneoxy, oxaalkylene, or combinations of two or more thereof, wherein the linking group is optionally substituted with one or more substituents independently selected from alkyl, hydroxyl, ether, amine, carbonyl, and carbamate.

E-9. Suitable compounds of formulae E, E-1, E-2, E-3, E-4, E-5, E-6, E-7, and E-8 include compounds of formula E-9, which are compounds of formula E, E-1, E-2, E-3, E-4, E-5, E-6, E-7, or E-8 wherein $L^2$ comprises alkylene, carbamate, siloxanyl, cycloalkylene, amide, haloalkyleneoxy, oxaalkylene, or combinations of two or more thereof, wherein the linking group is optionally substituted with one or more substituents independently selected from alkyl, hydroxyl, ether, amine, carbonyl, and carbamate.

Examples of silicone-containing components suitable for use in the invention include, but are not limited to, compounds listed in Table 2. Where the compounds in Table 2 contain polysiloxane groups, the number of SiO repeat units in such compounds, unless otherwise indicated, is preferably from 3 to 100, more preferably from 3 to 40, or still more preferably from 3 to 20.

TABLE 2

| | |
|---|---|
| 1 | mono-methacryloxypropyl terminated mono-n-butyl terminated polydimethylsiloxanes (mPDMS) (preferably containing from 3 to 15 SiO repeating units) |
| 2 | mono-acryloxypropyl terminated mono-n-butyl terminated polydimethylsiloxane |
| 3 | mono(meth)acryloxypropyl terminated mono-n-methyl terminated polydimethylsiloxane |
| 4 | mono(meth)acryloxypropyl terminated mono-n-butyl terminated polydiethylsiloxane |
| 5 | mono(meth)acryloxypropyl terminated mono-n-methyl terminated polydiethylsiloxane |
| 6 | mono(meth)acrylamidoalkylpolydialkylsiloxanes |
| 7 | mono(meth)acryloxyalkyl terminated mono-alkyl polydiarylsiloxanes |
| 8 | 3-methacryloxypropyltris(trimethylsiloxy)silane (TRIS) |
| 9 | 3-methacryloxypropylbis(trimethylsiloxy)methylsilane |
| 10 | 3-methacryloxypropylpentamethyl disiloxane |
| 11 | mono(meth)acrylamidoalkylpolydialkylsiloxanes |
| 12 | mono(meth)acrylamidoalkyl polydimethylsiloxanes |
| 13 | N-(2,3-dihydroxypropane)-N'-(propyl tetra(dimethylsiloxy) dimethylbutylsilane)acrylamide |
| 14 | N-[3-tris(trimethylsiloxy)silyl]-propyl acrylamide (TRIS-Am) |
| 15 | 2-hydroxy-3-[3-methyl-3,3-di(trimethylsiloxy)silylpropoxy]-propyl methacrylate (SiMAA) |
| 16 | 2-hydroxy-3-methacryloxypropyloxypropyl-tris(trimethylsiloxy)silane |

TABLE 2-continued
17 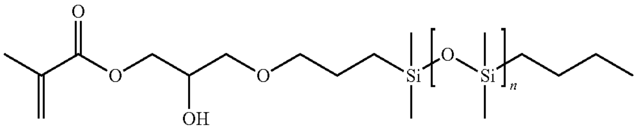
mono-(2-hydroxy-3-methacryloxypropyloxy)-propyl terminated mono-n-butyl terminated polydimethylsiloxanes (OH-mPDMS) (containing from 4 to 30, or from 4 to 20, or from 4 to 15 SiO repeat units)
18 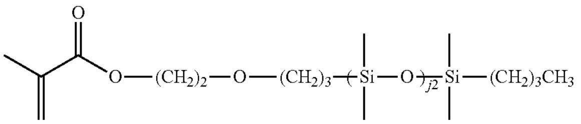
19 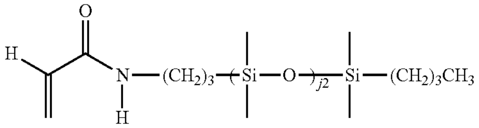
20 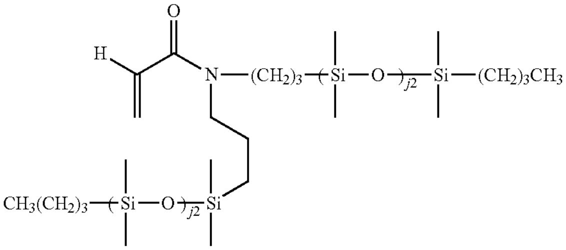
21 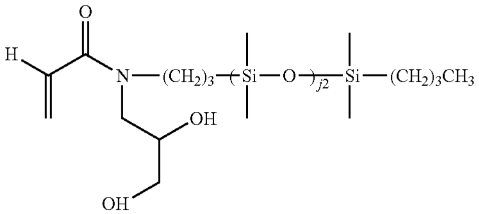
22 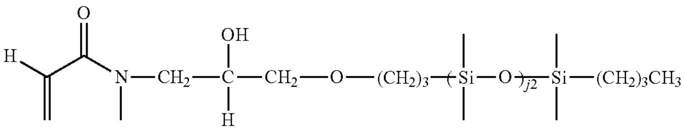
23 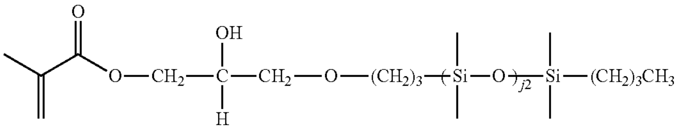
24 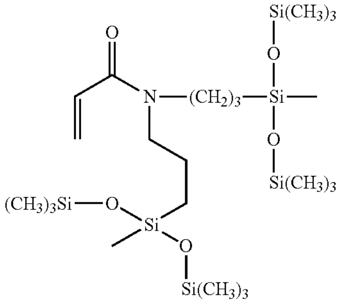

Additional non-limiting examples of suitable silicone-containing components are listed in Table 3. Unless otherwise indicated, j2 where applicable is preferably from 1 to 100, more preferably from 3 to 40, or still more preferably from 3 to 15. In compounds containing j1 and j2, the sum of j1 and j2 is preferably from 2 to 100, more preferably from 3 to 40, or still more preferably from 3 to 15.

TABLE 3

| | |
|---|---|
| 25 | 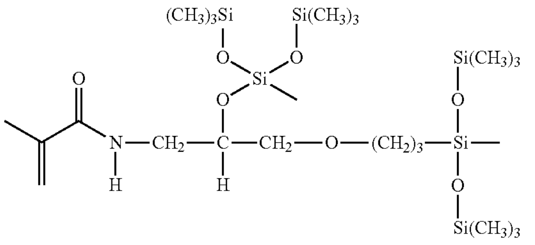 |
| 26 | 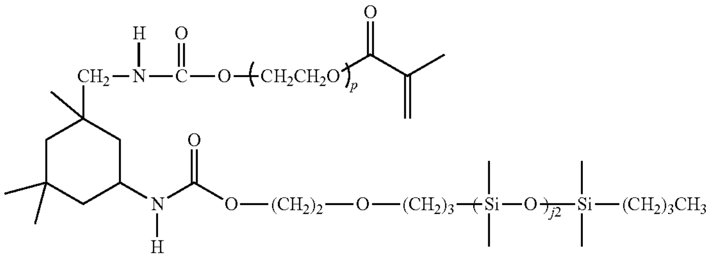<br>p is 1 to 10 |
| 27 | 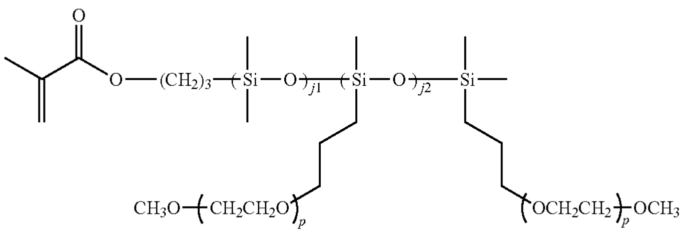<br>p is 5-10 |
| 28 | 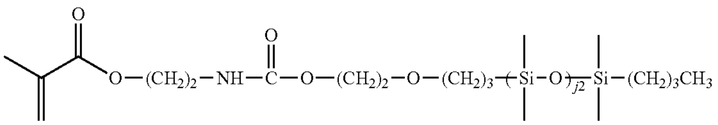 |
| 29 | 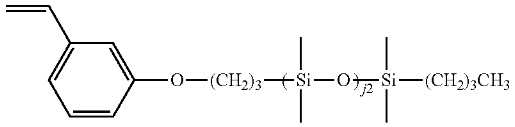 |
| 30 | 1,3-bis[4-(vinyloxycarbonyloxy)but-1-yl]tetramethyl-disiloxane |
| 31 | 3-(vinyloxycarbonylthio)propyl-[tris(trimethylsiloxy)silane] |
| 32 | 3-[tris(trimethylsiloxy)silyl]propyl ally carbamate |
| 33 | 3-[tris(trimethylsiloxy)silyl]propyl vinyl carbamate |
| 34 | tris(trimethylsiloxy)silylstyrene (Styryl-TRIS) |

TABLE 3-continued

| | |
|---|---|
| 35 | 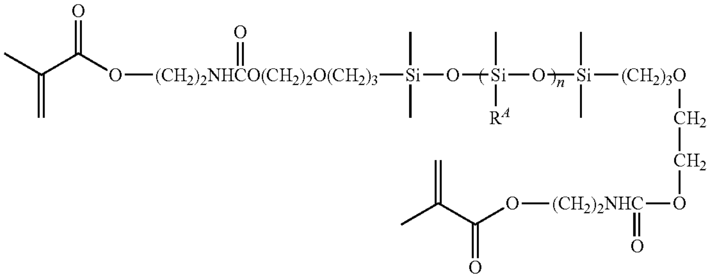<br>$R^A = CH_3$ (a) or $CH_2CH_2CF_3$ (b) or $CH_2$-$(CH_2)_2$-$[OCH_2CH_2]_{1-10}$-$OCH_3$ (c); a + b + c = n |
| 36 | 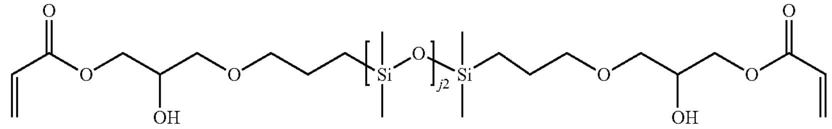 |
| 37 | 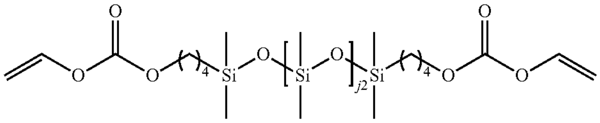 |
| 38 | 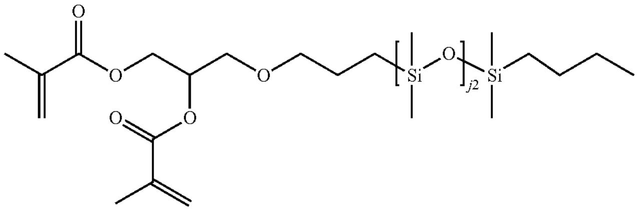 |
| 39 | 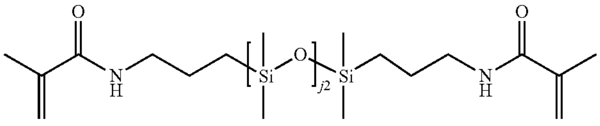 |
| 40 | 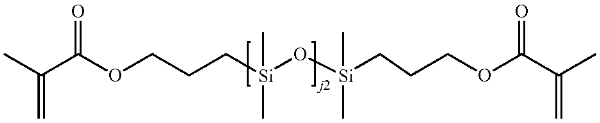 |
| 41 | 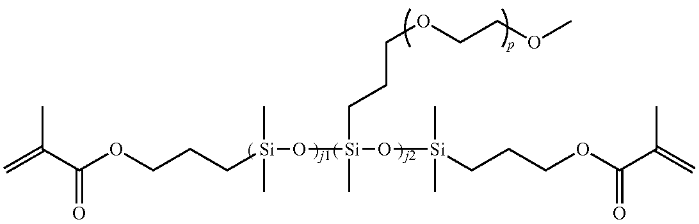<br>j1 = 80-90<br>j2 = 5-6<br>p = 7-8 |

Mixtures of silicone-containing components may be used. By way of example, suitable mixtures may include, but are not limited to: a mixture of mono-(2-hydroxy-3-methacryloxypropyloxy)-propyl terminated mono-n-butyl terminated polydimethylsiloxane (OH-mPDMS) having different molecular weights, such as a mixture of OH-mPDMS containing 4 and 15 SiO repeat units; a mixture of OH-mPDMS with different molecular weights (e.g., containing 4 and 15 repeat SiO repeat units) together with a silicone based crosslinker, such as bis-3-acryloxy-2-hydroxypropyloxypropyl polydimethylsiloxane (ac-PDMS); a mixture of 2-hydroxy-3-[3-methyl-3,3-di(trimethylsiloxy)silylpropoxy]-propyl methacrylate (SiMAA) and mono-methacryloxypropyl terminated mono-n-butyl terminated polydimethylsiloxane (mPDMS), such as mPDMS 1000.

Silicone-containing components for use in the invention may have an average molecular weight of from about 400 to about 4000 daltons.

The silicone containing component(s) may be present in amounts up to about 95 weight %, or from about 10 to about 80 weight %, or from about 20 to about 70 weight %, based upon all reactive components of the reactive mixture (excluding diluents).

Polyamides

The reactive mixture may include at least one polyamide. As used herein, the term "polyamide" refers to polymers and copolymers comprising repeating units containing amide groups. The polyamide may comprise cyclic amide groups, acyclic amide groups and combinations thereof and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups.

Examples of suitable acyclic polyamides include polymers and copolymers comprising repealing units of Formulae G1 and G2:

Formula G1

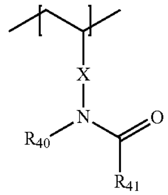

Formula G2

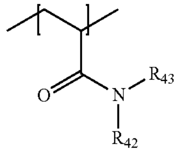

wherein X is a direct bond, —(CO)—, or —($CONHR_{44}$)—, wherein $R_{44}$ is a $C_1$ to $C_3$ alkyl group; $R_{40}$ is selected from H, straight or branched, substituted or unsubstituted $C_1$ to $C_4$ alkyl groups; $R_{41}$ is selected from H, straight or branched, substituted or unsubstituted $C_1$ to $C_4$ alkyl groups, amino groups having up to two carbon atoms, amide groups having up to four carbon atoms, and alkoxy groups having up to two carbon groups; $R_{42}$ is selected from H, straight or branched, substituted or unsubstituted $C_1$ to $C_4$ alkyl groups; or methyl, ethoxy, hydroxyethyl, and hydroxymethyl; $R_{43}$ is selected from H, straight or branched, substituted or unsubstituted $C_1$ to $C_4$ alkyl groups; or methyl, ethoxy, hydroxyethyl, and hydroxymethyl; wherein the number of carbon atoms in $R_{40}$ and $R_{41}$ taken together is 8 or less, including 7, 6, 5, 4, 3, or less; and wherein the number of carbon atoms in $R_{42}$ and $R_{43}$ taken together is 8 or less, including 7, 6, 5, 4, 3, or less. The number of carbon atoms in $R_{40}$ and $R_{41}$ taken together may be 6 or less or 4 or less. The number of carbon atoms in $R_{42}$ and $R_{43}$ taken together may be 6 or less. As used herein substituted alkyl groups include alkyl groups substituted with an amine, amide, ether, hydroxyl, carbonyl or carboxy groups or combinations thereof.

$R_{40}$ and $R_{41}$ may be independently selected from H, substituted or unsubstituted $C_1$ to $C_2$ alkyl groups. X may be a direct bond, and $R_{40}$ and $R_{41}$ may be independently selected from H, substituted or unsubstituted $C_1$ to $C_2$ alkyl groups. $R_{42}$ and $R_{43}$ can be independently selected from H, substituted or unsubstituted $C_1$ to $C_2$ alkyl groups, methyl, ethoxy, hydroxyethyl, and hydroxymethyl.

The acyclic polyamides of the present invention may comprise a majority of the repeating units of Formula LV or Formula LVI, or the acyclic polyamides can comprise at least 50 mole percent of the repeating unit of Formula G or Formula G1, including at least 70 mole percent, and at least 80 mole percent. Specific examples of repeating units of Formula G and Formula G1 include repeating units derived from N-vinyl-N-methylacetamide, N-vinylacetamide, N-vinyl-N-methylpropionamide, N-vinyl-N-methyl-2-methylpropionamide, N-vinyl-2-methyl-propionamide, N-vinyl-N, N'-dimethylurea, N, N-dimethylacrylamide, methacrylamide, and acyclic amides of Formulae G2 and G3:

Formula G2

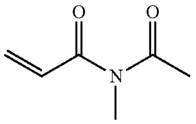

Formula G3

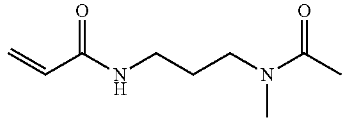

Examples of suitable cyclic amides that can be used to form the cyclic polyamides of include α-lactam, β-lactam, γ-lactam, δ-lactam, and ε-lactam. Examples of suitable cyclic polyamides include polymers and copolymers comprising repeating units of Formula G4:

Formula G4

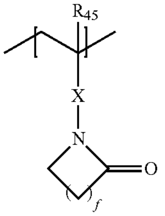

wherein $R_{45}$ is a hydrogen atom or methyl group; wherein f is a number from 1 to 10; wherein X is a direct bond, —(CO)—, or —($CONHR_{46}$)—, wherein $R_{46}$ is a $C_1$ to $C_3$ alkyl group. In Formula LIX, f may be 8 or less, including 7, 6, 5, 4, 3, 2, or 1. In Formula G4, f may be 6 or less, including 5, 4, 3, 2, or 1. In Formula G4, f may be from 2 to 8, including 2, 3, 4, 5, 6, 7, or 8. In Formula LIX, f may be 2 or 3. When X is a direct bond, f may be 2. In such instances, the cyclic polyamide may be polyvinylpyrrolidone (PVP).

The cyclic polyamides of the present invention may comprise 50 mole percent or more of the repeating unit of Formula G4, or the cyclic polyamides can comprise at least 50 mole percent of the repeating unit of Formula G4, including at least 70 mole percent, and at least 80 mole percent.

The polyamides may also be copolymers comprising repeating units of both cyclic and acyclic amides. Additional repeating units may be formed from monomers selected from hydroxyalkyl(meth)acrylates, alkyl(meth)acrylates, other hydrophilic monomers and siloxane substituted (meth) acrylates. Any of the monomers listed as suitable hydrophilic monomers may be used as co-monomers to form the additional repeating units. Specific examples of additional monomers which may be used to form polyamides include 2-hydroxyethyl (meth)acrylate, vinyl acetate, acrylonitrile, hydroxypropyl (meth)acrylate, methyl (meth)acrylate and hydroxybutyl (meth)acrylate, dihydroxypropyl (meth)acrylate, polyethylene glycol mono(meth)acrylate, and the like and mixtures thereof. Ionic monomers may also be included. Examples of ionic monomers include (meth)acrylic acid, N-[(ethenyloxy)carbonyl]-β-alanine (VINAL, CAS #148969-96-4), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT, carboxybetaine; CAS 79704-35-1), 1-propanaminium, N,N-dimethyl-N-[3-[(1-oxo-2-propen-1-yl)amino]propyl]-3-sulfo-, inner salt (SBT, sulfobetaine, CAS 80293-60-3), 3,5-Dioxa-8-aza-4-phosphaundec-10-en-1-aminium, 4-hydroxy-N,N,N-trimethyl-9-oxo-, inner salt, 4-oxide (9CI) (PBT, phosphobetaine, CAS 163674-35-9, 2-methacryloyloxyethyl phosphorylcholine, 3-(dimethyl(4-vinylbenzyl)ammonio) propane-1-sulfonate (DMVBAPS), 3-((3-acrylamidopropyl) dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), methacryloyloxy)propyl)dimethylammonio)propane-1-sulfonate (MAPDAPS).

The reactive monomer mixture may comprise both an acyclic polyamide and a cyclic polyamide or copolymers thereof. The acyclic polyamide can be any of those acyclic polyamides described herein or copolymers thereof, and the cyclic polyamide can be any of those cyclic polyamides described herein or copolymers thereof. The polyamide may be selected from the group polyvinylpyrrolidone (PVP), polyvinylmethyacetamide (PVMA), polydimethylacrylamide (PDMA), polyvinylacetamide (PNVA), poly(hydroxyethyl(meth)acrylamide), polyacrylamide, and copolymers and mixtures thereof. The polyamide may be a mixture of PVP (e.g., PVP K90) and PVMA (e.g., having a Mw of about 570 KDa).

The total amount of all polyamides in the reactive mixture may be in the range of between 1 weight percent and about 35 weight percent, including in the range of about 1 weight percent to about 15 weight percent, and in the range of about 5 weight percent to about 15 weight percent, in all cases, based on the total weight of the reactive components of the reactive monomer mixture.

Without intending to be bound by theory, when used with a silicone hydrogel, the polyamide functions as an internal wetting agent. The polyamides of the present invention may be non-polymerizable, and in this case, are incorporated into the silicone hydrogels as semi-interpenetrating networks. The polyamides are entrapped or physically retained within the silicone hydrogels. Alternatively, the polyamides of the present invention may be polymerizable, for example as polyamide macromers or prepolymers, and in this case, are covalently incorporated into the silicone hydrogels. Mixtures of polymerizable and non-polymerizable polyamides may also be used.

When the polyamides are incorporated into the reactive monomer mixture they may have a weight average molecular weight of at least 100,000 daltons; greater than about 150,000; between about 150,000 to about 2,000,000 daltons; between about 300,000 to about 1,800,000 daltons. Higher molecular weight polyamides may be used if they are compatible with the reactive monomer mixture.

Cross-Linking Agents

It is generally desirable to add one or more cross-linking agents, also referred to as cross-linking monomers, multi-functional macromers, and prepolymers, to the reactive mixture. The cross-linking agents may be selected from bifunctional crosslinkers, trifunctional crosslinkers, tetra-functional crosslinkers, and mixtures thereof, including silicone-containing and non-silicone containing cross-linking agents. Non-silicone-containing cross-linking agents include ethylene glycol dimethacrylate (EGDMA), tetraethylene glycol dimethacrylate (TEGDMA), trimethylolpropane trimethacrylate (TMPTMA), triallyl cyanurate (TAC), glycerol trimethacrylate, methacryloxyethyl vinylcarbonate (HEMAVc), allylmethacrylate, methylene bisacrylamide (MBA), and polyethylene glycol dimethacrylate wherein the polyethylene glycol has a molecular weight up to about 5000 Daltons. The cross-linking agents are used in the usual amounts, e.g., from about 0.000415 to about 0.0156 mole per 100 grams of reactive Formulas in the reactive mixture. Alternatively, if the hydrophilic monomers and/or the silicone-containing components are multifunctional by molecular design or because of impurities, the addition of a cross-linking agent to the reactive mixture is optional. Examples of hydrophilic monomers and macromers which can act as the cross-linking agents and when present do not require the addition of an additional cross-linking agent to the reactive mixture include (meth)acrylate and (meth)acrylamide end-capped polyethers. Other cross-linking agents will be known to one skilled in the art and may be used to make the silicone hydrogel of the present invention.

It may be desirable to select crosslinking agents with similar reactivity to one or more of the other reactive components in the formulation. In some cases, it may be desirable to select a mixture of crosslinking agents with different reactivity in order to control some physical, mechanical or biological property of the resulting silicone hydrogel. The structure and morphology of the silicone hydrogel may also be influenced by the diluent(s) and cure conditions used.

Multifunctional silicone-containing components, including macromers, cross-linking agents, and prepolymers, may also be included to further increase the modulus and retain tensile strength. The silicone containing cross-linking agents may be used alone or in combination with other cross-linking agents. An example of a silicone containing component which can act as a cross-linking agent and, when present, does not require the addition of a crosslinking monomer to the reactive mixture includes α, ω-bismethacryloxypropyl polydimethylsiloxane. Another example is bis-3-acryloxy-2-hydroxypropyloxypropyl polydimethylsiloxane (ac-PDMS).

Cross-linking agents that have rigid chemical structures and polymerizable groups that undergo free radical polymerization may also be used. Non-limiting examples of suitable rigid structures include cross-linking agents comprising phenyl and benzyl ring, such are 1,4-phenylene diacrylate, 1,4-phenylene dimethacrylate, 2,2-bis(4-methacryloxyphenyl)-propane, 2,2-bis[4-(2-acryloxyethoxy)phenyl]propane, 2,2-bis[4-(2-hydroxy-3-methacryloxypropoxy)-phenyl]propane, and 4-vinylbenzyl methacrylate, and combinations thereof. Rigid crosslinking agents may be included in amounts between about 0.5 and about 15, or 2-10, 3-7 based upon the total weight of all of the reactive components. The physical and mechanical properties of the silicone hydrogels of the present invention may be optimized for a particular use by adjusting the components in the reactive mixture.

Non-limiting examples of silicone cross-linking agents also include the multi-functional silicone-containing components described above, such as compounds of Formula E (and its sub-formulae) and the multi-functional compounds shown in Table 3.

Further Constituents

The reactive mixture may contain additional components such as, but not limited to, diluents, initiators, UV absorbers, visible light absorbers, photochromic compounds, pharmaceuticals, nutraceuticals, antimicrobial substances, tints, pigments, copolymerizable dyes, nonpolymerizable dyes, release agents, and combinations thereof.

Classes of suitable diluents for silicone hydrogel reactive mixtures include alcohols having 2 to 20 carbon atoms, amides having 10 to 20 carbon atoms derived from primary amines and carboxylic acids having 8 to 20 carbon atoms. The diluents may be primary, secondary, and tertiary alcohols.

Generally, the reactive components are mixed in a diluent to form a reactive mixture. Suitable diluents are known in the art. For silicone hydrogels, suitable diluents are disclosed in WO 03/022321 and U.S. Pat. No. 6,020,445, the disclosure of which is incorporated herein by reference. Classes of suitable diluents for silicone hydrogel reactive mixtures include alcohols having 2 to 20 carbons, amides having 10 to 20 carbon atoms derived from primary amines, and carboxylic acids having 8 to 20 carbon atoms. Primary and tertiary alcohols may be used. Preferred classes include alcohols having 5 to 20 carbons and carboxylic acids having 10 to 20 carbon atoms. Specific diluents which may be used include 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, (3-acetoxy-2-hydroxypropyloxy)-propylbis(trimethylsiloxy) methylsilane, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino) ethanol mixtures thereof and the like. Examples of amide diluents include N,N-dimethyl propionamide and dimethyl acetamide.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like. If a diluent is present, generally there are no particular restrictions with respect to the amount of diluent present. When diluent is used, the diluent may be present in an amount in the range of about 2 to about 70 weight percent, including in the range of about 5 to about 50 weight percent, and in the range of about 15 to about 40 weight percent, based on the total weight of the reactive mixtures (including reactive and nonreactive Formulas). Mixtures of diluents may be used.

A polymerization initiator may be used in the reactive mixture. The polymerization initiator may include, for instance, at least one of lauroyl peroxide, benzoyl peroxide, iso-propyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphine eoxide (Irgacure 819), 2,4,6-trimethylbenzyldiphenyl phos-phine oxide and 2,4,6-trimethylbenzoyl diphenylphosphine oxide, benzoin methyl ester and a combination of cam-phorquinone and ethyl 4-(N,N-dimethylamino)benzoate.

Commercially available (from IGM Resins B.V., The Netherlands) visible light initiator systems include Irgacure® 819, Irgacure® 1700, Irgacure® 1800, Irgacure® 819, Irgacure® 1850 and Lucrin® TPO initiator. Commercially available (from IGM Resins B.V.) UV photoinitiators include Darocur® 1173 and Darocur® 2959. These and other photoinitiators which may be used are disclosed in Volume III, Photoinitiators for Free Radical Cationic & Anionic Photopolymerization, 2nd Edition by J. V. Crivello & K. Dietliker; edited by G. Bradley; John Wiley and Sons; New York; 1998. The initiator is used in the reactive mixture in effective amounts to initiate photopolymerization of the reactive mixture, e.g., from about 0.1 to about 2 parts by weight per 100 parts of reactive monomer mixture. Polymerization of the reactive mixture can be initiated using the appropriate choice of heat or visible or ultraviolet light or other means depending on the polymerization initiator used. Alternatively, initiation can be conducted using e-beam without a photoinitiator. However, when a photoinitiator is used, the preferred initiators are bisacylphosphine oxides, such as bis(2,4,6-tri-methylbenzoyl)-phenyl phosphine oxide (Irgacure® 819) or a combination of 1-hydroxycyclohexyl phenyl ketone and bis(2,6-dimethoxybenzoyl)-2,4-4-trimethylpentyl phosphine oxide (DMBAPO).

The reactive mixture for making the ophthalmic devices of the invention may comprise, in addition to a high energy light absorbing compound, any of the polymerizable compounds and optional components described above.

Preferred reactive mixtures may comprise: a high energy light absorbing compound, such as a formula I compound, and a hydrophilic component.

Preferred reactive mixtures may comprise: a high energy light absorbing compound, such as a formula I compound, and a hydrophilic component selected from DMA, NVP, HEMA, VMA, NVA, methacrylic acid, and mixtures thereof. Preferred are mixtures of HEMA and methacrylic acid.

Preferred reactive mixtures may comprise: a high energy light absorbing compound, such as a formula I compound, a hydrophilic component, and a silicone-containing component.

Preferred reactive mixtures may comprise: a high energy light absorbing compound, such as a formula I compound, a hydrophilic component, and a silicone-containing component comprising a compound of formula D (or its subformulae, such as D-1, D-2, etc.).

Preferred reactive mixtures may comprise: a high energy light absorbing compound, such as a formula I compound, a hydrophilic component selected from DMA, NVP, HEMA, VMA, NVA, and mixtures thereof, a silicone-containing component comprising a compound of formula D (or its sub-formulae, such as D-1, D-2, etc.); and an internal wetting agent.

Preferred reactive mixtures may comprise: a high energy light absorbing compound, such as a formula I compound, a hydrophilic component selected from DMA, HEMA and mixtures thereof, a silicone-containing component selected from 2-hydroxy-3-[3-methyl-3,3-di(trimethylsiloxy)silylpropoxy]-propyl methacrylate (SiMAA), mono-methacryloxypropyl terminated mono-n-butyl terminated polydimethylsiloxane (mPDMS), mono-(2-hydroxy-3-methacryloxypropyl)-propyl ether terminated mono-n-butyl terminated polydimethylsiloxane (OH-mPDMS), and mixtures thereof, and a wetting agent (preferably PVP or PVMA). For the hydrophilic component, mixtures of DMA and HEMA are preferred. For the silicone containing component, mixtures of SiMAA and mPDMS are preferred.

Preferred reactive mixtures may comprise: a high energy light absorbing compound, such as a formula I compound, a hydrophilic component comprising a mixture of DMA and HEMA; a silicone-containing component comprising a mixture of OH-mPDMS having from 2 to 20 repeat units (preferably a mixture of 4 and 15 repeat units). Preferably, the reactive mixture further comprises a silicone-containing crosslinker, such as ac-PDMS. Also preferably, the reactive mixture contains a wetting agent (preferably DMA, PVP, PVMA or mixtures thereof).

Preferred reactive mixtures may comprise: a high energy light absorbing compound, such as a formula I compound; between about 1 and about 15 wt % at least one polyamide (e.g., an acyclic polyamide, a cyclic polyamide, or mixtures thereof); at least one first mono-functional, hydroxyl substituted poly(disubstituted siloxane) having 4 to 8 siloxane repeating units (e.g, OH-mPDMS where n is 4 to 8, preferably n is 4); at least one second hydroxyl substituted poly(disubstituted siloxane) that is a mono-functional hydroxyl substituted poly(disubstituted siloxane)s having 10 to 200 or 10-100 or 10-50 or 10-20 siloxane repeating units (e.g., OH-mPDMS where n is 10 to 200 or 10-100 or 10-50 or 10-20, preferably n is 15); about 5 to about 35 wt % of at least one hydrophilic monomer; and optionally a multifunctional hydroxyl substituted poly(disubstituted siloxane)s having 10 to 200, or 10 to 100 siloxane repeating units (e.g., ac-PDMS). Preferably, the first mono-functional, hydroxyl substituted poly(disubstituted siloxane) and the second hydroxyl substituted poly(disubstituted siloxane) are present in concentrations to provide a ratio of weight percent of the first mono-functional, hydroxyl substituted poly(disubstituted siloxane) to weight percent of the second hydroxyl substituted poly(disubstituted siloxane) of 0.4-1.3, or 0.4-1.0.

The foregoing reactive mixtures may contain optional ingredients such as, but not limited to, one or more initiators, internal wetting agents, crosslinkers, other UV or HEV absorbers, and diluents.

Compounds of formula I, when copolymerized with other reactive components, provide polymerized products that contain chromophoric substituents. Such chromophoric substituents can provide the product with desirable light absorbing properties as described above. For instance, ophthalmic devices, such as a contact lenses, that contain the chromophoric substituent, may block undesirable high energy light, as described in detail above. Thus, the invention encompasses ophthalmic devices that are polymerized reaction products of a reactive mixture (comprising, for instance, a hydrophilic component, and a silicone containing compound), wherein the polymerized reaction product contains, as covalently bound substituents, one or more chromophores of formula IV:

Formula IV

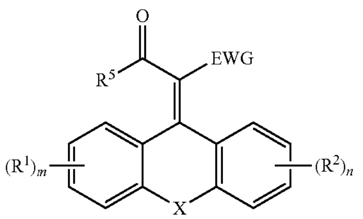

wherein m and n are independently 0, 1, 2, 3, or 4; X is O, S, NR, SO, or $SO_2$; R at each occurrence is independently H, $C_1$-$C_6$ alkyl, cycloalkyl, heterocycloalkyl, aryl, heteroaryl, or a link to the polymerized reaction product; $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; $R^5$ is a link to the polymerized reaction product; and EWG is an electron withdrawing group (preferably cyano).

In formula IV, X is preferably O or S. In formula IV, the link to the polymerized reaction product preferably comprises the residue of a polymerizable group and one or more of an alkylene group, a cycloalkylene group, a heterocycloalkylene group, an arylene group, a heteroarylene group, an oxaalkylene group, an alkylene-amide-alkylene group, or an alkylene-amine-alkylene group. Preferred polymerizable groups include styryl, vinyl carbonate, vinyl ether, vinyl carbamate, N-vinyl lactam, N-vinylamide, (meth)acrylate, or (meth)acrylamide.

Preferred polymerized reaction products may further comprise one or more covalently attached UV absorbing chromophores, in addition to the chromophore of formula IV. Preferred UV absorbing chromophores include the residue of a benzophenone, a benzotriazole, a triazine, a substituted acrylonitrile, a salicyclic acid derivative, a benzoic acid derivative, a cinnamic acid derivative, a chalcone derivative, a dypnone derivative, a crotonic acid derivative, or mixtures thereof.

Curing of Hydrogels and Manufacture of Lens

The reactive mixtures may be formed by any of the methods known in the art, such as shaking or stirring, and used to form polymeric articles or devices by known methods. The reactive components are mixed together either with or without a diluent to form the reactive mixture.

For example, ophthalmic devices may be prepared by mixing reactive components, and, optionally, diluent(s), with a polymerization initiator and curing by appropriate conditions to form a product that can be subsequently formed into the appropriate shape by lathing, cutting, and the like. Alternatively, the reactive mixture may be placed in a mold and subsequently cured into the appropriate article.

A method of making a molded ophthalmic device, such as a silicone hydrogel contact lens, may comprise: preparing a reactive monomer mixture; transferring the reactive monomer mixture onto a first mold; placing a second mold on top the first mold filled with the reactive monomer mixture; and curing the reactive monomer mixture by free radical copolymerization to form the silicone hydrogel in the shape of a contact lens.

The reactive mixture may be cured via any known process for molding the reactive mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The contact lenses of this invention may be formed by the direct molding of the silicone hydrogels, which is economical, and enables precise control over the final shape of the hydrated lens. For this method, the reactive mixture is placed in a mold having the shape of the final desired silicone hydrogel and the reactive mixture is subjected to conditions whereby the monomers polymerize, thereby producing a polymer in the approximate shape of the final desired product.

After curing, the lens may be subjected to extraction to remove unreacted components and release the lens from the lens mold. The extraction may be done using conventional extraction fluids, such organic solvents, such as alcohols or may be extracted using aqueous solutions.

Aqueous solutions are solutions which comprise water. The aqueous solutions of the present invention may comprise at least about 20 weight percent water, or at least about 50 weight percent water, or at least about 70 weight percent water, or at least about 95 weight percent water. Aqueous solutions may also include additional water soluble Formulas such as inorganic salts or release agents, wetting agents, slip agents, pharmaceutical and nutraceutical Formulas, combinations thereof and the like. Release agents are compounds or mixtures of compounds which, when combined with water, decrease the time required to release a contact lens from a mold, as compared to the time required to release such a lens using an aqueous solution that does not comprise the release agent. The aqueous solutions may not require special handling, such as purification, recycling or special disposal procedures.

Extraction may be accomplished, for example, via immersion of the lens in an aqueous solution or exposing the lens to a flow of an aqueous solution. Extraction may also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leaching or extraction aid in the aqueous solution to a level sufficient to facilitate adequate removal of unreacted components from the lens. The foregoing may be conducted in batch or continuous processes, with or without the addition of heat, agitation or both.

Application of physical agitation may be desired to facilitate leach and release. For example, the lens mold part to which a lens is adhered can be vibrated or caused to move back and forth within an aqueous solution. Other methods may include ultrasonic waves through the aqueous solution.

The lenses may be sterilized by known means such as, but not limited to, autoclaving.

As indicated above, preferred ophthalmic devices are contact lenses, more preferably soft hydrogel contact lenses. The transmission wavelengths and percentages described herein may be measured on various thicknesses of lenses using, for instance, the methodologies described in the Examples. By way of example, a preferred center thickness for measuring transmission spectra in a soft contact lens may be from 80 to 100 microns, or from 90 to 100 microns or from 90 to 95 microns. Typically, the measurement may be made at the center of the lens using, for instance, a 4 nm instrument slit width. Various concentrations of the one or more polymerizable high energy light absorbing compounds may be used to achieve the transmission characteristics described above. For instance, the concentration may be in the range of at least 1 percent, or at least 2 percent; and up to 10 percent, or up to 5 percent, based on the weight percentages of all components in the reactive mixture, excluding diluent. A typical concentration may be in the range of 3 to 5 percent.

Silicone hydrogel ophthalmic devices (e.g., contact lenses) according to the invention preferably exhibit the following properties. All values are prefaced by "about," and the devices may have any combination of the listed properties. The properties may be determined by methods known to those skilled in the art, for instance as described in United States pre-grant publication US20180037690, which is incorporated herein by reference.

Water concentration %: at least 20%, or at least 25% and up to 80% or up to 70%

Haze: 30% or less, or 10% or less

Kruss dynamic contact angle (°): 1000 or less, or 500 or less

Tensile Modulus (psi): 120 or less, or 80 to 120

Oxygen permeability (Dk, barrers): at least 80, or at least 100, or at least 150, or at least 200

Elongation to Break: at least 100

For ionic silicon hydrogels, the following properties may also be preferred (in addition to those recited above):

Lysozyme uptake (μg/lens): at least 100, or at least 150, or at least 500, or at least 700

Polyquaternium 1 (PQ1) uptake (%): 15 or less, or 10 or less, or 5 or less

Some embodiments of the invention will now be described in detail in the following Examples.

EXAMPLES

Test Methods

Ultraviolet-visible spectra of compounds in solution were measured on a Perkin Elmer Lambda 45 or an Agilent Cary 6000i UV/VIS scanning spectrometer. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission or absorbance; and baseline correction was selected (e.g., neglecting reflective loss). For the Cary instrument, the scan range was 200-800 nm; the scan speed was 600 nm/min; the slit width was 2 nm; the mode was transmission or absorbance; and baseline correction was selected (e.g., neglecting reflective loss). A baseline correction was performed before samples were analyzed using the autozero function.

Ultraviolet-visible spectra of contact lenses formed in part from the claimed compositions were measured on a Perkin Elmer Lambda 45 UV/VIS or an Agilent Cary 6000i UV/VIS scanning spectrometer using packing solution. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission; and baseline correction was selected. Baseline correction was performed using cuvettes containing plastic two-piece lens holders and the same solvents. These two-piece contact lens holders were designed to hold the sample in the quartz cuvette in the location through which the incident light beam traverses. The reference cuvette also contained a two-piece holder. To ensure that the thickness of the samples is constant, all lenses were made using identical molds. The center thickness of the contact lens was measured using an electronic thickness gauge. Reported center thickness and percent transmission spectra are obtained by averaging three individual lens data.

It is important to ensure that the outside surfaces of the cuvette are completely clean and dry and that no air bubbles are present in the cuvette. Repeatability of the measurement is improved when the reference cuvette and its lens holder remain constant and when all samples use the same sample cuvette and its lens holder, making sure that both cuvettes are properly inserted into the instrument.

The following abbreviations will be used throughout the Examples and Figures and have the following meanings:

BC: back or base curve plastic mold
FC: front curve plastic mold
DMA: N, N-dimethylacrylamide (Jarchem)
HEMA: 2-hydroxyethyl methacrylate (Bimax)
PVP: poly(N-vinylpyrrolidone) (ISP Ashland)
PDMA: polydimethylacrylamide
PVMA: polyvinylmethyacetamide
EGDMA: ethylene glycol dimethacrylate (Esstech)
TEGDMA: tetraethylene glycol dimethacrylate (Esstech)
Irgacure 819: bis(2,4,6-trimethylbenzoyl)-phenylphosphineoxide (BASF or Ciba Specialty Chemicals)
Irgacure 1870: blend of bis(2,6-dimethoxybenzoyl)-2,4,4-trimethyl-pentylphosphineoxide and 1-hydroxy-cyclohexyl-phenyl-ketone (BASF or Ciba Specialty Chemicals)
mPDMS: mono-n-butyl terminated monomethacryloxypropyl terminated polydimethylsiloxane ($M_n$=800-1000 daltons) (Gelest)
HO-mPDMS: mono-n-butyl terminated mono-(2-hydroxy-3-methacryloxypropyloxy)-propyl terminated polydimethylsiloxane ($M_n$=400-1500 daltons) (Ortec or DSM-Polymer Technology Group)
ac-PDMS: bis-3-acryloxy-2-hydroxypropyloxypropyl polydimethylsiloxane (Tegomer V-Si 2250 from Evonik)
Blue HEMA: 1-amino-4-[3-(4-(2-methacryloyloxy-ethoxy)-6-chlorotriazin-2-ylamino)-4-sulfophenylamino]anthraquinone-2-sulfonic acid, as described in U.S. Pat. No. 5,944,853
Da: dalton or g/mole
kDa: kilodalton or an atomic mass unit equal to 1,000 daltons
SiMAA: 2-propenoic acid, 2-methyl-2-hydroxy-3-[3-[1,3,3,3-tetramethyl-1-[(trimethylsilyl)oxy]disiloxanyl]propoxy]propyl ester (Toray) or 3-(3-(1,1,1,3,5,5,5-heptamethyltrisiloxan-3-yl)propoxy)-2-hydroxypropyl methacrylate
RB247: 1,4-Bis[2-methacryloxyethylamino]-9,10-anthraquinone
BHT:—butylated hydroxytoluene
D3O: 3,7-dimethyl-3-octanol (Vigon)
DIW: deionized water
MeOH: methanol
IPA: isopropyl alcohol
HCl: hydrochloric acid
$CH_2Cl_2$ or DCM: methylene chloride or dichloromethane
$SOCl_2$: thionyl chloride
mCPBA: m-chloroperbenzoic acid
EtOAc: ethyl acetate
$NH_2CH_2CH_2OH$: ethanolamine or 2-aminoethanol
Norbloc: 2-(2'-hydroxy-5-methacrylyloxyethylphenyl)-2H-benzotriazole (Janssen)
PP: polypropylene which is the homopolymer of propylene
TT: Tuftec which is a hydrogenated styrene butadiene block copolymer (Asahi Kasei Chemicals)
Z: Zeonor which is a polycycloolefin thermoplastic polymer (Nippon Zeon Co Ltd)
TL03 lights: Phillips TLK 40 W/03 bulbs
LED: light emitting diode
$^{1}$N NMR: proton nuclear magnetic resonance spectroscopy
UV-VIS: ultraviolet-visible spectroscopy
L: liter
mL: milliliter
Equiv. or eq.: equivalent
kg: kilogram
g: gram
mol: mole
mmol: millimole
min: minute(s)
nm: nanometer(s)
TLC: thin layer chromatography
Borate Buffered Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2-liter volumetric flask.

Example 1—Synthesis of 2-(2-cyanoacetamido) ethyl methacrylate (A) and 2-(2-cyano-2-(9H-thioxanthen-9-ylidene)acetamido)ethyl methacrylate (B) as Shown in Scheme 2

Scheme 2

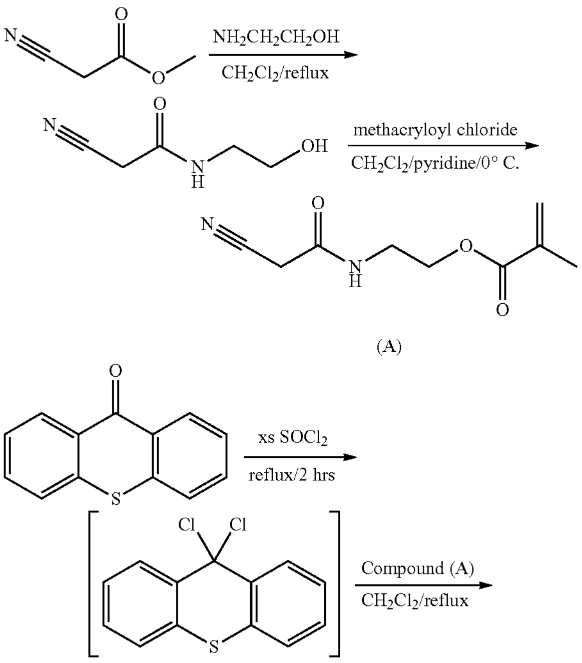

(A)

-continued

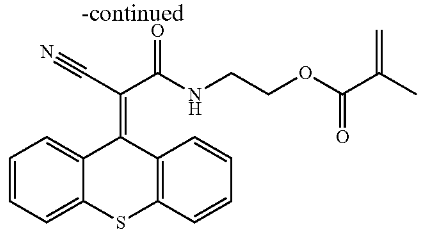

(B)

Methyl cyanoacetate (40 grams, 0.4037 mole) and 25 mL of dichloromethane were stirred in a 3 neck, 500 mL round bottom flask under equipped with a reflux condenser under a nitrogen environment. 2-aminoethanol (23.8 grams, 0.3897 mole, ~0.97 eq.) was added to the solution via an addition funnel, after which the temperature rose and the methylene chloride began to reflux. After the exotherm ceased, external heat was applied to continue a gentle reflux for a total of two hours, after which no ethanolamine was observed by thin layer chromatography.

The reaction may also be conducted at room temperature and is complete within a few hours.

The mixture was cooled to room temperature and all the methylene chloride was evaporated at reduced pressure. The residual oil was washed three times with 50 mL of ethyl acetate to remove unreacted starting material and non-polar impurities. The residual ethyl acetate was then removed under reduced pressure, and the resulting oil was used for acylation without any further purification.

The crude N-2-hydroxyethylacetamide derivative was dissolved in 150 mL of dichloromethane containing 40 grams of pyridine (~0.5 mole) in a three-neck round bottom flask equipped with a reflux condenser, an addition funnel, and a magnetic stirring bar. The flask was immersed in an ice bath and allowed to cool down to around 0° C. Methacryloyl chloride (45.76 grams, ~0.44 mole) was added dropwise from the addition funnel, and the resulting reaction mixture was allowed to warm up to room temperature while constantly stirring the system. Methanol (20 mL) was the added to the flask to quench any unreacted methacryloyl chloride. The volatile components were removed by rotary evaporation under reduced pressure, and the crude product dissolved in 800 mL of dilute aqueous HCl. The resulting aqueous solution was extracted three times with 100 mL of hexanes in a separatory funnel to remove any non-polar impurities. The organic layers were discarded. Sodium chloride was added to the aqueous layer which was then extracted three times with 300 mL of ethyl acetate. About 50 milligrams of BHT were added to the combined organic fractions as an inhibitor, and the ethyl acetate removed by rotary evaporation under reduced pressure. The crude product crystalized out of solution during solvent removal. When about 100 mL of ethyl acetate was left in the flask, 250 mL of hexanes was added, and the crude product was isolated by vacuum filtration using a fritted glass funnel. Thin layer chromatography indicated the presence of a single compound. The filter cake was washed two times with 150 mL of hexanes and then vacuum dried at 40° C., yielding 53 grams (about 70% yield) of 2-(2-cyanoacetamido)ethyl methacrylate (A). $^1$H NMR (500 MHz, $CDCl_3$) δ 1.93 (3H, s, $CH_3$), 3.36 (2H, s, $CNCH_2$), 3.60 (2H, dd, $CH_2NH$), 4.26 (2H, t, $CH_2OC{=}O$), 5.59 (1H, m, vinylic), 6.11 (1H, bs, vinylic), 6.52 (1H, bs, NH).

A mixture of 9H-thioxanthene-9-one (2.12 grams, 0.01 mole) and thionyl chloride (5 mL, 8.2 grams, ~0.07 mole) was refluxed in a 50 mL round bottom flask under a nitrogen atmosphere with constant stirring. After two hours, the red solution was evaporated to dryness ensuring that all unreacted thionyl chloride was removed from the system. 2-(2-Cyanoacetamido)ethyl methacrylate (A) (2.3 grams, 0.0117 mole, ~1.17 eq.) and 15 mL of dichloromethane were added, and the resulting reaction mixture was heated to reflux under a nitrogen blanket. The reaction was monitored by thin layer chromatography. After two hours, no changes were observed in the chromatogram, so the reactive mixture was allowed to cool down to room temperature. 2-(2-cyano-2-(9H-thioxanthen-9-ylidene)acetamido)ethyl methacrylate (B) was isolated as yellow crystals (3.2 grams, 82% yield) after passing through a short silica gel column ($CH_2Cl_2$, followed by 8 weight % EtOAc in $CH_2Cl_2$). The UV-VIS transmission spectrum of a 0.2 mM methanol solution Compound B is shown in FIG. 1. $^1$H NMR (500 MHz, $CDCl_3$) δ 1.84 (3H, s, $CH_3$), 3.47 (2H, m, $CH_2NH$), 4.01 (2H, t, $CH_2OC{=}O$), 5.55 (1H, m, vinylic), 5.91 (1H, bs, NH), 5.98 (1H, bs, vinylic), 7.24 (1H, t, Ar—H), 7.31 (1H, t, Ar—H), 7.39 (2H, m, Ar—H), 7.49 (1H, d, Ar—H), 7.55 (1H, m, Ar—H), 7.61 (1H, d, Ar—H), 8.04 (1H, m, Ar—H).

Example 2—Synthesis of 2-(2-cyano-2-(9H-xanthen-9-ylidene)acetamido)ethyl methacrylate (C) as Shown in Scheme 3

Scheme 3

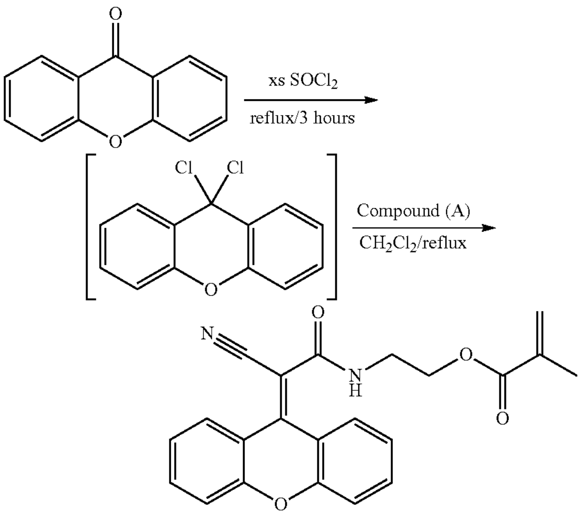

(C)

A mixture of 9H-xanthen-9-one (5.0 grams, 0.0255 mole) and thionyl chloride (10 mL, 16.4 grams, 0.138 mole) was refluxed in a 50 mL round bottom flask under a nitrogen atmosphere with constant stirring. After three hours, the red solution was evaporated to dryness ensuring that all unreacted thionyl chloride was removed from the system. 2-(2-cyanoacetamido)ethyl methacrylate (A) (6.0 grams, 0.0306 mole, ~1.2 eq.) and 20 mL of dichloromethane were added and the resulting reaction mixture was heated to reflux under a nitrogen blanket. The reaction was monitored by thin layer chromatography. The mixture was cooled to room temperature after 2.5 hours and 2-(2-cyano-2-(9H-xanthen-9-ylidene)acetamido)ethyl methacrylate (C) purified after passing through a short silica gel column ($CH_2Cl_2$, and ethyl acetate in $CH_2Cl_2$). The off-white precipitate formed during rotary evaporation is washed with hexane and dried in a vacuum oven at 40° C. overnight. The UV-VIS transmission spectrum of Compound (C) is shown in FIG. 1 in a 0.2 mM methanol solution. $^1H$ NMR (500 MHz, $CDCl_3$) δ 1.85 (3H, s, $CH_3$), 3.60 (2H, dd, $CH_2NH$), 4.2 (2H, t, $CH_2OC{=}O$), 5.53 (1H, t, vinylic), 5.99 (1H, bs, vinylic), 6.17 (1H, t, NH), 7.12 (1H, t, Ar—H), 7.29-7.34 (3H, m, Ar—H), 7.45 (1H, ddd, Ar—H), 7.52 (1H, ddd, Ar—H), 7.67 (1H, dd, Ar—H), 8.41 (1H, dd, Ar—H).

Example 3—Synthesis of 2-(2-cyano-2-(10-methylacridin-9(10H)-ylidene)acetamido)ethyl methacrylate (D) as Shown in Scheme 4 (Prophetic)

Scheme 4

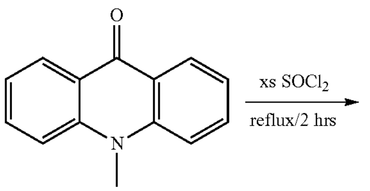

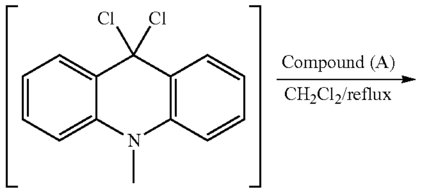

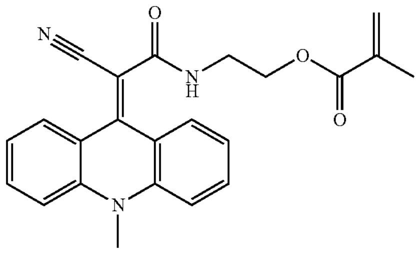

(D)

A mixture of 10-methylacridin-9(10H)-one (2.09 grams, 0.01 mole) and thionyl chloride (5 mL, 8.2 grams, ~0.07 mole) is refluxed in a 50 mL round bottom flask under a nitrogen atmosphere with constant stirring. After two hours, the solution is evaporated to dryness ensuring that all unreacted thionyl chloride is removed from the system. 2-(2-cyanoacetamido)ethyl methacrylate (A) (2.3 grams, 0.0117 mole, ~1.17 eq.) and 15 mL of dichloromethane are added and the resulting reaction mixture is heated to reflux under a nitrogen blanket. The reaction is monitored by thin layer chromatography. When no changes are observed in the chromatogram, the reactive mixture is allowed to cool down to room temperature. 2-(2-cyano-2-(10-methylacridin-9(10H)-ylidene)acetamido)ethyl methacrylate (D) may be isolated by known methods, for instance after passing through a short silica gel column.

Example 4—Synthesis of 2-(2-cyano-2-(10,10-dioxido-9H-thioxanthen-9-ylidene)acetamido)ethyl methacrylate (E) as Shown in Scheme 5

Scheme 5

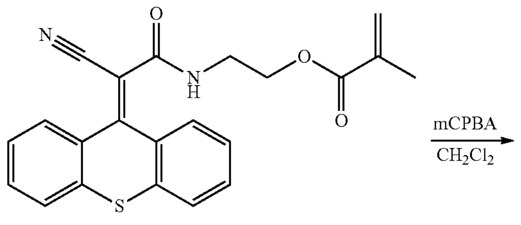

(B)

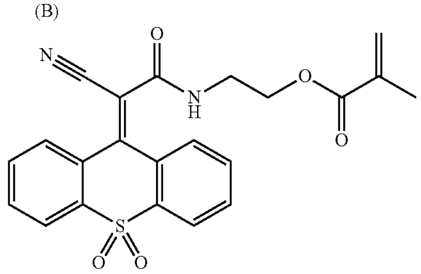

(E)

To a chilled solution of 2-(2-cyano-2-(9H-thioxanthen-9-ylidene)acetamido)ethyl methacrylate (B) (2.0 grams, 5.2 mmol) in dichloromethane, 2.32 grams of m-chloroperbenzoic acid (75% purity, ~2 eq., mCPBA) were added. The mixture was stirred cold for one hour and then allowed to warm up to room temperature. The solution lost its yellow color as the reaction proceeded, and a white solid crystallized or precipitated out of solution. The volatiles were evaporated under reduced pressure. The residue was re-dissolved in ethyl acetate and extracted with dilute aqueous base, followed by dilute aqueous saline solutions. The organic layer was separated, and the solvent removed by rotary evaporation under reduced pressure. The residue was washed with hexanes over a fritted glass funnel and vacuum dried. The UV-VIS transmission spectrum of a 0.2 mM methanolic solution of Compound E is shown in FIG. 1. $^1H$ NMR (500 MHz, $CDCl_3$) δ 1.85 (3H, s, $CH_3$), 3.35 (1H, m, $CH_2NH$), 3.61 (1H, m, $CH_2NH$), 3.81 (1H, m, $CH_2OC{=}O$), 4.05 (1H, m, $CH_2OC{=}O$), 5.55 (1H, m, vinylic), 5.95 (1H, m, vinylic), 6.35 (1H, bs, NH), 7.5-7.75 (5H, m, Ar—H), 8.03 (2H, t, Ar—H), 8.12 (1H, d, Ar—H).

Example 5—Synthesis of 2-(2-cyanoacetamido)ethyl methacrylamide (F) and N-(2-(2-cyano-2-(9H-thioxanthen-9-ylidene)acetamido)ethyl)methacrylamide (G) as Shown in Scheme 6

Scheme 6

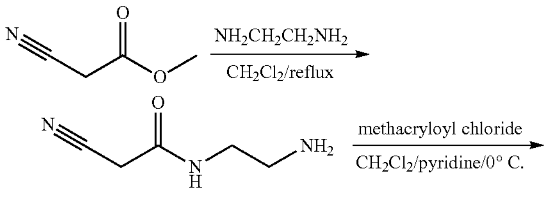

-continued

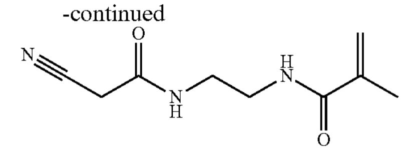

(F)

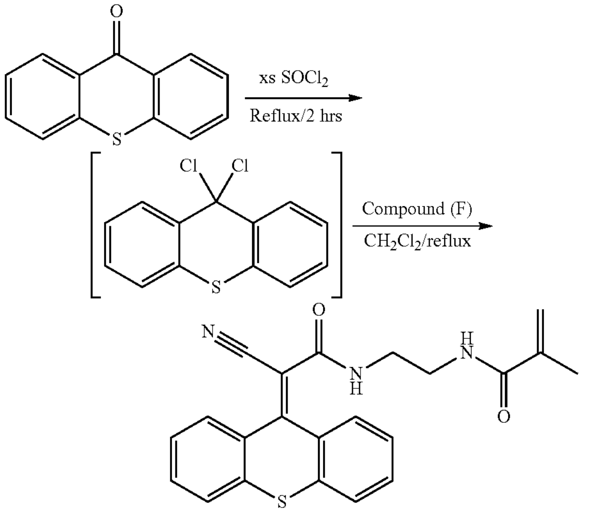

(G)

Methyl cyanoacetate (22 grams, 0.22 mole) and 250 mL of dichloromethane were stirred in a 3 neck, 500 mL round bottom flask under equipped with a reflux condenser under a nitrogen environment. The solution is cooled in a water bath and 1,2-diaminoethane (12 grams, 0.2 mole, ~0.9 eq.) added to the mixture. As the reaction progresses, the mixture appears more and more heterogenous, with the product crashing out of solution. After four hours of stirring at room temperature, the volatiles are evaporated under reduced pressure and the residue is washed with ethyl acetate over a fritted glass funnel and dried at 50° C. prior to further use. $^1$H NMR (500 MHz, $D_2O$) δ 2.74 (2H, t, $CH_2NH_2$), 3.29 (2H, t, $CH_2NH$), 3.38 (2H, s, $CH_2CN$).

2-aminoethyl cyanoacetamide (12.7 g, 0.1 mole) and 12.0 grams of sodium carbonate are stirred in 150 mL of methanol while being chilled in an ice bath. Methacryloyl chloride (11.5 g, 1.1 eq.) is added to the suspension in a dropwise manner, while maintaining the reaction temperature below 30° C. at all times. Once the reaction is complete, evaporate all volatiles under reduced pressure, redissolve the product in acetonitrile and filter the solution to remove all the salts present. Evaporate the acetonitrile under reduced pressure and wash the resulting solids with ethyl acetate over a fritted glass funnel to obtain the desired 2-(2-cyanoacetamido)ethyl methacrylamide (F). $^1$H NMR (500 MHz, $CD_3OD$) δ 1.86 (3H, s, $CH_3$), 3.22-3.26 (4H, m, NH, $CH_2CN$), 3.29 (4H, m, $CH_2NH$), 5.31 (1H, m, vinylic), 5.63 (1H, m, vinylic).

A mixture of thioxanthone (4.24 grams, 0.02 mole) and 8 mL of thionyl chloride (13.12 grams, ~0.11 mole) was gently refluxed under a nitrogen atmosphere with constant stirring. After two hours of heating, the solution was evaporated to dryness under reduced pressure, ensuring that all unreacted thionyl chloride was removed. 2-(2-cyanoacetamido)ethyl methacrylamide (F) (4.2 grams, ~1.1 eq.) and 20 mL of degassed methylene chloride were added to the flask, and the mixture was gently refluxed for 3 hours under a nitrogen environment, while monitoring the progress by TLC. The volatiles were evaporated under reduced pressure, and the organics are washed with ethyl acetate. Large quantities of a precipitate enriched with the major product were observed. The suspension was filtered, and the residual solids washed with ethyl acetate prior to drying in a vacuum oven. The UV-VIS transmission spectrum of a 0.2 mM methanolic solution of Compound G is shown in FIG. 2. $^1$H NMR (500 MHz, $CDCl_3$) δ 1.89 (3H, s, $CH_3$), 3.26 (2H, m, $CH_2NH$), 3.32 (2H, m, $CH_2NH$), 5.33 (1H, m, vinylic), 5.68 (1H, m, vinylic), 6.63 (1H, m, NH), 6.49 (1H, m, NH), 7.25 (1H, m, Ar—H), 7.33 (1H, dt, Ar—H), 7.39 (2H, m, Ar—H), 7.51-7.59 (3H, m, Ar—H), 8.05 (1H, m, Ar—H).

Example 6—N-(2-(2-cyano-2-(10-methylacridin-9(10H)ylidene)acetamido)ethyl) methacrylamide (H) as Shown in Scheme 7

Scheme 7

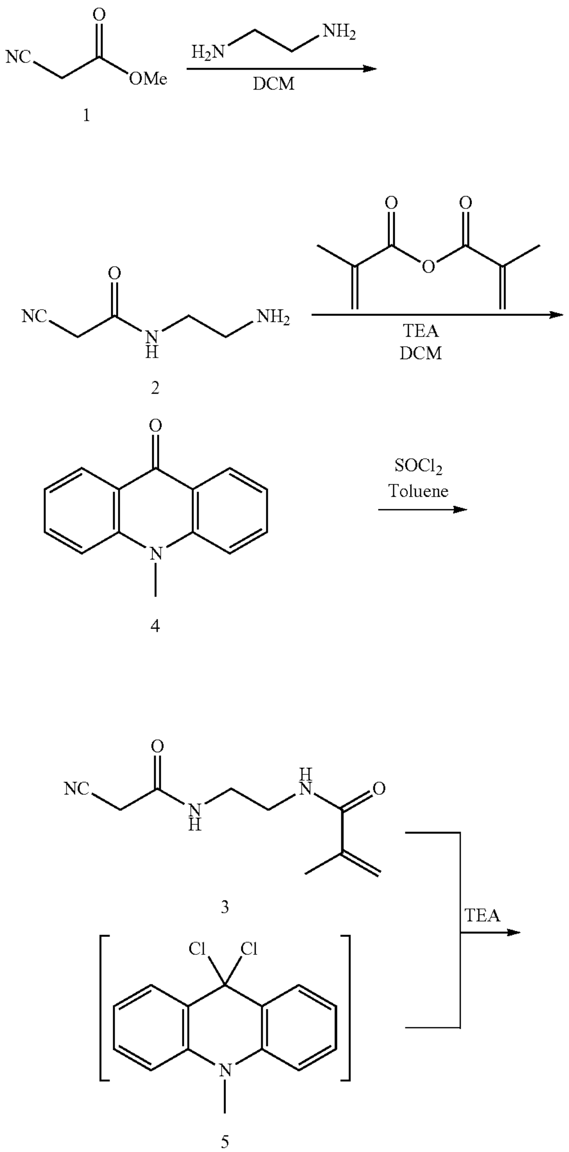

-continued

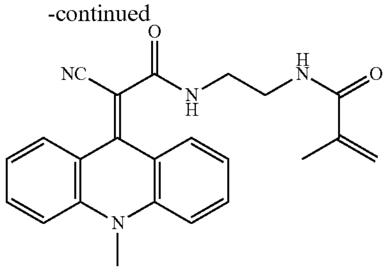

(H)

N-(2-Aminoethyl)-2-cyanoacetamide (2): Compound 1 (30 g, 303 mmol, 1.0 equiv) was added to a solution of ethylene diamine (54.5 g, 909 mol, 3 equiv) in dichloromethane (600 mL) at −20° C. over 30 minutes. The reaction was warmed to room temperature over 2 hours and stirred for 3 hours, at which point LC-MS indicated the reaction was complete. The resulting precipitate was filtered and washed with dichloromethane (2×100 mL) to give compound 2 (25 g, 66% yield, >95% purity) as a white solid.

N-(2-(2-Cyanoacetamido)ethyl)methacrylamide (3): A solution of methylacrylic anhydride (41 g, 264 mmol, 1.3 equiv) and triethylamine (40 mL, 287 mmol, 1.3 equiv) in dichloromethane (300 mL) was stirred at room temperature for 1 hour. The reaction was cooled to 0° C. and compound 2 (28 g, 220 mmol, 1.0 equiv) was added portionwise to the reaction mixture at 0° C. The reaction was warmed to room temperature and stirred for 5 hours, at which point LC-MS indicated the reaction was complete. The resulting precipitate was filtered and washed with dichloromethane (2×100 mL) to give compound 3 (25.1 g, 60% yield, >95% purity) as a white solid.

9,9-Dichloro-10-methyl-9,10-dihydroacridine (5): Compound 4 (10 g, 4.85 mmol, 1.0 equiv) in thionyl chloride (200 mL, 2.75 mol, 55 equiv) was stirred at 60° C. for 2 hours, at which point $^{1}$H-NMR indicated the reaction was complete. The thionyl chloride was removed under reduced pressure. The residue was azeotroped with toluene (2×20 mL) to give crude compound 5 as a yellow solid (12.5 g), which was used subsequently.

N-(2-(2-Cyano-2-(10-methylacridin-9(10H)-ylidene)acetamido)ethyl) methacryl amide (H): Triethylamine (20 mL, 143 mmol, 3.0 equiv) was added dropwise to a solution of the crude compound 5 (12.5 g, 48.5 mmol, 1.0 equiv) and compound 3 (9.33 g, 48.5 mmol. 1.0 equiv) in 1 to 1 mixture of dichloromethane and acetonitrile (200 mL) at 0° C. over 30 minute. The reaction was warmed to room temperature and stirred for 2 hours, at which point LC-MS indicated the reaction was complete. The mixture was passed through a plug of silica gel (150 g), eluting with dichloromethane (500 mL). The organics were concentrated under reduced pressure. The residue was purified over silica gel (800 g), eluting with ethyl acetate, to give compound (H) as a yellow solid. The solid was triturated with methyl tert-butyl ether (2×200 mL) for 2 hours. The solid was collected by filtration and triturated with chloroform (50 mL) for 30 minutes to give the pure compound (H) (11.9 g, 60% yield from two steps, 97.5% purity) as a yellow solid.

The UV-VIS transmission spectrum of a 0.2 mM methanolic solution of Compound H is shown in FIG. 2. $^{1}$H NMR (500 MHz, DMSO-$d_6$) δ 1.87 (3H, m, $CH_3$), 3.15-3.20 (4H, m, $CH_2NH$), 3.72 (3H, s, $CH_3N$), 5.36 (1H, s, vinylic), 5.68 (1H, m, vinylic), 7.14 (1H, bt, NH), 7.29 (1H, bt, NH, 7.49-7.65 (4H, m, Ar—H), 8.02-8.81 (4H, Ar—H).

Example 7—Synthesis of 2-(2-cyanoacetamido) ethyl acrylamide (I) and N-(2-(2-cyano-2-(9H-xanthen-9-ylidene)acetamido)ethyl)acrylamide (J) as Shown in Scheme 8

Scheme 8

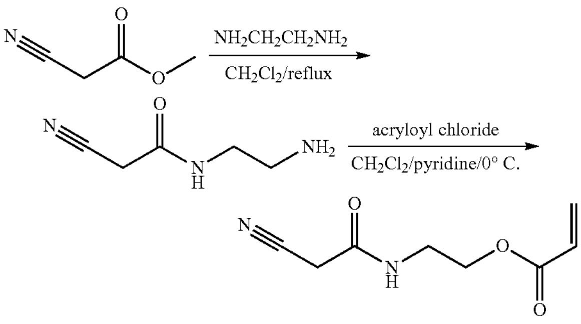

(I)

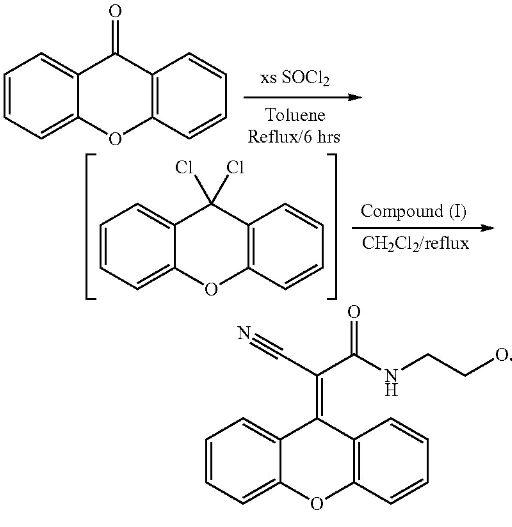

(J)

2-(2-Cyanoacetamido)ethyl acrylamide (I) was prepared by the same methodology as used for 2-(2-cyanoacetamido) ethyl methacrylate (F). 2-aminoethyl cyanoacetamide (12.7 g, 0.1 mole) and 12.0 grams of sodium carbonate are stirred in 150 mL of methanol while being chilled in an ice bath. Acryloyl chloride (9.9 g, 1.1 eq.) is added to the suspension in a dropwise manner, while maintaining the reaction temperature below 30° C. at all times. Once the reaction is complete, evaporate all volatiles under reduced pressure, redissolve the product in acetonitrile and filter the solution to remove all the salts present. Evaporate the acetonitrile under reduced pressure and wash the resulting solids with ethyl acetate over a fritted glass funnel to obtain the desired 2-(2-cyanoacetamido)ethyl acrylamide(I). $^{1}$H NMR (500 MHz, $CD_3OD$) δ 3.22-3.31 (8H, m, NH, $CH_2$), 5.59 (1H, dd, vinylic), 6.14 (2H, dd, vinylic).

A mixture of xanthone (3.92 grams, 0.02 mole) and 5 mL of thionyl chloride (8.2 grams, ~0.07 mole) in 10 mL of toluene was gently refluxed under a nitrogen atmosphere with constant stirring. After six hours of heating, the solution cooled and volatiles were evaporated under reduced pressure, ensuring that all unreacted thionyl chloride was removed from the system. 2-(2-cyanoacetamido)ethyl acrylamide (I) (3.8 grams, ~1.05 eq.) and 20 mL of methylene chloride were added to the flask, and the mixture was gently refluxed for 3 hours under a nitrogen environment, while monitoring the progress by TLC. Volatile components were evaporated under reduced pressure. The residue was washed with warm ethyl acetate and filtered over a fritted glass funnel. The filter cake was washed with additional ethyl acetate, followed by water. The light-yellow solid was dried in a vacuum oven. The UV-VIS transmission spectrum of a 0.2 mM methanolic solution of Compound J is shown in FIG. 2. $^1$H NMR (500 MHz, DMSO-$d_6$) δ 3.15-3.25 (4H, m, $CH_2$), 5.62 (1H, dd, vinylic), 6.08-6.23 (2H, m, vinylic), 7.32-7.75 (1H, dt, Ar—H), 7.46-7.72 (6H, Ar—H), 8.17 (1H, bt, NH), 8.34 (1H, dd, Ar—H), 8.88 (1H, bt, NH).

Example 8—Synthesis of 2-(2-cyanoacetoxy)ethyl methacrylate (K) and 2-(2-cyano-2-(9H-thioxanthen-9-ylidene)acetoxy)ethyl methacrylate (L) as Shown in Scheme 9

Scheme 9

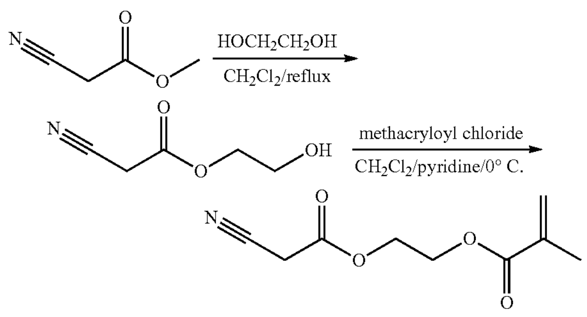

(K)

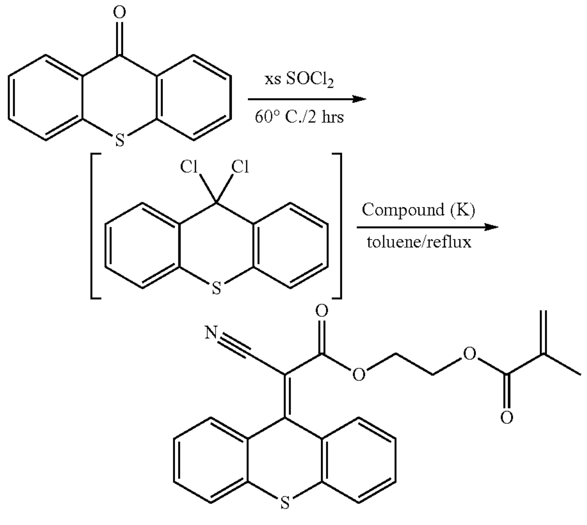

(L)

2-(2-Cyanoacetoxy)ethyl methacrylate (K) was prepared by coupling cyanoacetic acid with 2-hydroxyethyl methacrylate as follows. Cyanoacetic acid (9 g, 0.106 mole) and 13 g of 2-hydroxyethyl methacrylate (HEMA, are stirred in 250 mL of dichloromethane, and ethyl dimethylaminopropyl carbodiimide hydrochloride (EDC) is added to the suspension in 4 batches of 5 grams each (20 g, 0.104 mole). The mixture gradually becomes more homogenous as the less polar derivative is formed and volatiles are evaporated under reduced pressure after completion of the reaction. The product is redissolved in a 25:75 mixture of ethyl acetate and hexanes by weight and extracted several times with deionized water to remove any residual salts and unreacted HEMA. A small amount of 4-methoxyhydroquinone (<20 mg) is added to the organic layer and the product is obtained pure after evaporation of the solvents under reduced pressure. $^1$H NMR (500 MHz, $CDCl_3$) δ 1.92 (3H, m, $CH_3$), 3.47 (2H, S, $NCCH_2$), 4.36 (2H, m, $OCH_2$), 4.44 (2H, m, $OCH_2$), 4.59 (1H, m, vinylic), 6.10 (1H, m, vinylic).

A mixture of thioxanthone (4.24 grams, 0.02 mole) and 8 mL of thionyl chloride (13.12 grams, ~0.11 mole) was gently refluxed under a nitrogen atmosphere with constant stirring. After two hours of heating, the solution was evaporated to dryness under reduced pressure, ensuring that all unreacted thionyl chloride was removed. A solution of 2-(2-cyanoacetoxy)ethyl methacrylate (K) (4.33 grams, ~1.1 eq.) in 20 mL of degassed methylene chloride was added to the flask, and the mixture was gently refluxed for 3 hours under a nitrogen environment, while monitoring the progress by TLC. The residue was washed with methanol to remove most of the unreacted starting thioxanthone, reconcentrated, and the crude product was purified by chromatography over a silica gel plug and vacuum dried overnight. The UV-VIS transmission spectrum of a 0.2 mM solution of Compound L in dichloromethane is shown in FIG. 2. $^1$H NMR (500 MHz, $CDCl_3$) δ 1.92 (3H, s, $CH_3$), 4.36 (2H, m, $CH_2$), 4.44 (2H, m, $CH_2$), 5.59 (1H, m, vinylic), 6.10 (1H, m, vinylic), 7.24-7.62 (7H, m, Ar—H), 8.1 (1H, m, Ar—H).

Example 9—Silicone Hydrogel Formulations Comprising Compound (B)

Reactive monomer mixtures were prepared composed of 77 weight percent of the formulations listed in Table 4 and 23 weight percent of the diluent D3O. The reactive monomer mixtures were individually filtered through a 3 μm filter using a stainless-steel syringe under pressure.

TABLE 4

| Component | Ex 9A (weight %) | Ex 9B (weight %) | Ex 9C (weight %) | Ex 9D (weight %) |
|---|---|---|---|---|
| mPDMS 1000 | 30.85 | 30.7 | 30.55 | 30.39 |
| SiMAA | 27.61 | 27.48 | 27.35 | 27.2 |
| DMA | 23.76 | 23.6 | 23.53 | 23.4 |
| HEMA | 5.94 | 5.91 | 5.88 | 5.85 |
| TEGDMA | 1.52 | 1.52 | 1.51 | 1.5 |
| PVP K90 | 6.9 | 6.9 | 6.8 | 6.8 |
| Irgacure 1870 | 0.35 | 0.34 | 0.34 | 0.34 |
| RB247 | 0.02 | 0.02 | 0.02 | 0.02 |
| Compound (B) | 3.05 | 3.03 | 3.02 | 3 |
| Norbloc ® | 0 | 0.5 | 1 | 1.5 |
| Σ Components | 100 | 100 | 100 | 100 |

Formulations 9A-9D were degassed at ambient temperature by applying vacuum (40 torr) for 45 minutes. Then, in a glove box with a nitrogen gas atmosphere and less than about 0.1-0.2 percent oxygen gas, about 75 μL of the reactive mixture were dosed using an Eppendorf pipet at room temperature into the FC made of 90:10 (w/w) Zeonor/TT blend. The BC made of 90:10 (w/w) Z:TT blend was then placed onto the FC. The molds were equilibrated for a minimum of twelve hours in the glove box prior to dosing.

Pallets containing eight mold assemblies each were transferred into an adjacent glove box maintained at 65° C., and the lenses were cured from the top and the bottom for 15 minutes using 435 nm LED lights having an intensity of about 2 $mW/cm^2$ at the tray's location.

The lenses were manually de-molded with most lenses adhering to the FC and released by suspending the lenses in about one liter of 70 percent IPA for about one hour, followed by soaking two more times with fresh 70 percent TPA for 30 minutes; then two times with fresh DIW for 15 minutes; then two time with packing solution for 30 minutes. The lenses were equilibrated and stored in borate buffered packaging solution. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all of the lenses without defects and transition from diluent swollen networks to the packaging solution swollen hydrogels. The average center thickness of each lens set was measured; 9A=87.7 microns, 9B=85.3 microns, 9C=87.3 microns, and 9D=85.7 microns.

FIGS. 3-5 show the UV-VIS spectra of the lenses made from Formulations 9A-9D demonstrating that compound (B) or combinations of compound (B) and Norbloc® may provide complete or nearly complete absorption between 300 nm and 400 nm with some absorption in the high energy visible region between 400 nm and 450 nm.

Example 10—Silicone Hydrogel Formulations Comprising Compounds (B) and (C)

Reactive monomer mixtures were prepared composed of 77 weight percent of the formulations listed in Table 5 and 23 weight percent of the diluent D3O. The reactive monomer mixtures were individually filtered through a 3 μm filter using a stainless-steel syringe under pressure.

TABLE 5

| Component | Ex 10A (weight %) | Ex 10B (weight %) | Ex 10C (weight %) | Ex 10D (weight %) |
|---|---|---|---|---|
| mPDMS 1000 | 30.87 | 30.69 | 30.51 | 30.33 |
| SiMAA | 27.66 | 27.5 | 27.34 | 27.18 |
| DMA | 23.83 | 23.7 | 23.57 | 23.44 |
| HEMA | 5.98 | 5.95 | 5.92 | 5.89 |
| TEGDMA | 1.5 | 1.5 | 1.5 | 1.5 |
| PVP K90 | 6.8 | 6.8 | 6.8 | 6.8 |
| Irgacure 1870 | 0.34 | 0.34 | 0.34 | 0.34 |
| RB247 | 0.02 | 0.02 | 0.02 | 0.02 |
| Compound (B) | 0 | 3 | 3 | 3 |
| Compound (C) | 3 | 0.5 | 1 | 1.5 |
| Σ Components | 100 | 100 | 100 | 100 |

Formulations 10A-10D were degassed at ambient temperature by applying vacuum (40 torr) for 45 minutes. Then, in a glove box with a nitrogen gas atmosphere and less than about 0.1-0.2 percent oxygen gas, about 75 μL of the reactive mixture were dosed using an Eppendorf pipet at room temperature into the FC made of 90:10 (w/w) Zeonor/TT blend. The BC made of 90:10 (w/w) Z:TT blend was then placed onto the FC. The molds were equilibrated for a minimum of twelve hours in the glove box prior to dosing. Pallets containing eight mold assemblies each were transferred into an adjacent glove box maintained at 65° C., and the lenses were cured from the top and the bottom for 15 minutes using 435 nm LED lights having an intensity of about 2 $mW/cm^2$ at the tray's location.

The lenses were manually de-molded with most lenses adhering to the FC and released by suspending the lenses in about one liter of 70 percent IPA for about one hour, followed by soaking two more times with fresh 70 percent IPA for 30 minutes; then two times with fresh DIW for 15 minutes; then two time with packing solution for 30 minutes. The lenses were equilibrated and stored in borate buffered packaging solution. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all of the lenses without defects and transition from diluent swollen networks to the packaging solution swollen hydrogels. The average center thickness of each lens set was measured; 10A=93.7 microns, 10B=93.7 microns, 10C=95.3 microns, and 10D=92.3 microns.

FIGS. 6-8 show the UV-VIS spectra of the lenses made from Formulations 10A-10D demonstrating that combinations of compounds (B) and (C) may provide complete or nearly complete absorption between 300 nm and 400 nm with some absorption in the high energy visible region between 400 nm and 450 nm. The figures also demonstrate that compound (C) alone provides absorption at various wavelength ranges.

Example 11

Lenses were made using the reactive monomer mixture comprising the components listed as 9D in Table 4 and same curing and hydration steps except that the oxygen gas concentration in the glove box was less than 0.5%. Lenses were packaged in glass vials containing PS and then placed either on a window sill with direct sunlight (11A) or on top of a cabinet without exposure to direct sunlight, only indoor lighting (11B). Controls were stored in the dark. After 3, 5, 9, 15, and 21 weeks of exposure, UV-Visible transmission spectra of the lenses were measured as shown in FIG. 9 and FIG. 10.

For lenses exposed to direct sunlight, the absorption of high energy visible light between 400 nm and 450 nm did not change over time. There were minor (about 1%) changes in the UV-VIS transmission spectra between 450 nm and 700 nm over the duration of the study.

For lenses exposed to indoor lighting, the absorption of high energy visible light between 400 nm and 450 nm did not change over time. The UV-VIS transmission spectra did not change more than about 2% or 3% between 450 nm and 700 nm over the duration of the study.

Example 12

61 subjects were enrolled, and 58 completed as cohort. 31 subjects were 18-39 yrs of age (mean=29.6±5.6). 27 subjects were 40-65 yrs of age (mean=50.1±8.1). A double-masked contralateral design was used. Participants randomly wore a short wave-filtering (SW-filtering) contact lens on one eye and a clear control lens on the other eye. A clear control lens may transmit at least 85% across the visible spectrum from 400 to 700 nm. The clear control, lens may comprise a lens of the invention obtained from a reactive mixture that includes mPDMS 1000, SiMAA, DMA, HEMA, Norbloc, PVP K90, and the like. The SW-filtering contact lens filtered light in the visible spectrum from 400 to 500 nm. Subjects then mixed three primaries (including a short-wave primary, strongly within the absorbance of the test lens) until a perceived perfect neutral white was achieved with each eye. Color appearance was quantified using chromaticity coordinates measured with a spectral radiometer within a custom-built tricolorimeter. Disruptions from normal trichromatic color vision are represented as alterations in the relative amounts of the color primaries used to create a perfect perceived neutral white. Because each variable is on a continuous scale, even small alterations in color appearance can be assessed.

Figure 14:
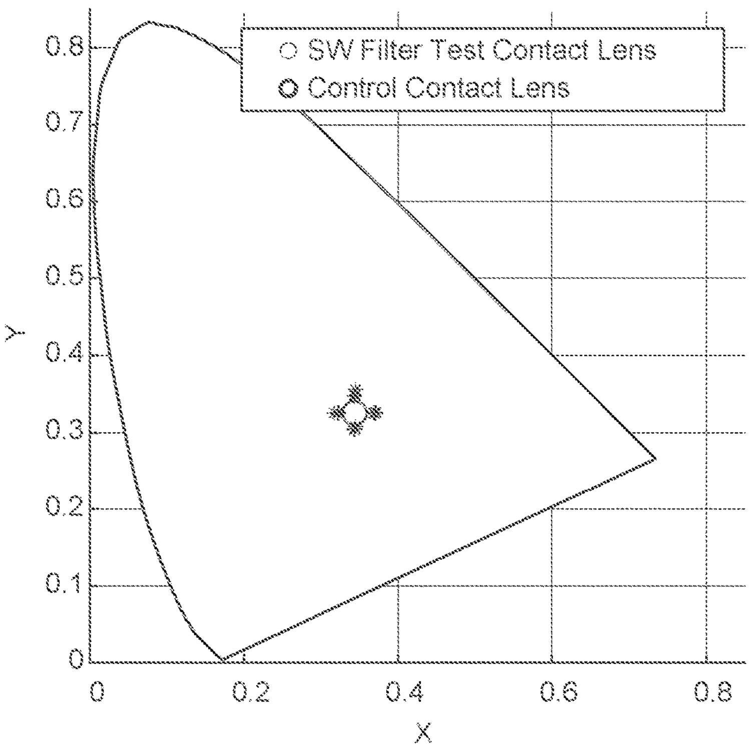
FIG. 14 displays subjective white points of all subjects according to the present disclosure.
Figure 15A:
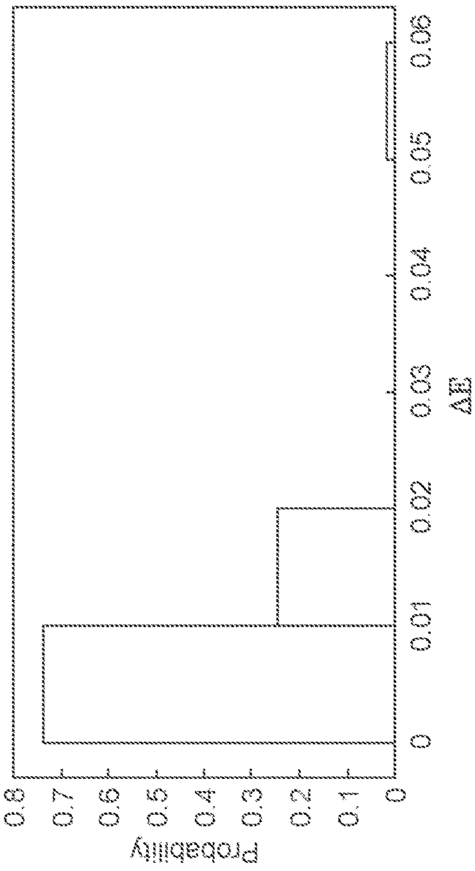
FIGS. 15A-15D display histograms of the within subject differences in subjective white points through color difference (FIG. 15A), direction (FIG. 15B), change in x (FIG. 15C), and change in y (FIG. 15D).
Figure 15B:
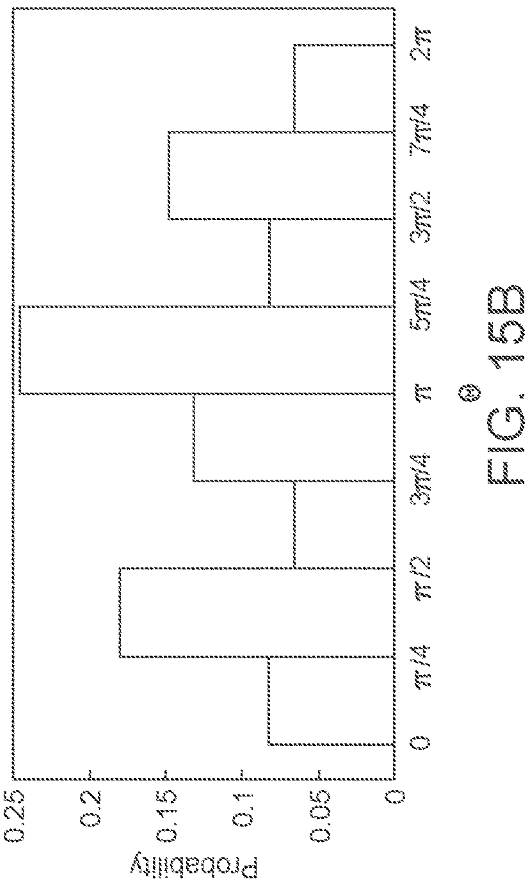
Figure 15C:
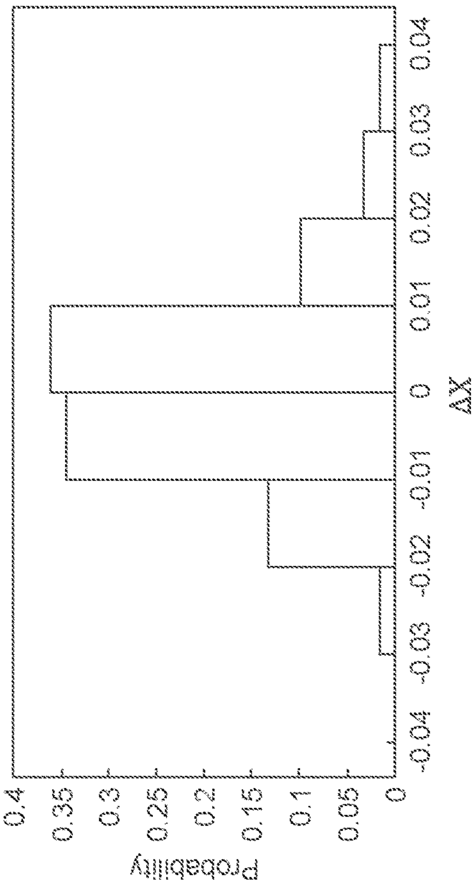
Figure 15D:
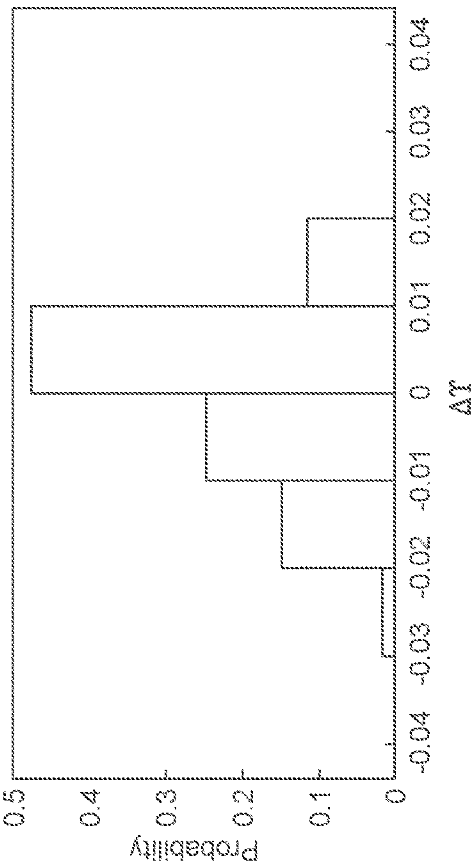

Overall, the chromaticity coordinates of eyes with the SW-filtering Test contact lens (n=58; x=0.345, y=0.325, u'=0.222, v'=0.470) and clear contact lens (n=58; x=0.344, y=0.325, u'=0.223, v'=0.471) were not significantly different (FIG. 14, Table 6). This was also true when the subjects were separated by age into young (18-39 yrs, n=31) and older (40-65 yrs, n=27) groups. Within subject differences indicate that the vast majority of subjects had a color difference, ΔE, less than 0.01 with no systematic bias in the color direction, θ. Similarly, within subject differences in x, Δx, and y, Δy, were consistently less than 0.02 (FIGS. 15A-15D). We also measured the energy needed to make the matches (illuminance) and found no differences across lens types or age (Table 7).

Results indicate that imparting a subtle tint to a contact lens in the violet/blue region, as in the SW-filtering lens, does not alter color appearance in normal trichromatic subjects, regardless of age.

TABLE 6

| | Age Group: 18 to 39 years | | Age Group: 40 to 65 years | | Total | |
|---|---|---|---|---|---|---|
| | Test N = 31 | Control N = 31 | Test N = 27 | Control N = 27 | Test N = 58 | Control N = 58 |
| | Color Appearance - u' | | | | | |
| Mean | 0.222 | 0.223 | 0.223 | 0.223 | 0.222 | 0.223 |
| (SD) | (0.004) | (0.005) | (0.007) | (0.005) | (0.005) | (0.005) |
| Median | 0.222 | 0.222 | 0.223 | 0.223 | 0.222 | 0.222 |
| Min-Max | 0.212-0.233 | 0.212-0.236 | 0.210-0.240 | 0.213-0.232 | 0.210-0.240 | 0.212-0.236 |
| | Color Appearance - v' | | | | | |
| Mean | 0.471 | 0.471 | 0.468 | 0.470 | 0.470 | 0.471 |
| (SD) | (0.007) | (0.007) | (0.015) | (0.007) | (0.011) | (0.007) |
| Median | 0.472 | 0.470 | 0.470 | 0.470 | 0.471 | 0.470 |
| Min-Max | 0.459-0.486 | 0.459-0.485 | 0.400-0.486 | 0.457-0.486 | 0.400-0.486 | 0.457-0.486 |
| | Color Appearance - x | | | | | |
| Mean | 0.345 | 0.344 | 0.345 | 0.345 | 0.345 | 0.344 |
| (SD) | (0.010) | (0.010) | (0.012) | (0.011) | (0.011) | (0.011) |
| Median | 0.343 | 0.344 | 0.344 | 0.344 | 0.343 | 0.344 |
| Min-Max | 0.332-0.368 | 0.322-0.371 | 0.317-0.366 | 0.325-0.370 | 0.317-0.368 | 0.322-0.371 |
| | Color Appearance - y | | | | | |
| Mean | 0.326 | 0.325 | 0.324 | 0.325 | 0.325 | 0.325 |
| (SD) | (0.010) | (0.010) | (0.011) | (0.012) | (0.010) | (0.011) |
| Median | 0.326 | 0.325 | 0.324 | 0.323 | 0.325 | 0.325 |
| Min-Max | 0.308-0.349 | 0.308-0.348 | 0.308-0.353 | 0.304-0.346 | 0.308-0.353 | 0.304-0.348 |

TABLE 7

| | Age Group: 18 to 39 years | | Age Group: 40 to 65 years | | Total | |
|---|---|---|---|---|---|---|
| | Test N = 31 | Control N = 31 | Test N = 27 | Control N = 27 | Test N = 58 | Control N = 58 |
| | Illuminance (lux) | | | | | |
| Mean | 113 | 113 | 116 | 116 | 114 | 114 |
| (SD) | (6) | (6) | (5) | (6) | (5) | (6) |
| Median | 115 | 113 | 115 | 117 | 115 | 115 |
| Min-Max | 103-125 | 102-123 | 104-126 | 103-128 | 104-126 | 102-128 |

Example 13

Five sets of hyperspectral images were used to assess the effect of filters on the color perception of natural scenes. Four image sets were obtained from the literature (Nascimento et al. (2002), Foster et al. (2006), Parraga et al. (1998) and Chakrabarti and Zickler (2011)), and one image set was acquired in support of this study. The images sets obtained from the literature were chosen from those available for their high precision and lack of spectral artifacts.

A custom set of hyperspectral images was gathered using a calibrated IQ camera (SPECIM, Oulu, Finland) of scenes created in the lab under controlled lighting, and outdoor scenes. The custom image set consisted of 35 images featuring a mixture of manmade and colored objects, including objects where color discrimination is often critical (e.g. maps, colored markers, flowers, traffic lights, colored threads and cables, and fruit). The spatial resolution of the images was 512×512, and the native spectral resolution was 204 wavebands between 400 and 1000 nm.

Figure 12A:
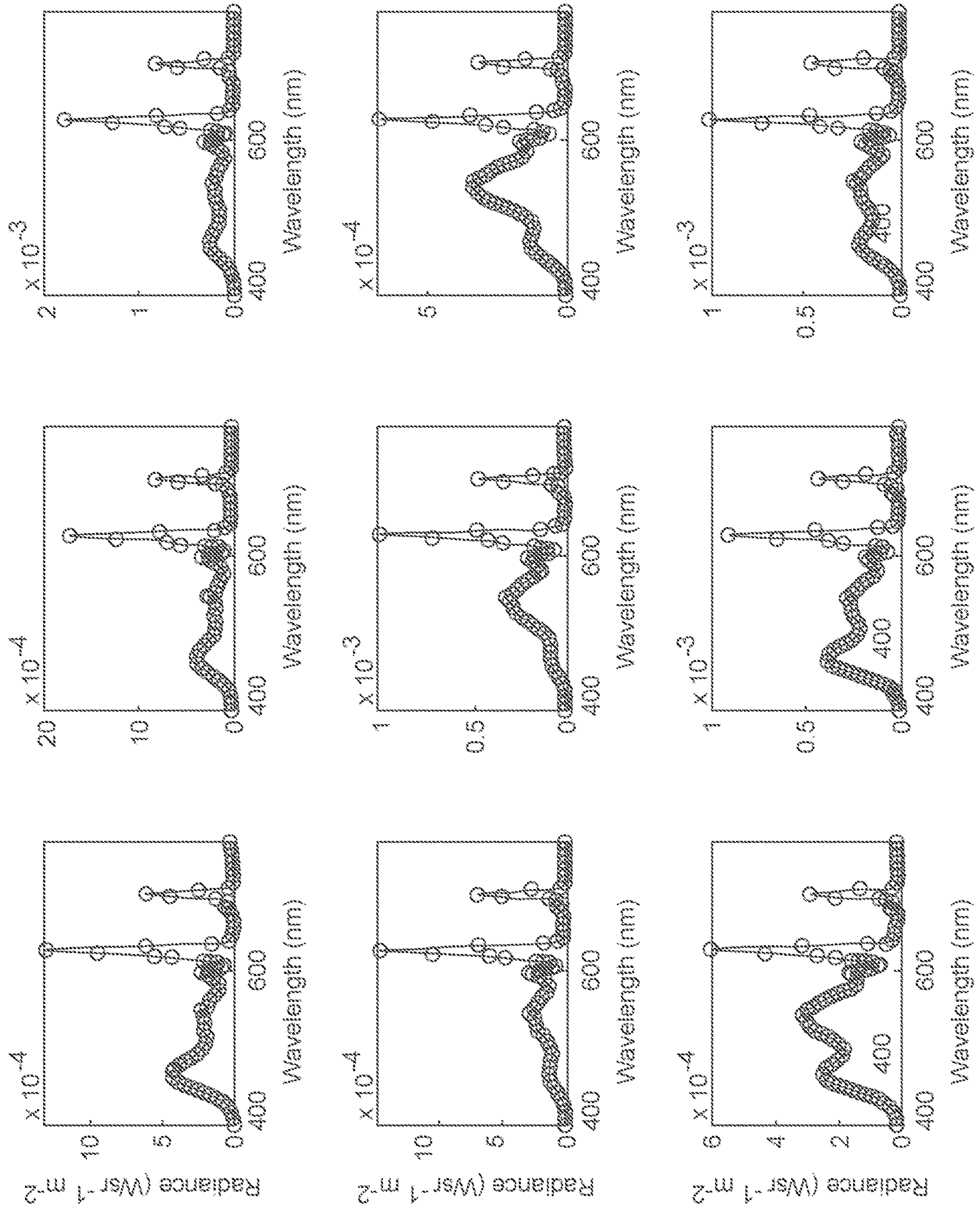
FIGS. 12A-12B display radiance spectra of 9 colored stimuli measured using a PR655 spectroradiometer (FIG. 12A) and McLeod-Boynton chromaticities derived from the PR655 spectroradiometer (FIG. 12B)
Figure 12B:
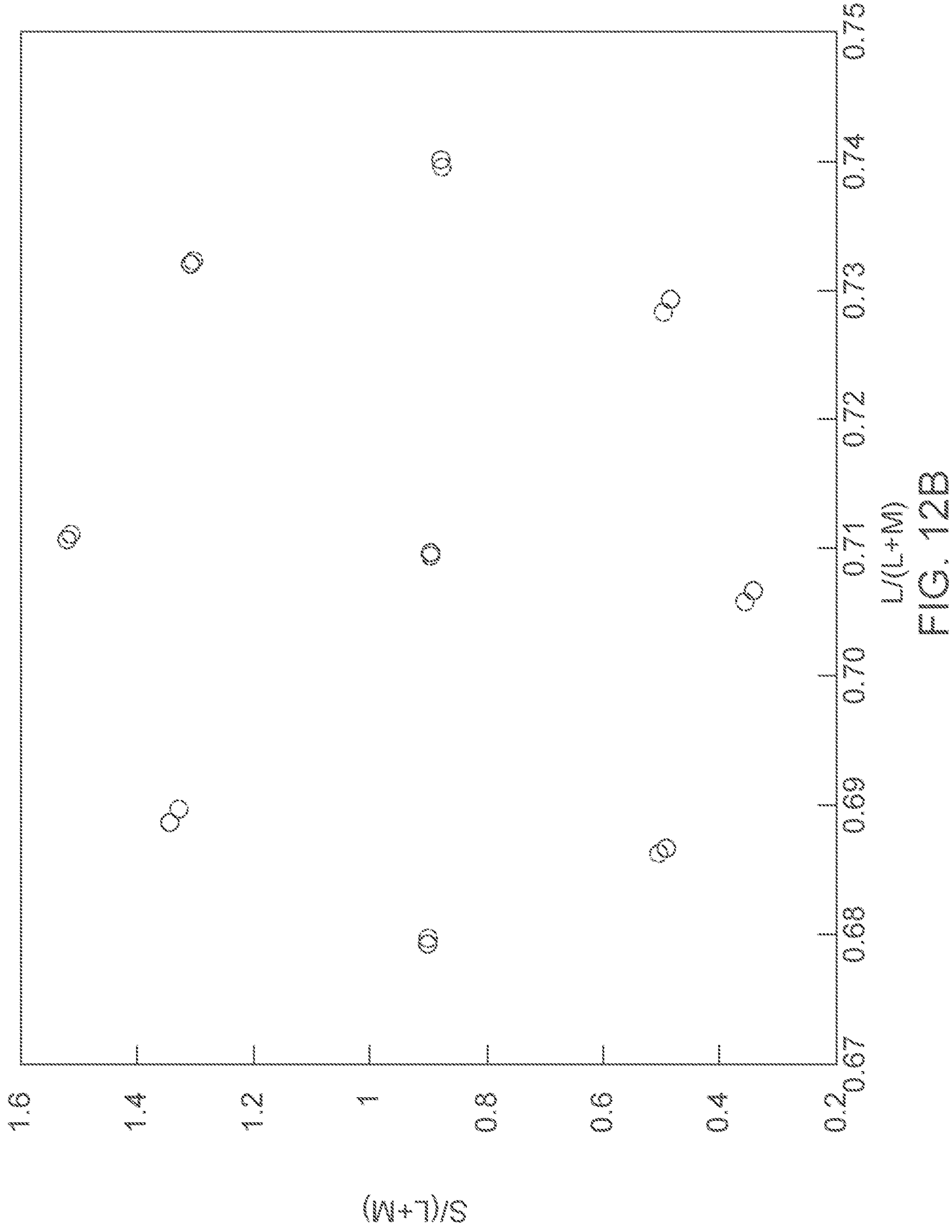

These custom images were calibrated using a PR655 spectroradiometer (PhotoResearch, Chatsworth, CA) and colored stimuli presented on a CRT monitor (Mitsubishi, Tokyo, Japan). By measuring a series of the same stimuli with both the PR655 and the SPECIM IQ, a vector of mean wavelength-specific scaling factors was calculated that allowed the SPECIM's camera-specific intensities to be transformed into radiance units. The calibration was checked using an independent set of stimuli (FIG. 12A), which showed that residual disagreement between devices would be below human color discrimination threshold (FIG. 12B). The calibration accuracy was also checked for broadband stimuli using scenes containing a standard white barium sulphate plaque.

The two sets of publicly available hyperspectral images captured by David Foster et al. (2006) are mostly of outdoor scenes including foliage, flowers, countryside and cityscapes. The images are 820×820 spatially with 33 spectral wavebands between 400 and 720 nm. The Nascimento et al. (2002) dataset consisted of 8 images with reflectance information only (i.e. as if the scenes were imaged under equal energy white). The Parraga et al. (1998) dataset consisted of 29 images of outdoor scenes, including trees, foliage, flowers, bark and soil. The images provided radiance for 31 wavebands between 400 and 700 nm with a spatial resolution of 256×256. The Chakrabarti and Zickler (2011) dataset included 25 'indoor' images and 38 'outdoor' images. Several images were eliminated from Chakrabarti and Zickler's full set because they contained spectral artifacts (camera saturation). The spatial resolution of the images was 1040×1392 with intensities at 31 wavebands between 420 nm and 720 nm. The images were calibrated to account for camera sensitivity but were not radiance calibrated.

Figure 13A:
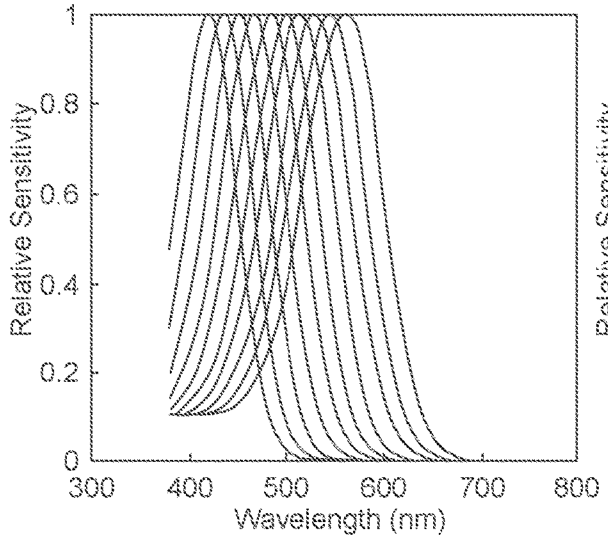
FIGS. 13A-13B display nomograms for simulating cone fundamentals of arbitrary peak sensitivity (FIG. 13A) and for a 20-year-old observer (FIG. 13B).
Figure 13B:
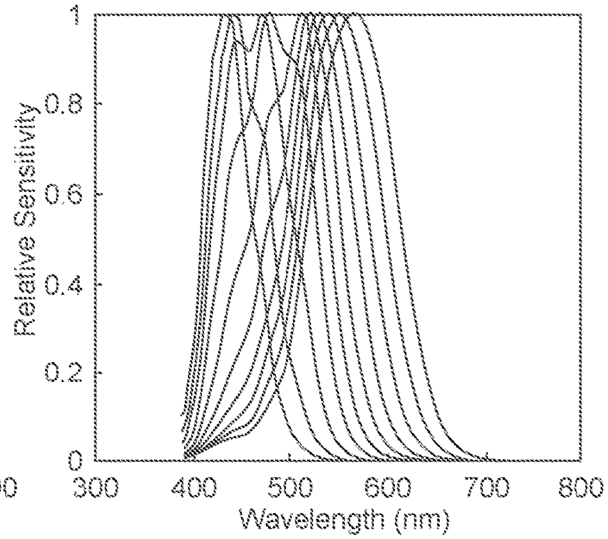

The individual observer model was based on the Stockman and Sharpe (2000) nomogram (FIGS. 13A-13B). The standard normal observer is defined with in vitro peak receptoral sensitivities of 558.9 nm, 530.3 nm and 430.7 nm. The nomogram, showing example normalized cone fundamentals created between 420 nm and 560 nm are shown in FIG. 13A. Additional model features included: macular pigment optical density (OD=0.35); age-dependent lens density function using equations provided by Pokorny et al. (1987), (e.g. 20 years); and receptoral optical density (e.g. 0.38, 0.38 and 0.3 for L, M and S as recommended by Stockman and Sharpe (2000)); and scaling factors for the relative peak heights of the L and M cone fundamentals so that L=1.5M as recommended by Stockman and Sharpe (2000), as shown in FIG. 13B. The scaling factor for the S-cone fundamental is arbitrary.

After defining the observer, each hyperspectral image was transformed to observer-specific LMS values (with and without the additional filter). First, observer-specific matrices of MacLeod-Boynton (1979) chromaticity coordinates were created and translated to center the white point at (0, 0) using an image-specific white point. Gamut changes were then calculated relative to the white point. The impact of the filter was calculated as the difference between the absolute MacLeod-Boynton chromaticity coordinates of the scene with the filter and the absolute MacLeod-Boynton chromaticity coordinates of the scene without the filter. Using the absolute values ensures that any enhancement in chromatic contrast from white (along the bipolar chromaticity dimension) is a positive number in the difference metric, while any reduction in chromatic contrast from white is a negative number. The size of the change in pixel chromatic contrast caused by the filter was quantified as a percentage of 95% of the gamut of the scene without the filter. Simulations were conducted for a range of macular pigment OD (OD=0.2 to 1.3) and lens OD (age=20 to 70) to estimate sensitivity to these parameters.

Figure 16:
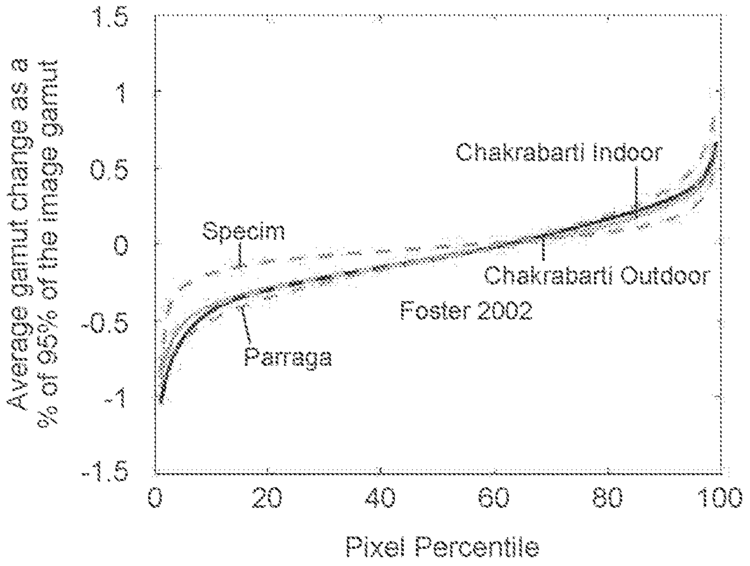
FIG. 16 displays percentile changes in chromatic contrast as a percentage of the original image gamut.
Figure 17A:
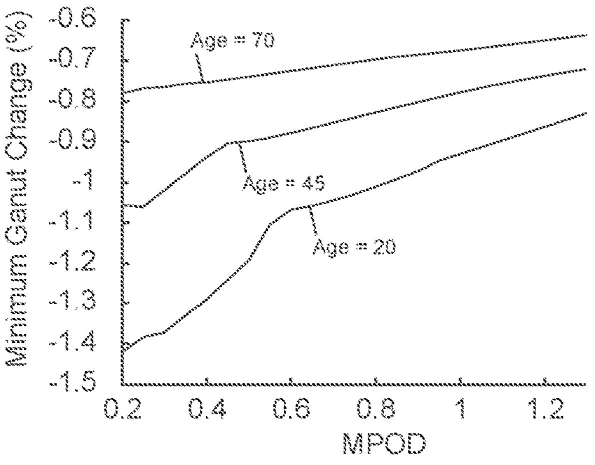
FIGS. 17A-17B display minimum and maximum gamut change as a function of macular pigment optical density (MPOD) and age.
Figure 17B:
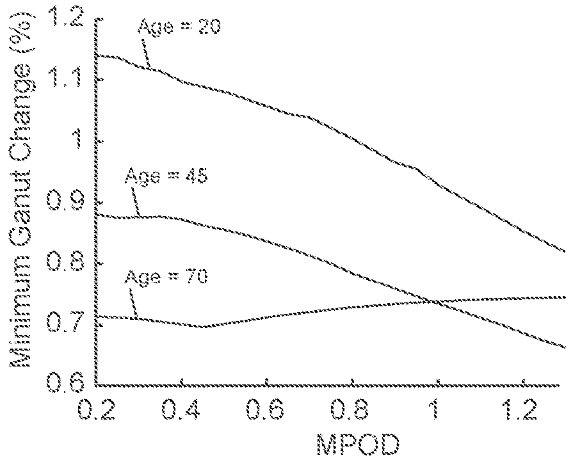

Calculated chromatic contrast changes as a percentage of 95% of the unfiltered image gamut show that the test lens is predicted to cause very little change in gamut. Results vary slightly by scene and dataset such that chromatic contrast for individual pixels is predicted to change by, at most, ~1.4% and +1.1%. Between 1 and 16% of pixels exhibit chromatic contrast reductions of more than 0.5%, and between 1 and 7% of pixels exhibit chromatic contrast enhancements of more than 0.5%. Although the change is minor, between 35% and 67% of pixels exhibit chromatic contrast reductions (FIGS. 16 and 17A-17B). The minimum and maximum gamut change results demonstrate a small effect of both age and MPOD. Namely, younger subjects generally experience more of a gamut change than older subjects and subjects with low MPOD generally experience more of a gamut change than subjects with more MPOD.

As an example, the nominal middle wavelength of the transition band of ophthalmic device in accordance with the present invention is 422 nm. In other words, the filter may nominally blocks 50% or more of HEV light from 422 nm and below. As a further example, a filter may be used to effect an ophthalmic device exhibiting between 1 and 70% transmission from 400 to 429 nm. As a further example, a filter may be used to effect an ophthalmic device transmits from 1 percent to 70 percent of light across a wavelength range of 400 to 409 nm, and from 10 percent to 95 percent of light across a wavelength range of 410 to 424 nm. The exhibited transmission may neglect surface reflectance, also referred to as Fresnel losses or Fresnel reflectance or reflection loss.

Example 14: (Z)-2-(2-cyano-2-(3-hydroxyacridin-9(10H)-ylidene)acetamido)ethyl methacrylate The title compound can be synthesized by analogous procedures to those described above, starting from 3-hydroxyacridone (CAS reg. no. 20168-55-2).

Example 15: 2-(2-cyano-2-(10-methylacridin-9(10H)-ylidene)acetamido)ethyl methacrylate The title compound can be synthesized by analogous procedures to those described above, starting from N-methylacridone (719-54-0).

Example 16: 2-(2-cyano-2-(3,6-dihydroxyacridin-9(10H)-ylidene)acetamido)ethyl methacrylate The title compound can be synthesized by analogous procedures to those described above, starting from 3,6-dihydroxyacridone (122105-95-7).

Example 17: (E)-2-(2-(7H-benzo[c]xanthen-7-ylidene)-2-cyanoacetamido)ethyl methacrylate The title compound can be synthesized by analogous procedures to those described above, starting from benzo[C]xanthone (63154-69-8).

Example 18: (Z)-2-(2-cyano-2-(3-methoxy-9H-xanthen-9-ylidene)acetamido)ethyl methacrylate The title compound can be synthesized by analogous procedures to those described above, starting from 3-methoxyxanthone (3722-52-9).

Example 19: 2-(2-cyano-2-(3,6-dihydroxy-9H-xanthen-9-ylidene)acetamido)ethyl methacrylate The title compound can be synthesized by analogous procedures to those described above, starting from 3,6-dihydroxyxanthone (1214-24-0).

Example 20: (E)-2-(2-cyano-2-(2-methyl-9H-xanthen-9-ylidene)acetamido)ethyl methacrylate The title compound can be synthesized by analogous procedures to those described above, starting from 2-methylxanthone (2680-45-1).

Example 21: (E)-2-(2-cyano-2-(1-hydroxy-9H-xanthen-9-ylidene)acetamido)ethyl methacrylate The title compound can be synthesized by analogous procedures to those described above, starting from 1-hydroxyxanthone (19-41-5).

Example 22: (E)-2-(2-cyano-2-(2,4-dichloro-9H-thioxanthen-9-ylidene)acetamido)ethyl methacrylate The title compound can be synthesized by analogous procedures to those described above, starting from 2,4-dichlorothioxanthone.

Example 23: (E)-2-(2-(2-chloro-9H-thioxanthen-9-ylidene)-2-cyanoacetamido)ethyl methacrylate The title compound can be synthesized by analogous procedures to those described above, starting from 2-chlorothioxanthone.

Example 24: (E)-2-(2-cyano-2-(2-isopropyl-9H-thioxanthen-9-ylidene)acetamido)ethyl methacrylate and (E)-2-(2-cyano-2-(4-isopropyl-9H-thioxanthen-9-ylidene)acetamido)ethyl methacrylate The title compounds can be synthesized as a mixture by analogous procedures to those described above, starting from a mixture of 2 and 4-isopropyl thioxanthone.

Examples 25-27

Contact lenses from the silicone hydrogel formulations shown in Table 8 can be prepared using analogous procedures to those described in Example 6. In these examples, 77 weight percent of the formulations listed in Table 8 are diluted with 23 weight percent of diluent (e.g., D3O).

TABLE 8

| Component | Ex 23 (weight %) | Ex. 24 (weight %) | Ex. 25 (weight %) |
|---|---|---|---|
| OH-mPDMS (n = 15) | 28.00 | 28.50 | 28.00 |
| OH-mPDMS (n = 4) | 25.00 | 25.50 | 25.00 |
| ac-PDMS | 5.00 | 4.00 | 5.00 |
| DMA | 24.00 | 20.00 | 20.00 |
| HEMA | 7.98 | 7.98 | 7.98 |
| Blue HEMA | 0.02 | 0.02 | 0.02 |
| PDMA ($M_w$ = 740 kDa) | 5.00 | 0 | 0 |
| PVP K90 | 0 | 7.00 | 9.00 |
| PVMA ($M_w$ = 570 kDa) | 0 | 2.00 | 0 |
| EGDMA | 0.25 | 0.25 | 0.25 |
| Compound (B) | 3.00 | 3.00 | 3.00 |
| Norbloc ® or compound (C) | 1.50 | 1.50 | 1.50 |
| Irgacure 1870 | 0.25 | 0.25 | 0.25 |
| Σ Components | 100 | 100 | 100 |

We claim:

1. An ophthalmic device that is a free radical reaction product of a reactive mixture comprising:

one or more polymerizable compounds suitable for making the ophthalmic device; and a high energy visible (HEV) light absorbing compound and a UV absorbing compound that is a benzophenone, a benzotriazole, a triazine, a substituted acrylonitrile, or mixtures thereof, wherein the ophthalmic device transmits from 1 percent to 30 percent of light across a wavelength range of 400 to 409 nm, and from 10 percent to 95 percent of light across a wavelength range of 410 to 424 nm, and wherein the ophthalmic device exhibits a change in chromatic contrast of 0.5% or less in 70 to 98% of natural scene content.

2. The ophthalmic device of claim 1, further comprising a second polymerizable high energy light absorbing compound.

3. The ophthalmic device of claim 2, wherein the second polymerizable high energy light absorbing compound is an ultra-violet (UV) absorbing compound.

4. The ophthalmic device of claim 1, wherein the ophthalmic device comprises a contact lens, a corneal onlay, a corneal inlay, an intraocular lens, or an overlay lens.

5. The ophthalmic device of claim 1, wherein the ophthalmic device comprises a hydrogel contact lens.

6. The ophthalmic device of claim 1, wherein the ophthalmic device exhibits a shift in a peak wavelength by 1.6 nm or less and a decrease in amplitude of irradiance by 5.4% on a tristimulus colorimeter's blue primary when compared to a substantially similar ophthalmic device consisting essentially of the one or more polymerizable compounds and without the HEV light absorbing compound.

7. The ophthalmic device of claim 1, wherein the ophthalmic device exhibits a shift in a peak wavelength by 1.6 nm or less and a decrease in amplitude of irradiance by less than 6.0% on a tristimulus colorimeter's blue primary when compared to a substantially similar ophthalmic device consisting essentially of the one or more polymerizable compounds and without the HEV light absorbing compound.

8. The ophthalmic device of claim 1, wherein the ophthalmic device exhibits a shift in a peak wavelength by less than 2.0 nm and a decrease in amplitude of irradiance by 5.4% or less on a tristimulus colorimeter's blue primary when compared to a substantially similar ophthalmic device consisting essentially of the one or more polymerizable compounds and without the HEV light absorbing compound.

9. The ophthalmic device of claim 1, wherein the ophthalmic device exhibits a shift in a peak wavelength by 1.6 nm or less and a decrease in amplitude of irradiance by 5.4% or less on a tristimulus colorimeter's blue primary when compared to a substantially similar ophthalmic device consisting essentially of the one or more polymerizable compounds and without the HEV light absorbing compound.

10. The ophthalmic device of claim 1, wherein the ophthalmic device exhibits a shift in chromaticity of perceptual neutral white by (0.033, 0.029) or less in XY color space with a tristimulus colorimeter.

11. The ophthalmic device of claim 1, wherein the HEV light absorbing compound comprises a compound of formula I:

Formula I

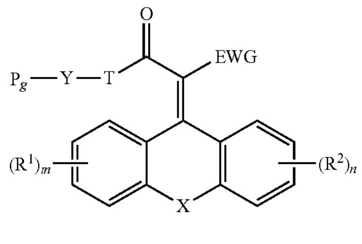

wherein:

m and n are independently 0, 1, 2, 3, or 4;

T is a bond, O, or NR;

X is O, S, NR, SO, or $SO_2$;

Y is a linking group;

$P_g$ is a polymerizable group;

R at each occurrence is independently H, $C_1$-$C_6$ alkyl, cycloalkyl, heterocycloalkyl, aryl, heteroaryl, or Y—$P_g$;

$R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and EWG is an electron withdrawing group.

12. An ophthalmic device that is a free radical reaction product of a reactive mixture comprising:

one or more polymerizable compounds suitable for making the ophthalmic device and a UV absorbing compound that is a benzophenone, a benzotriazole, a triazine, a substituted acrylonitrile, or mixtures thereof; and a tint mechanism configured to cause the ophthalmic device to transmit from 1 percent to 30 percent of light across a wavelength range of 400 to 409 nm, and from 10 percent to 95 percent of light across a wavelength range of 410 to 424 nm and from 1 percent to 70 percent of light across a wavelength range of 425 to 429 nm, and wherein the ophthalmic device exhibits a change in chromatic contrast of 0.5% or less in 70 to 98% of natural scene content.

13. The ophthalmic device of claim 12, wherein the ophthalmic device comprises a contact lens, a corneal onlay, a corneal inlay, an intraocular lens, or an overlay lens.

14. The ophthalmic device of claim 12, wherein the ophthalmic device comprises a hydrogel contact lens.

15. The ophthalmic device of claim 12, wherein the tint mechanism comprises a short-wavelength filter configured to filter one or more specific wavelengths in a spectral band of 380 nm-450 nm.

16. The ophthalmic device of claim 12, wherein the tint mechanism comprises a high energy visible (HEV) light absorbing compound configured to filter one or more specific wavelengths in a spectral band of 380 nm-450 nm.

17. The ophthalmic device of claim 12, wherein the ophthalmic device exhibits a shift in a peak wavelength by 1.6 nm or less and a decrease in amplitude of irradiance by less than 6.0% on a tristimulus colorimeter's blue primary when compared to a substantially similar ophthalmic device consisting essentially of the one or more polymerizable compounds and without the tint mechanism.

18. The ophthalmic device of claim 12, wherein the ophthalmic device exhibits a shift in a peak wavelength by less than 2.0 nm and a decrease in amplitude of irradiance by 5.4% or less on a tristimulus colorimeter's blue primary when compared to a substantially similar ophthalmic device consisting essentially of the one or more polymerizable compounds and without the tint mechanism.

19. The ophthalmic device of claim 12, wherein the ophthalmic device exhibits a shift in a peak wavelength by 1.6 nm or less and a decrease in amplitude of irradiance by 5.4% or less on a tristimulus colorimeter's blue primary when compared to a substantially similar ophthalmic device consisting essentially of the one or more polymerizable compounds and without the tint mechanism.

20. The ophthalmic device of claim 12, wherein the ophthalmic device exhibits a shift in chromaticity of perceptual neutral white by (0.033, 0.029) or less in XY color space with a tristimulus colorimeter.

21. An ophthalmic device that is a free radical reaction product of a reactive mixture comprising:

one or more polymerizable compounds suitable for making the ophthalmic device; and a high energy visible (HEV) light absorbing compound and a UV absorbing compound that is a benzophenone, a benzotriazole, a triazine, a substituted acrylonitrile, or mixtures thereof, wherein the ophthalmic device transmits from 1 percent to 30 percent of light across a wavelength range of 400 to 409 nm, and from 10 percent to 95 percent of light across a wavelength range of 410 to 424 nm, and wherein the ophthalmic device exhibits a shift in a peak wavelength by less than 2.0 nm and a decrease in amplitude of irradiance by less than 6.0% on a tristimulus colorimeter's blue primary when compared to a substantially similar ophthalmic device consisting essentially of the one or more polymerizable compounds and without the HEV light absorbing compound.

22. The ophthalmic device of claim 21, wherein the ophthalmic device comprises a contact lens, a corneal onlay, a corneal inlay, an intraocular lens, or an overlay lens.

23. The ophthalmic device of claim 21, wherein the ophthalmic device comprises a hydrogel contact lens.

24. The ophthalmic device of claim 21, wherein the ophthalmic device exhibits a shift in a peak wavelength by 1.6 nm or less and a decrease in amplitude of irradiance by less than 6.0% on a tristimulus colorimeter's blue primary when compared to a substantially similar ophthalmic device consisting essentially of the one or more polymerizable compounds and without the HEV light absorbing compound.

25. The ophthalmic device of claim 21, wherein the ophthalmic device exhibits a shift in a peak wavelength by less than 2.0 nm and a decrease in amplitude of irradiance by 5.4% or less on a tristimulus colorimeter's blue primary when compared to a substantially similar ophthalmic device consisting essentially of the one or more polymerizable compounds and without the HEV light absorbing compound.

26. The ophthalmic device of claim 21, wherein the ophthalmic device exhibits a shift in a peak wavelength by 1.6 nm or less and a decrease in amplitude of irradiance by 5.4% or less on a tristimulus colorimeter's blue primary when compared to a substantially similar ophthalmic device consisting essentially of the one or more polymerizable compounds and without the HEV light absorbing compound.

27. The ophthalmic device of claim 21, wherein the ophthalmic device exhibits a shift in chromaticity of perceptual neutral white by (0.033, 0.029) or less in XY color space with a tristimulus colorimeter.

* * * * *